United States Patent
Kim et al.

(10) Patent No.: US 9,437,826 B2
(45) Date of Patent: Sep. 6, 2016

(54) HETEROCYCLIC COMPOUND AND ORGANIC LIGHT-EMITTING DEVICE INCLUDING THE SAME

(71) Applicants: SAMSUNG DISPLAY CO., LTD., Yongin-City, Gyeonggi-Do (KR); PUSAN NATIONAL UNIVERSITY INDUSTRY-UNIVERSITY COOPERATION FOUNDATION, Busan (KR)

(72) Inventors: Jae-Hong Kim, Yongin (KR); Myeong-Suk Kim, Yongin (KR); Soung-Wook Kim, Yongin (KR); Hong-Suk Suh, Yongin (KR); Jin-Soo Hwang, Yongin (KR)

(73) Assignees: SAMSUNG DISPLAY CO., LTD., Yongin, Gyeonggi-do (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 390 days.

(21) Appl. No.: 14/167,037

(22) Filed: Jan. 29, 2014

(65) Prior Publication Data

US 2014/0367657 A1 Dec. 18, 2014

(30) Foreign Application Priority Data

Jun. 18, 2013 (KR) .......................... 10-2013-0069952

(51) Int. Cl.
| | |
|---|---|
| *H01L 51/54* | (2006.01) |
| *C09K 11/06* | (2006.01) |
| *H01L 51/00* | (2006.01) |
| *C07D 409/14* | (2006.01) |
| *H01L 51/50* | (2006.01) |

(52) U.S. Cl.
CPC ......... *H01L 51/0067* (2013.01); *C07D 409/14* (2013.01); *H01L 51/0071* (2013.01); *H01L 51/0072* (2013.01); *H01L 51/5016* (2013.01); *H01L 51/5056* (2013.01); *H01L 51/5072* (2013.01)

(58) Field of Classification Search
None
See application file for complete search history.

(56) References Cited

U.S. PATENT DOCUMENTS

2011/0037062 A1 2/2011 Fukumatsu et al.

FOREIGN PATENT DOCUMENTS

| | | | |
|---|---|---|---|
| JP | 2010238880 A | * | 10/2010 |
| KR | 10-2006-0085471 A | | 7/2006 |
| KR | 10-2008-0096733 A | | 11/2008 |
| KR | 10-2011-0007124 A | | 1/2011 |
| KR | 10-2011-0008784 A | | 1/2011 |
| KR | 10-2011-0134581 A | | 12/2011 |
| WO | WO 2011/010842 A2 | | 1/2011 |

OTHER PUBLICATIONS

Machine translation of JP2010-238880. Date of publication: Oct. 21, 2010.*

* cited by examiner

*Primary Examiner* — Andrew K Bohaty
(74) *Attorney, Agent, or Firm* — Lee & Morse, P.C.

(57) ABSTRACT

A heterocyclic compound, an organic light-emitting device, and a flat panel display apparatus, the compound being represented by Formula 1, below:

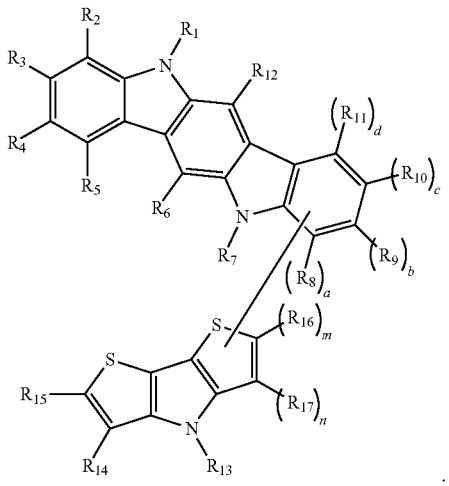

<Formula 1>

20 Claims, 1 Drawing Sheet

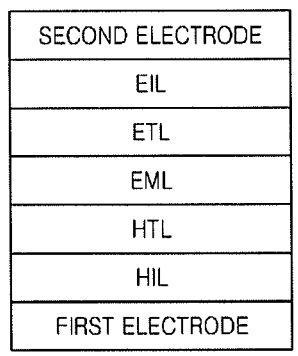

HETEROCYCLIC COMPOUND AND ORGANIC LIGHT-EMITTING DEVICE INCLUDING THE SAME

CROSS-REFERENCE TO RELATED APPLICATION

Korean Patent Application No. 10-2013-0069952, filed on Jun. 18, 2013, in the Korean Intellectual Property Office, and entitled: "Heterocyclic Compound and Organic Light-Emitting Device Including the Same," is incorporated by reference herein in its entirety.

BACKGROUND

1. Field

Embodiments relate to a heterocyclic compound and an organic light-emitting device including the same.

2. Description of the Related Art

Organic light-emitting devices (OLEDs), which are self-emitting devices, may have advantages such as wide viewing angles, excellent contrast, quick response, high brightness, excellent driving voltage characteristics, and may provide full color images.

An OLED may have a structure including a substrate, and an anode, a hole transport layer, an emission layer, an electron transport layer, and a cathode sequentially stacked on the substrate. The hole transport layer, the emission layer, and the electron transport layer may be organic thin films formed of organic compounds.

A driving principle of an organic light-emitting device having such a structure is described below.

When a voltage is applied between the anode and the cathode, holes injected from the anode may pass the hole transport layer and migrate toward the emission layer, and electrons injected from the cathode may pass the electron transport layer and migrate toward the emission layer. The holes and the electrons may be recombined with each other in the emission layer to generate excitons. Then, the excitons may be transitioned from an excited state to a ground state, thereby generating light.

SUMMARY

Embodiments are directed to a heterocyclic compound and an organic light-emitting device including the same.

The embodiments may be realized by providing a heterocyclic compound represented by Formula 1, below:

<Formula 1>

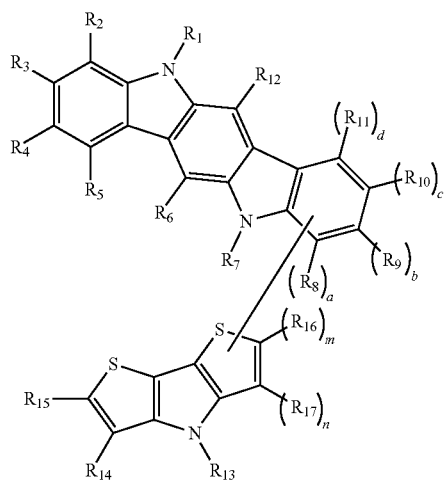

wherein, $R_1$ to $R_{17}$ are each independently a hydrogen atom, a deuterium atom, a substituted or unsubstituted $C_1$ to $C_{60}$ alkyl group, a substituted or unsubstituted $C_2$ to $C_{60}$ alkenyl group, a substituted or unsubstituted $C_2$ to $C_{60}$ alkynyl group, a substituted or unsubstituted $C_3$ to $C_{60}$ cycloalkyl group, a substituted or unsubstituted $C_1$ to $C_{60}$ alkoxy group, a substituted or unsubstituted $C_6$ to $C_{60}$ aryloxy group, a substituted or unsubstituted $C_6$ to $C_{60}$ arylthio group, a substituted or unsubstituted $C_6$ to $C_{60}$ aryl group, a substituted or unsubstituted $C_2$ to $C_{60}$ heteroaryl group, a substituted or unsubstituted $C_6$ to $C_{60}$ condensed polycyclic group, a halogen atom, a cyano group, a nitro group, a hydroxyl group, or a carboxyl group, and wherein a, b, c, d, m, and n are each independently 0 or 1, one of a, b, c, or d being 0, and one of m or n being 0.

The heterocyclic compound represented by Formula 1 may be represented by Formula 2, below:

<Formula 2>

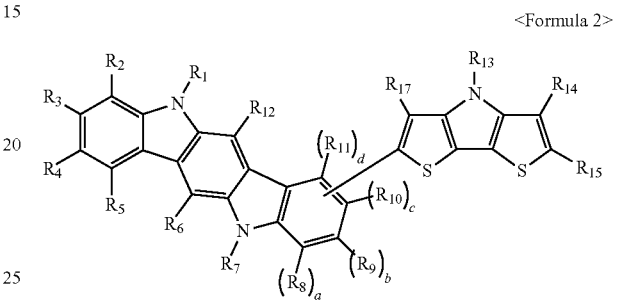

wherein $R_1$ to $R_{15}$, and $R_{17}$ in Formula 2 may be the same as defined with respect to Formula 1, and wherein a, b, c, and d may be each independently 0 or 1, one of a, b, c, or d being 0.

The heterocyclic compound represented by Formula 1 may be represented by Formula 3, below:

<Formula 3>

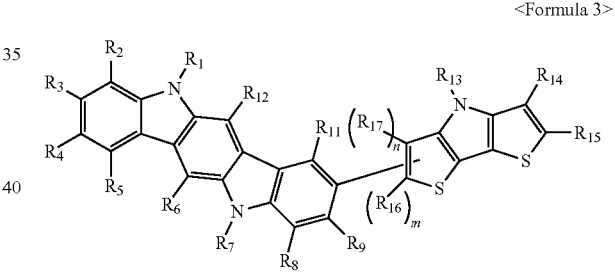

wherein $R_1$ to $R_9$, and $R_{11}$ to $R_{17}$ in Formula 3 may be the same as defined with respect to Formula 1, and wherein m and n are each independently 0 or 1, one of m or n being 0.

The heterocyclic compound represented by Formula 1 may be represented by Formula 4, below:

<Formula 4>

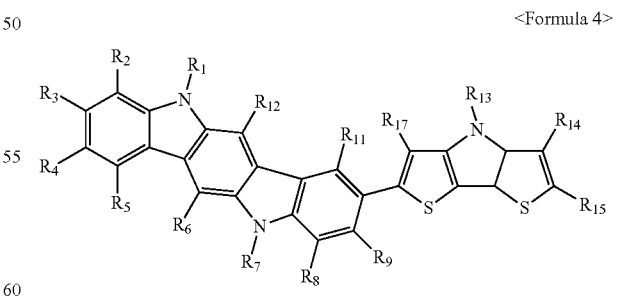

wherein $R_1$ to $R_9$, $R_{11}$ to $R_{15}$, and $R_{17}$ in Formula 4 are the same as defined with respect to Formula 1.

$R_1$, $R_3$, $R_4$, $R_7$, $R_{13}$, and $R_{15}$ in Formula 1 may each independently be a substituted or unsubstituted $C_6$ to $C_{60}$ aryl group, a substituted or unsubstituted $C_2$ to $C_{60}$ heteroaryl group, or a substituted or unsubstituted $C_6$ to $C_{60}$ condensed polycyclic group.

$R_1$, $R_3$, $R_4$, $R_7$, $R_{13}$, and $R_{15}$ in Formula 1 may be any one of Formulae 2a to 2d, below:

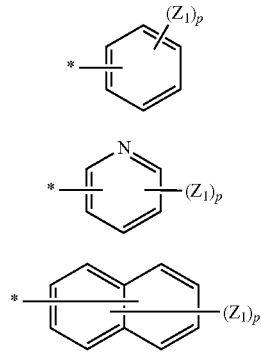

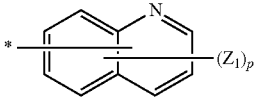

wherein, in Formulae 2a to 2d $Z_1$ and $Z_2$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, a halogen group, a cyano group, a nitro group, a hydroxyl group, or a carboxyl group; p is an integer of 1 to 7; and * indicates a binding site.

$R_2$, $R_5$, $R_6$, $R_8$ to $R_{12}$, $R_{14}$, $R_{16}$, and $R_{17}$ may each independently be a hydrogen atom or a deuterium atom.

The compound represented by Formula 1 may be any one of compounds 1-33, below:

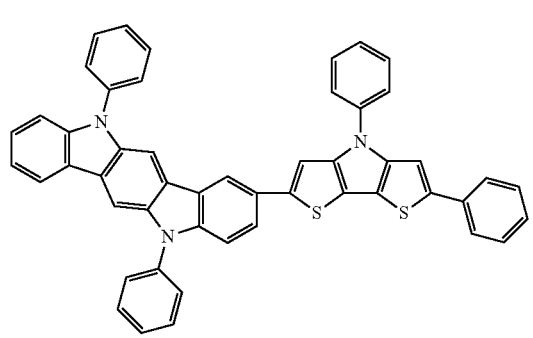

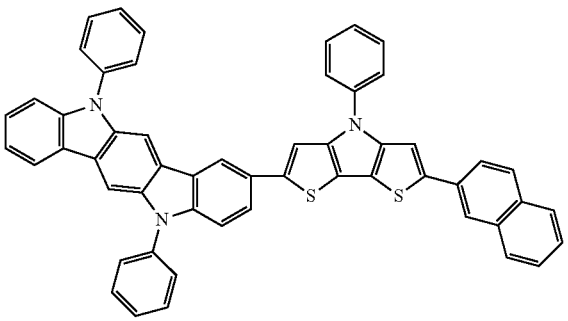

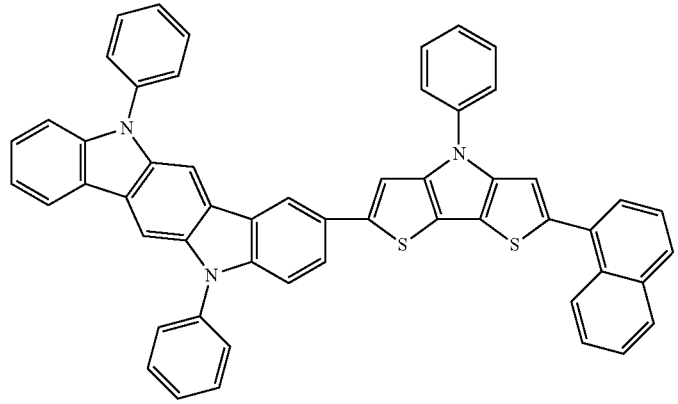

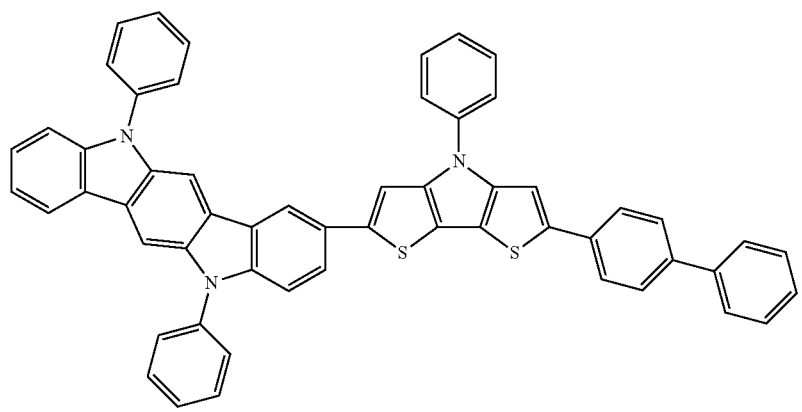

5
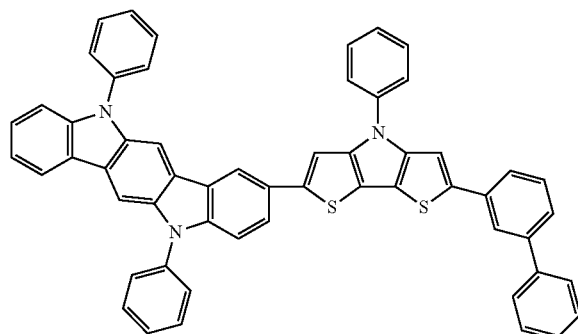
6
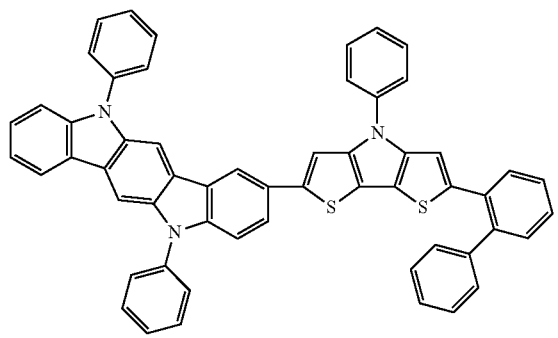
7
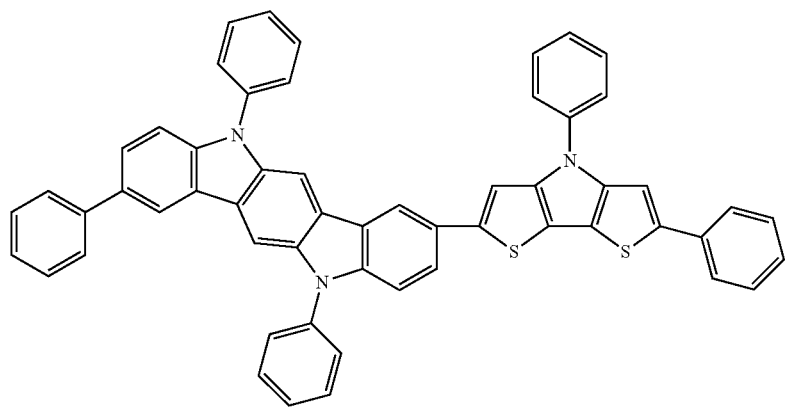
8
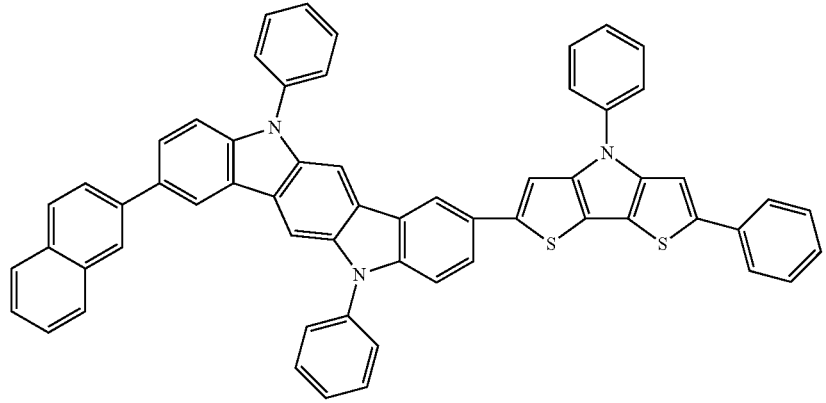
9
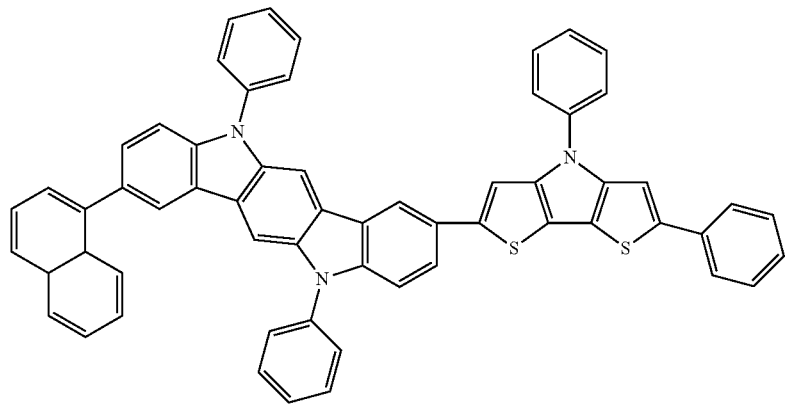

-continued
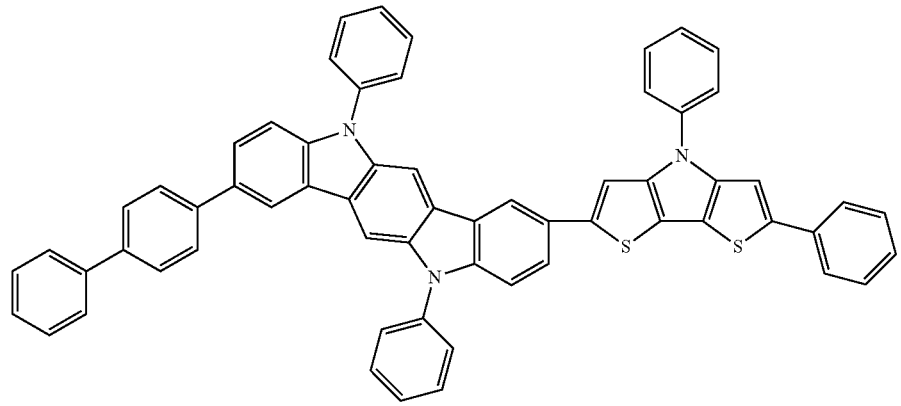
10
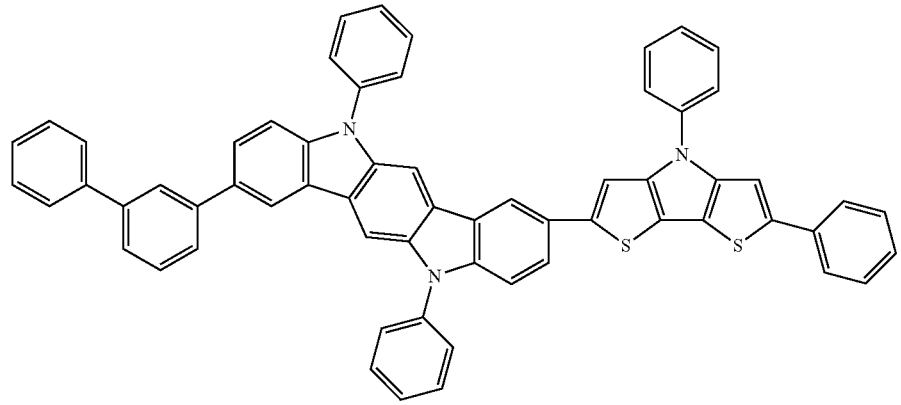
11
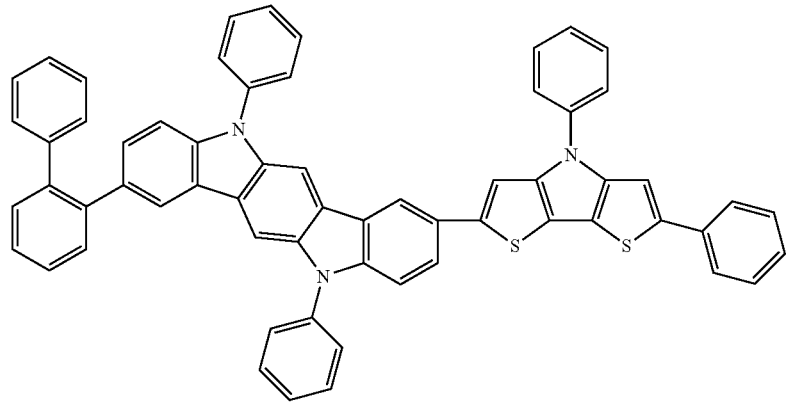
12
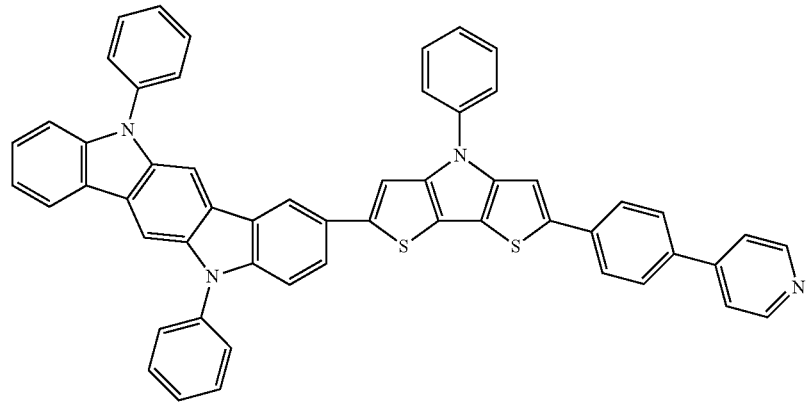
13

-continued
14
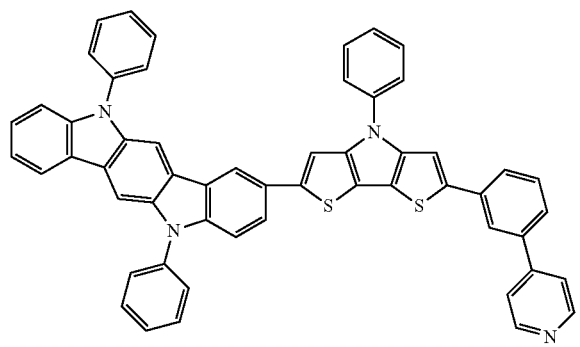
15
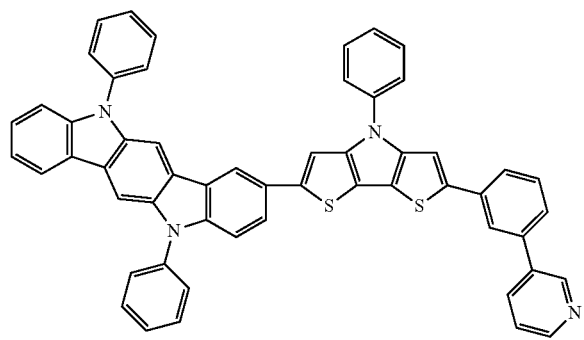
16
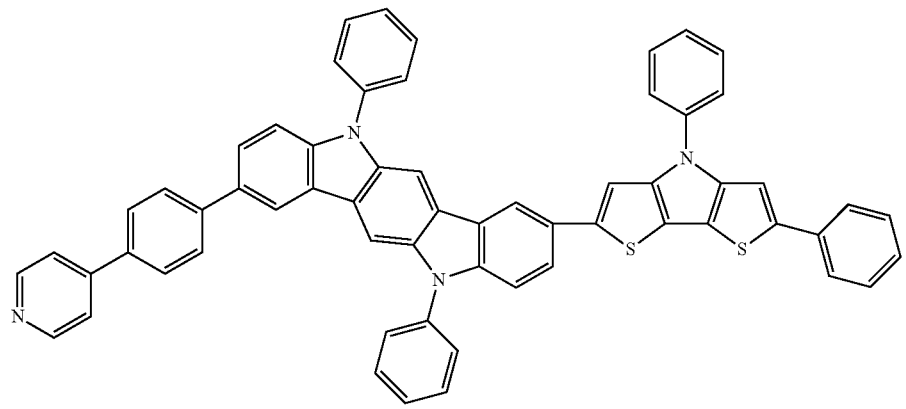
17
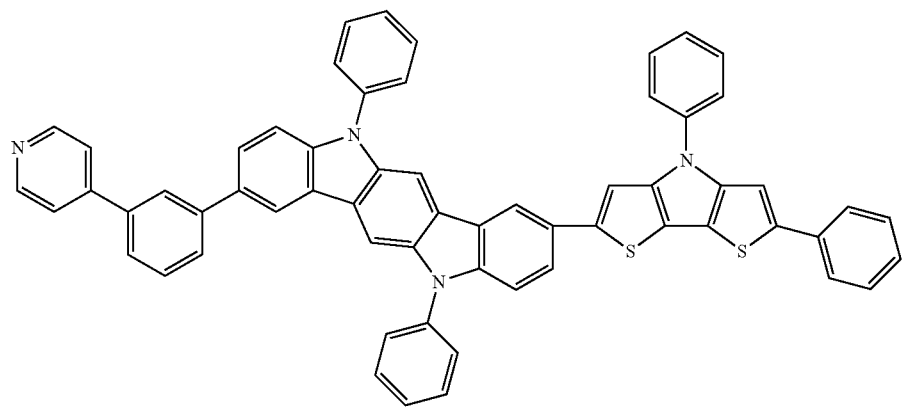
18
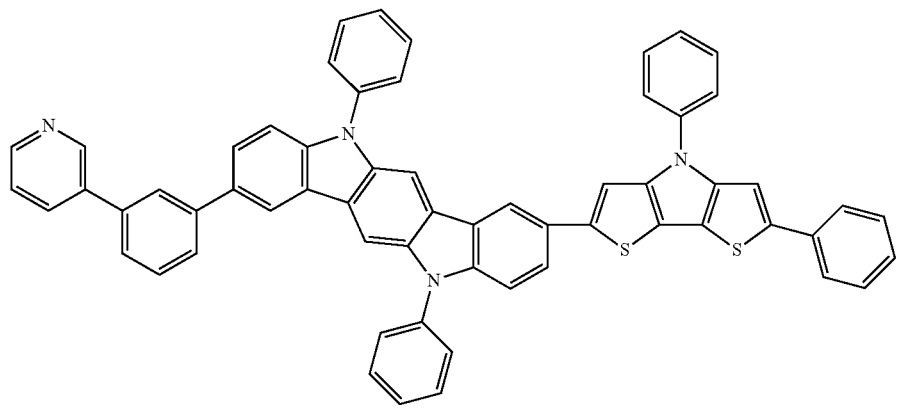

-continued
19
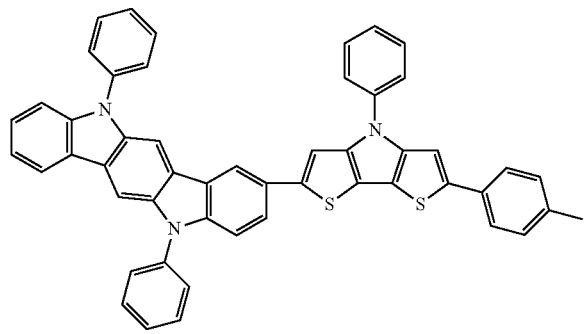
20
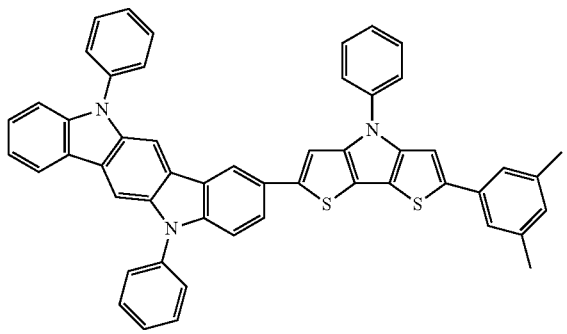
21
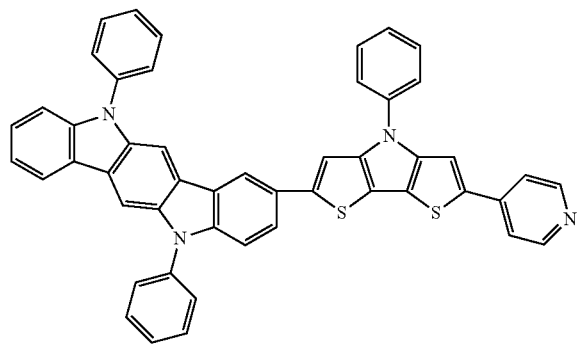
22
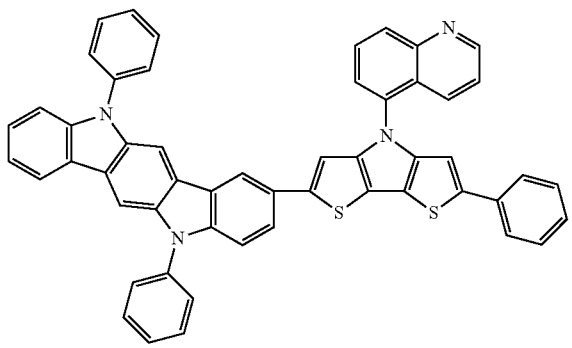
23
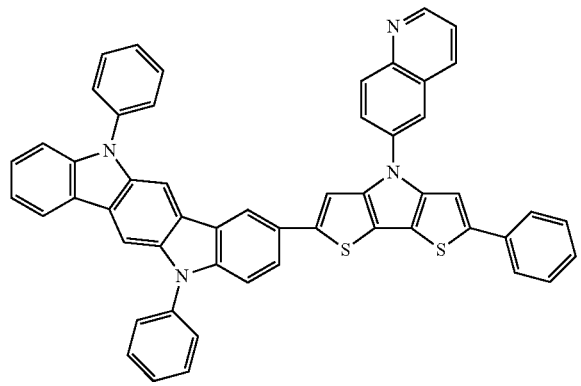
24
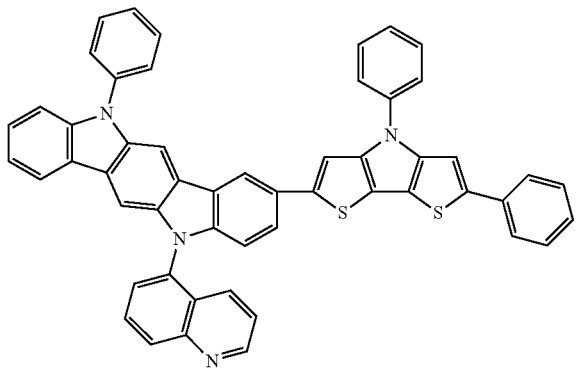
25
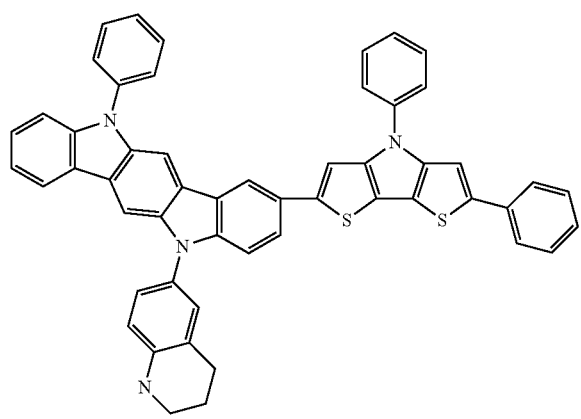
26
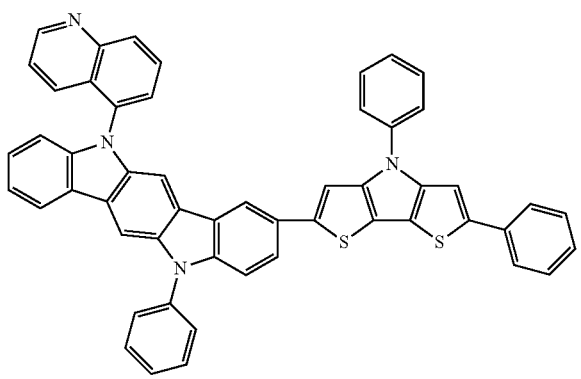

-continued
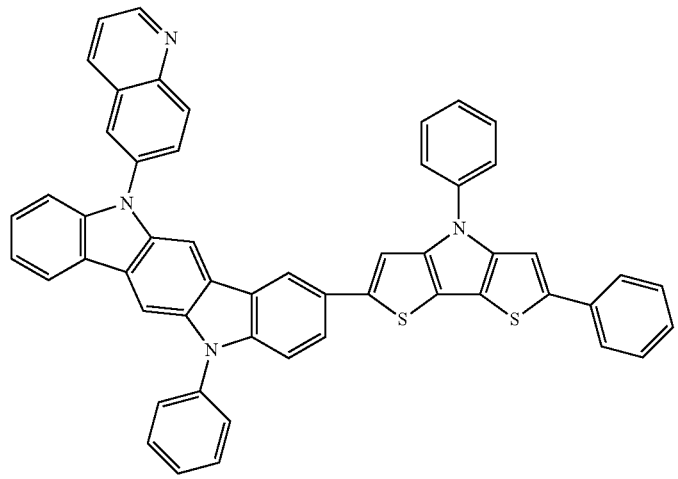
27
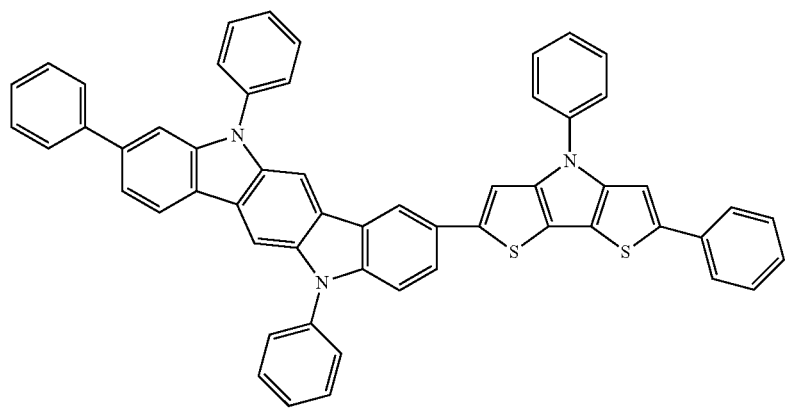
28
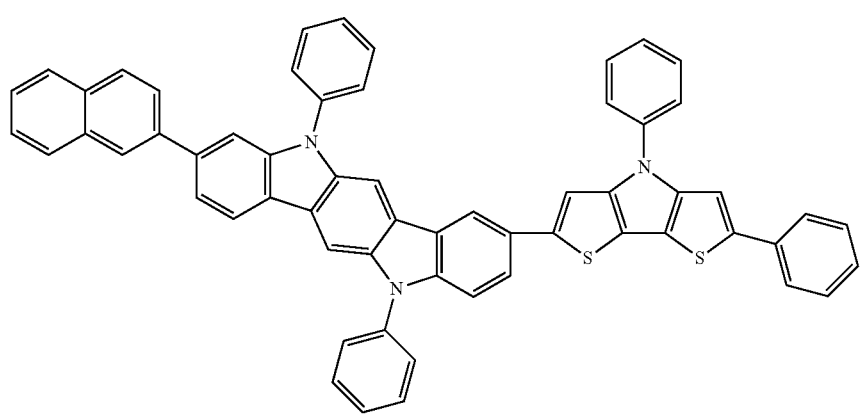
29

-continued
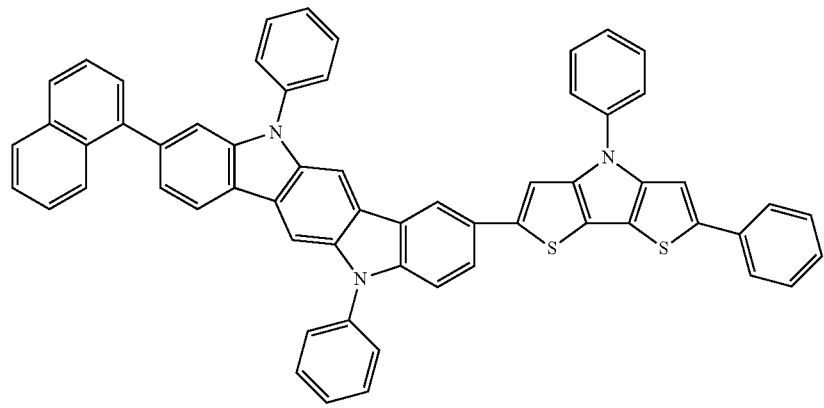
30
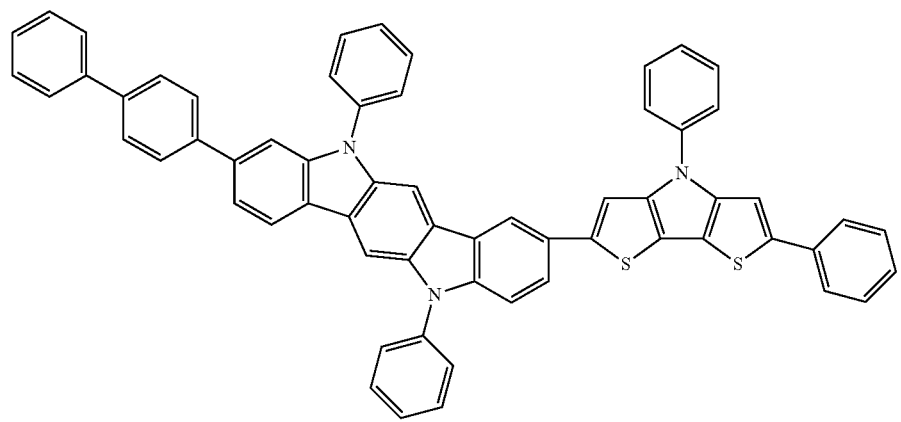
31
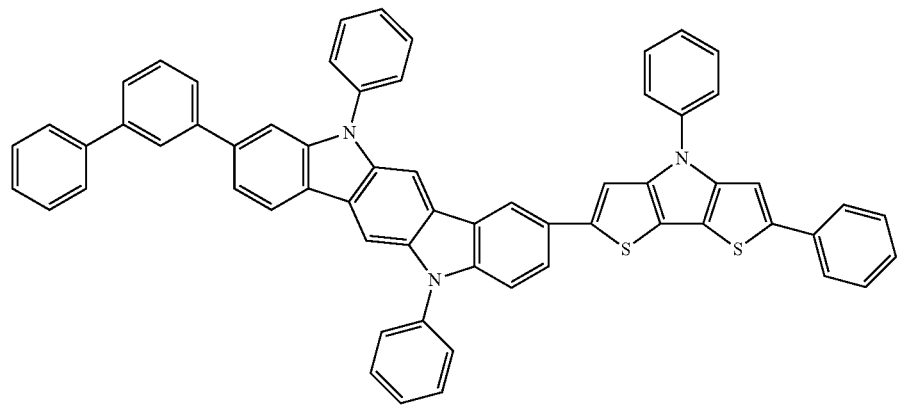
32

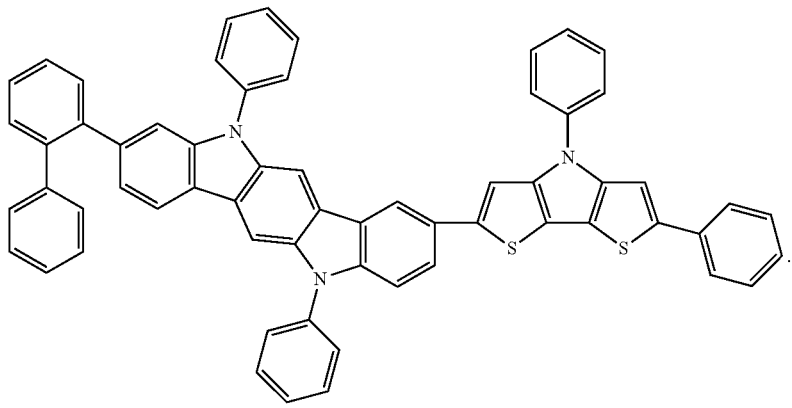

-continued

The embodiments may also be realized by providing an organic light-emitting diode including a first electrode; a second electrode; and an organic layer between the first electrode and the second electrode, wherein the organic layer includes the heterocyclic compound according to an embodiment.

The organic layer may include a hole injection layer, a hole transport layer, a functional layer having a hole injection capability and a hole transportation capability, an emission layer, an electron injection layer, an electron transport layer, or a functional layer having an electron injection capability and an electron transportation capability, The organic layer may be an emission layer, an electron transport layer, or a hole transport layer.

The organic layer may include an emission layer, and a hole injection layer, a hole transport layer, or a functional layer having a hole injection capability and a hole transportation capability, and the emission layer may include a red layer, a green layer, a blue layer, and a white layer, one of which includes a phosphorescent compound.

The hole injection layer, the hole transport layer, or the functional layer having a hole injection capability and a hole transportation capability may include a charge-generation material.

The charge-generation material may be a p-dopant.

The p-dopant may be a quinone derivative, metal oxide, or a cyano group-containing compound.

The organic layer may include an electron transport layer, the electron transport layer including a metal-containing material.

The metal-containing material may be a Li complex.

The metal-containing material may include one of lithium quinolate (LiQ) or Compound 203 below:

<203>

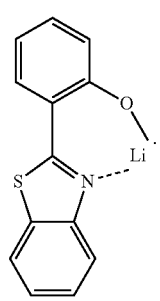

The organic layer may be formed by using a wet process performed by using the heterocyclic compound.

The embodiments may also be realized by providing a flat panel display apparatus, comprising the organic light-emitting device according to an embodiment, wherein the first electrode of the organic light-emitting device is electrically connected to a source electrode or a drain electrode of a thin film transistor.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Expressions such as "at least one of," when preceding a list of elements, modify the entire list of elements and do not modify the individual elements of the list.

A compound according to an embodiment may be represented by Formula 1, below.

<Formula 1>

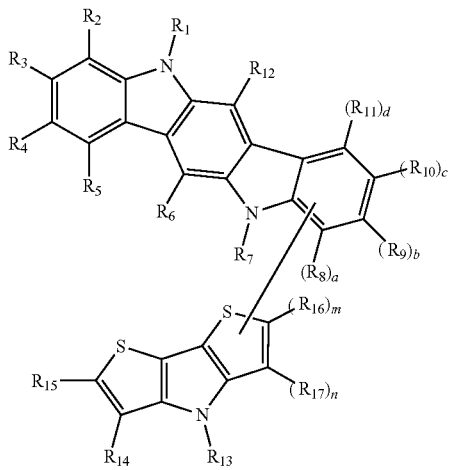

In Formula 1, $R_1$ to $R_{17}$ may each independently be a hydrogen atom, a deuterium atom, a substituted or unsubstituted $C_1$ to $C_{60}$ alkyl group, a substituted or unsubstituted $C_2$ to $C_{60}$ alkenyl group, a substituted or unsubstituted $C_2$ to $C_{60}$ alkynyl group, a substituted or unsubstituted $C_3$ to $C_{60}$ cycloalkyl group, a substituted or unsubstituted $C_1$ to $C_{60}$ alkoxy group, a substituted or unsubstituted $C_6$ to $C_{60}$ aryloxy group, a substituted or unsubstituted $C_6$ to $C_{60}$ arylthio group, a substituted or unsubstituted $C_6$ to $C_{60}$ aryl group, a substituted or unsubstituted $C_2$ to $C_{60}$ heteroaryl group, a substituted or unsubstituted $C_6$ to $C_{60}$ condensed polycyclic group, a halogen atom, a cyano group, a nitro group, a hydroxyl group, or a carboxyl group.

a, b, c, d, m, and n may each independently be 0 or 1. In an implementation, one of a, b, c, and d may be 0, and one of m and n may be 0.

The embodiments may provide a heterocyclic compound represented by Formula 1 as a green or red light-emitting material that shifts the wavelength to a longer wavelength, and also as a hole transport layer material, an electron transport layer material, or a doping material, and an organic light-emitting device with excellent electric characteristics due to the inclusion of the heterocyclic compound. The heterocyclic compound may have excellent hole-injection and hole-transportation capabilities from or to a metal electrode or an organic layer, together with excellent electron-injection and electron-transportation capabilities from or to a metal electrode or an organic layer. Thus, the heterocyclic compound may also be used as a hole transport layer material, an electron transport layer material, or a doping material for use in an organic light-emitting device.

The wording that in Formula 1, one of a, b, c, and d is 0 and one of m and n is 0 means that the

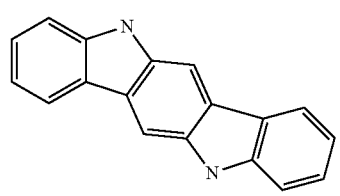 [SMILES: c1ccc2c(c1)[nH]c1cc3c(cc12)[nH]c1ccccc13]

moiety (substituents are not illustrated) binds to the

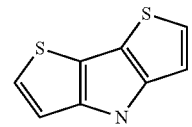 [SMILES: c1cc2[nH]c3ccsc3c2s1]

moiety (substituents are not illustrated) where the value of letters is 0.

In an implementation, the heterocyclic compound of Formula 1 may be represented by one of Formula 2, 3, or 4, below <Formula 2>

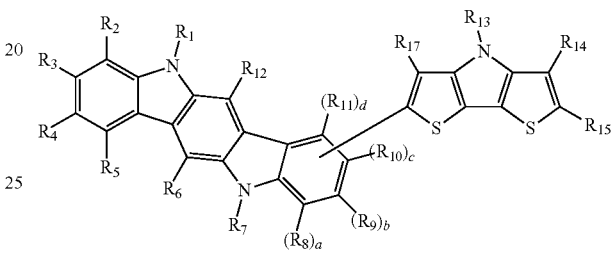

In Formula 2, $R_1$ to $R_{15}$ and $R_{17}$ may be the same as defined in connection with Formula 1. a, b, c, and d may each independently be 0 or 1, and one of a, b, c, and d may be 0.

<Formula 3>

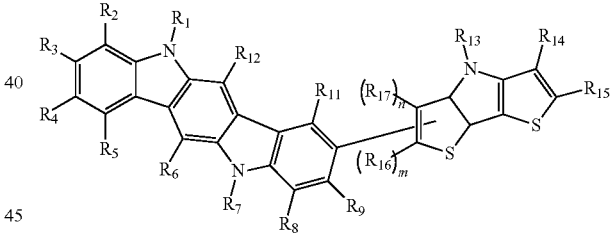

In Formula 3, $R_1$ to $R_9$, and $R_{11}$ to $R_{17}$ may be the same as defined in connection with Formula 1. m and n may each independently be 0 or 1, and one of m and n may be 0.

<Formula 4>

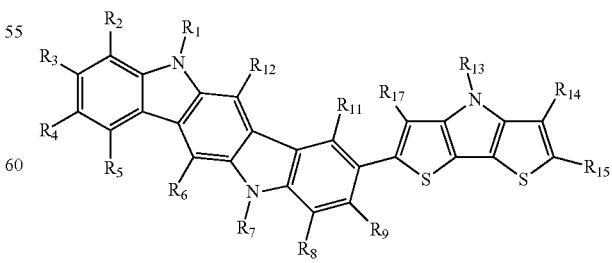

In Formula 4, $R_1$ to $R_9$, $R_{11}$ to $R_{15}$, and $R_{17}$ may be the same as defined in connection with Formula 1.

Hereinafter, substituents of the heterocyclic compound of Formula 1 will be described in detail.

According to an embodiment, $R_1$, $R_3$, $R_4$, $R_7$, $R_{13}$, and $R_{15}$ in Formula 1 may each independently be a substituted or unsubstituted $C_6$ to $C_{60}$ aryl group, a substituted or unsubstituted $C_2$ to $C_{60}$ heteroaryl group, or a substituted or unsubstituted $C_6$ to $_{60}$ condensed polycyclic group.

In an implementation, $R_1$, $R_3$, $R_4$, $R_7$, $R_{13}$, and $R_{15}$ in Formula 1 may each independently be any one of Formulae 2a to 2d, below.

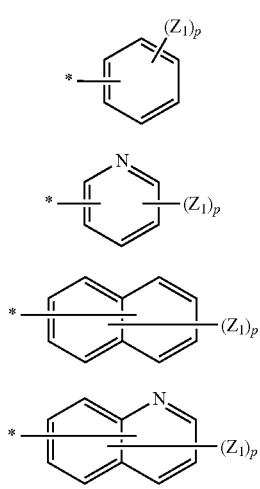

In Formulae 2a to 2d, $Z_1$ and $Z_2$ may each independently be a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, a halogen group, a cyano group, a nitro group, a hydroxyl group, or a carboxyl group.

p may be an integer of 1 to 7; and * indicates a binding site.

In an implementation, $R_2$, $R_5$, $R_6$, $R_8$ to $R_{12}$, $R_{14}$, $R_{16}$, and $R_{17}$ in Formula 1 may each independently be a hydrogen atom or a deuterium atom.

Hereinafter, definitions of representative substituents from among substituents used herein will be presented (the number of carbon numbers restricting a substituent is not limited, and does not limit properties of the substituent, and unless defined otherwise, the definition of the substituent is consistent with a general definition thereof).

The unsubstituted $C_1$ to $C_{60}$ alkyl group used herein may be a linear or branched alkyl group. Examples thereof may include a methyl group, an ethyl group, a propyl group, an isobutyl group, a sec-butyl group, a pentyl group, an iso-amyl group, a hexyl group, a heptyl, an octyl, a nonanyl, and a dodecyl group. In an implementation, at least one hydrogen atom of the alkyl group may be substituted with a deuterium atom, a halogen atom, a hydroxyl group, a nitro group, a cyano group, an amino group, an amidino group, a hydrazine group, a hydrazone group, a carboxyl group or salt thereof, a sulfonic acid or salt thereof, a phosphoric acid or salt thereof, a $C_1$ to $C_{10}$ alkyl group, a $C_1$ to $C_{10}$ alkoxy group, a $C_2$ to $C_{10}$ alkenyl group, a $C_2$ to $C_{10}$ alkynyl group, a $C_6$ to $C_{16}$ aryl group, or a $C_2$ to $C_{16}$ heteroaryl group.

The unsubstituted $C_2$ to $C_{60}$ alkenyl group used herein may refer to an unsubstituted alkyl group having one or more carbon double bonds at a center or end thereof. Examples thereof may include ethenyl, prophenyl, and butenyl. In an implementation, at least one hydrogen atom of the unsubstituted alkenyl group may be substituted with the same substituents as described in connection with the substituted alkyl group.

The unsubstituted $C_2$ to $C_{60}$ alkynyl group used herein may refer to an unsubstituted alkyl group having one or more carbon triple bonds at a center or end thereof. Examples thereof may include acetylene, propylene, phenylacetylene, naphthylacetylene, isopropylacetylene, t-butylacetylene, and diphenylacetylene. In an implementation, at least one hydrogen atom of the unsubstituted alkynyl group may be substituted with the same substituents as described in connection with the substituted alkyl group.

The unsubstituted $C_3$ to $C_{60}$ cycloalkyl group used herein may refer to a $C_3$ to $C_{60}$ cyclic alkyl group. In an implementation, at least one hydrogen atom of the cycloalkyl group may be substituted with the same substituents as described in connection with the $C_1$ to $C_{60}$ alkyl group.

The unsubstituted $C_1$ to $C_{60}$ alkoxy group used herein may refer to a group having —OA (wherein A is the unsubstituted $C_1$ to $C_{60}$ alkyl group). Examples thereof may include ethoxy, ethoxy, isopropyloxy, butoxy, and pentoxy. In an implementation, at least one hydrogen atom of the unsubstituted alkoxy group may be substituted with the same substituents as described in connection with the alkyl group.

The unsubstituted $C_6$ to $C_{60}$ aryl group used herein may refer to a carbocyclic aromatic system having at least one aromatic ring. In an implementation, when a number of rings is two or more, the rings may be fused to each other or may be linked to each other via, e.g., a single bond. The term 'aryl' may include an aromatic system, such as phenyl, naphthyl, or anthracenyl. In an implementation, at least one hydrogen atom of the aryl may be substituted with the same substituents described in connection with the $C_1$ to $C_{60}$ alkyl group.

Examples of a substituted or unsubstituted $C_6$ to $_{60}$ aryl group may include a phenyl group, a $C_1$ to $C_{10}$ alkylphenyl group (for example, an ethylphenyl group), a biphenyl group, a $C_1$ to $C_{10}$ alkylbiphenyl group, a $C_1$ to $C_{10}$ akoxybiphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl) aminophenyl group, a (N,N'-diphenyl)aminophenyl group, a pentalenyl group, an indenyl group, a naphthyl group, a $C_1$ to $C_{10}$ alkylnaphthyl group (for example, methylnaphthyl group), a $C_1$ to $C_{10}$ akoxynaphthyl group (for example, methoxynaphthyl group), an anthracenyl group, an azrenyl group, a heptalenyl group, an acenaphthylenyl group, a phenalenyl group, a fluorenyl group, an anthraquinolinyl group, a methylan anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentasenyl group, a tetraphenylenyl group, a hexaphenyl group, a hexacenyl group, a rubicenyl group, a coroneryl group, trinaphthylenyl group, a heptaphenyl group, a heptacenyl group, a piranthrenyl group, and an obarenyl group.

The unsubstituted $C_2$-$C_{60}$ heteroaryl group used herein may include at least one hetero atom selected from nitrogen (N), oxygen (O), phosphorous (P), or sulfur (S). In an implementation, when the group has two or more rings, the rings may be fused to each other or may be linked to each other via, for example, a single bond. Examples of the unsubstituted $C_2$-$C_{60}$ heteroaryl group may include a pyrazolyl group, an imidazolyl group, a oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. In an implementation, at least one hydrogen atom of the heteroaryl may be substituted with the same substituents described in connection with the $C_1$ to $C_{60}$ alkyl group.

The $C_6$ to $C_{60}$ unsubstituted aryloxy group used herein may refer to a group represented by —$OA_1$, wherein $A_1$ is the $C_6$ to $C_{60}$ aryl group. An example of the aryloxy group may include a phenoxy group. In an implementation, at least one hydrogen atom of the aryloxy may be substituted with the same substituents described in connection with the $C_1$ to $C_{60}$ alkyl group.

The unsubstituted $C_6$ to $C_{60}$ arylthio group used herein may refer to a group represented by —$SA_1$, wherein $A_1$ is the $C_6$ to $C_{60}$ aryl group Examples of the arylthio group may include a benzenethio group and a naphthylthio group. In an implementation, at least one hydrogen atom of the arylthio group may be substituted with the same substituents described in connection with the $C_1$ to $C_{60}$ alkyl group.

The unsubstituted $C_6$ to $C_{60}$ condensed polycyclic group used herein may refer to a substituent having two or more rings formed by fusing at least one aromatic ring and/or at least one non-aromatic ring or a substituent in which a unsaturated group is present in a ring but a conjugated system does not exist, and the condensed polycyclic group overall does not have an orientation, which is why the condensed polycyclic group is distinguished from the aryl group or the heteroaryl group.

Examples of the heterocyclic compound represented by Formula 1 may include the compounds (e.g., 1-33), below.

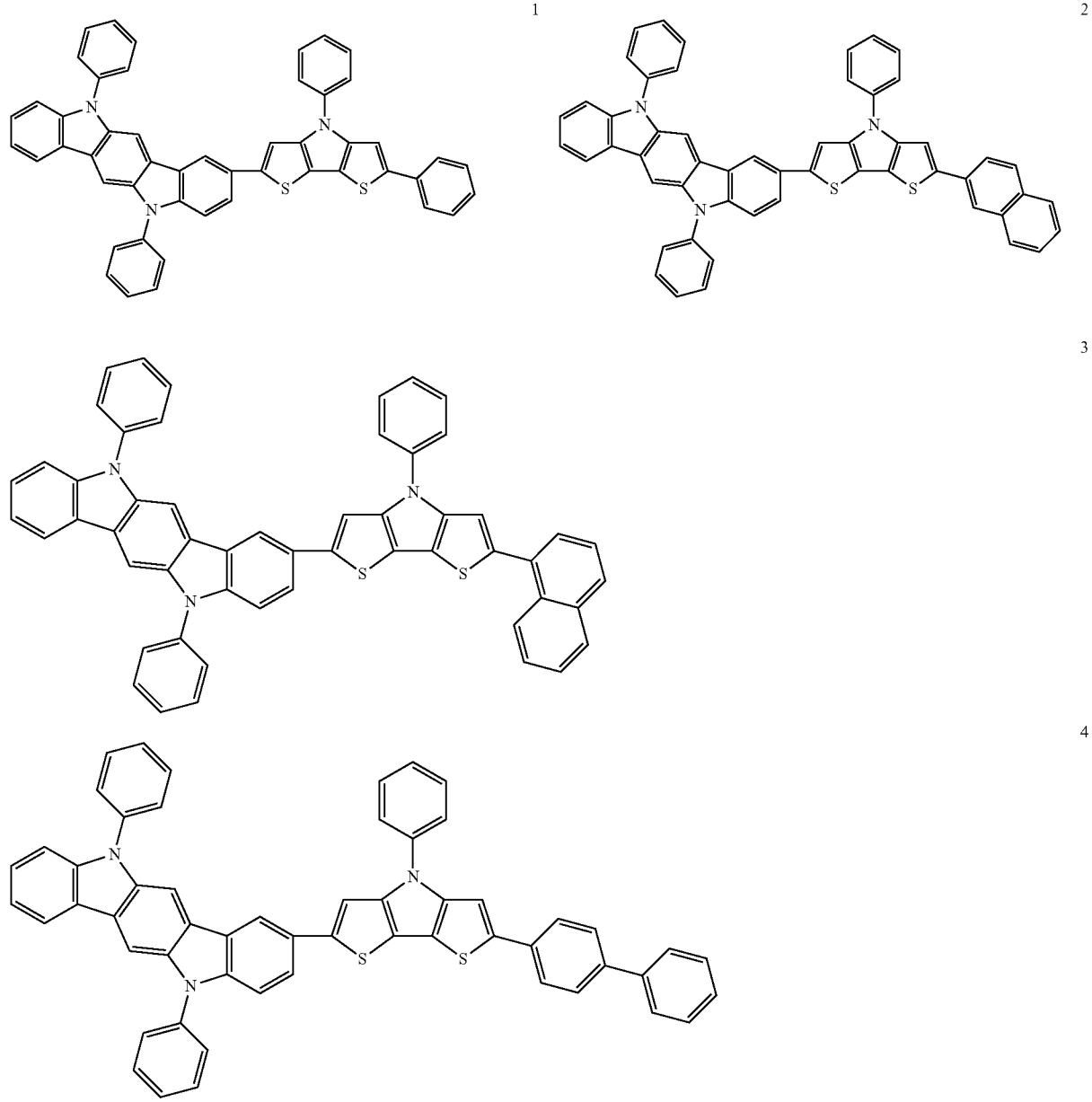

-continued
5
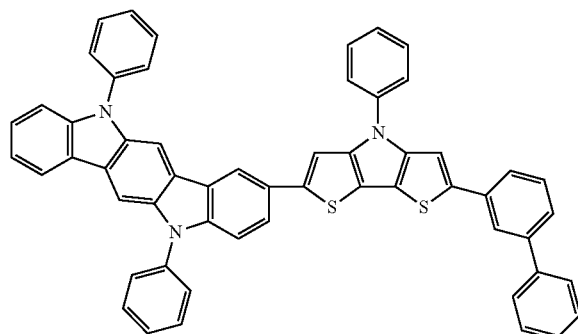
6
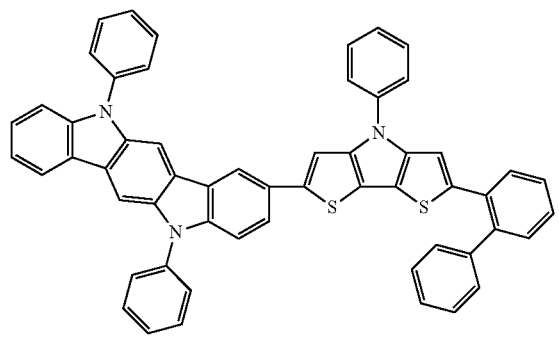
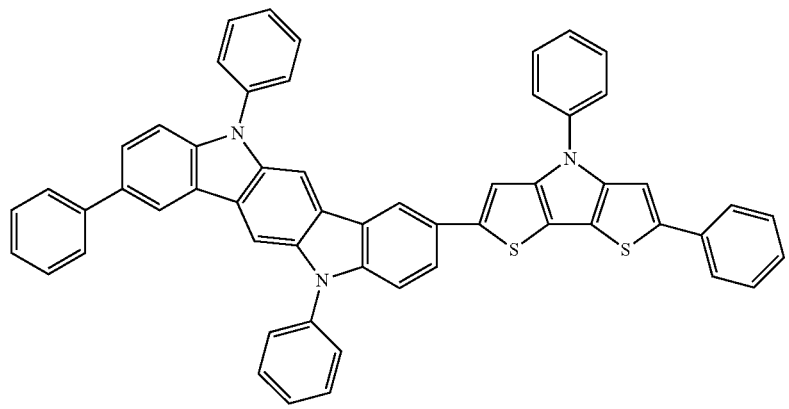
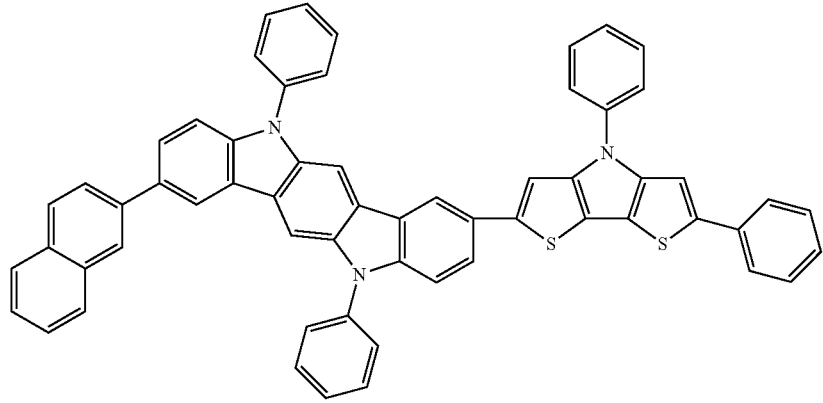
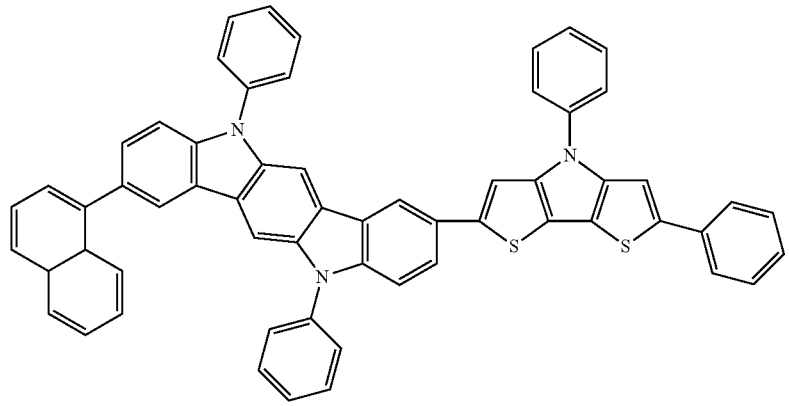

-continued
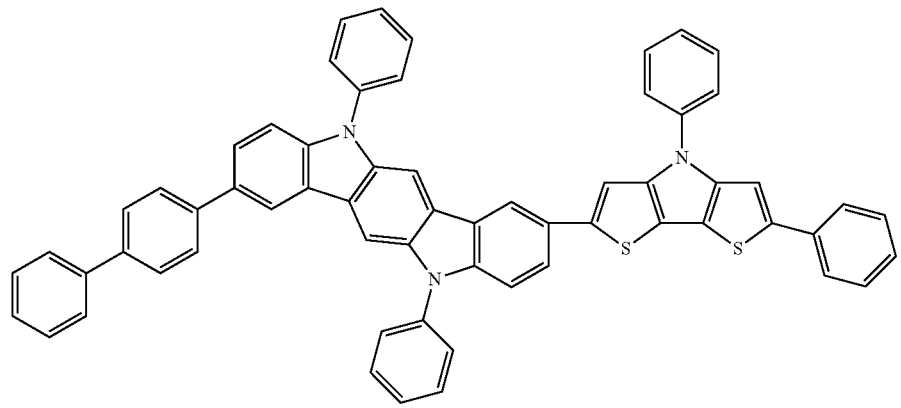
10
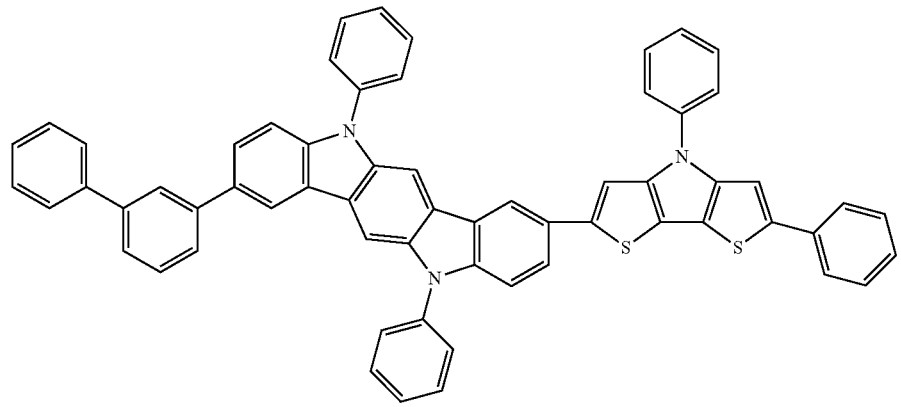
11
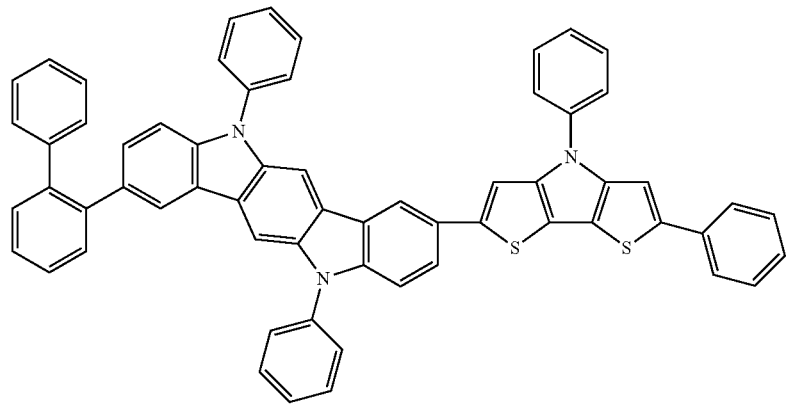
12
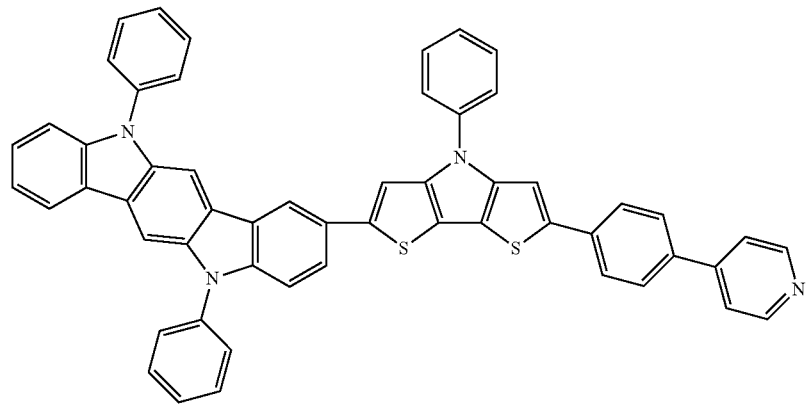
13

-continued
14
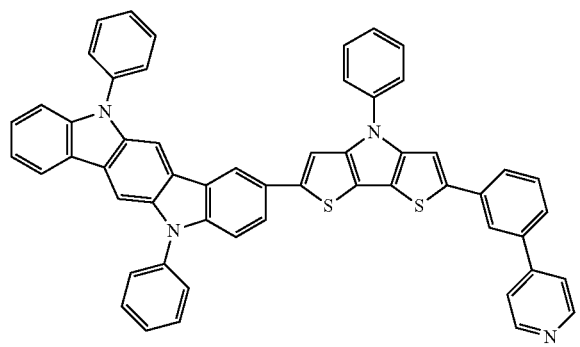
15
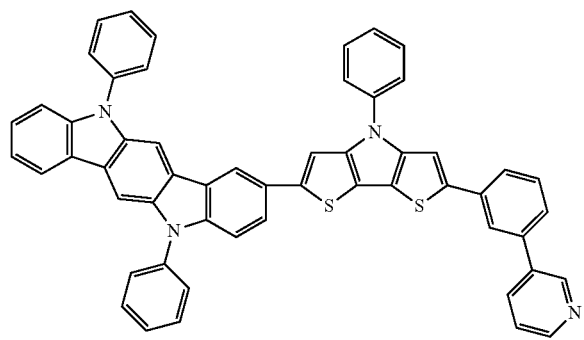
16
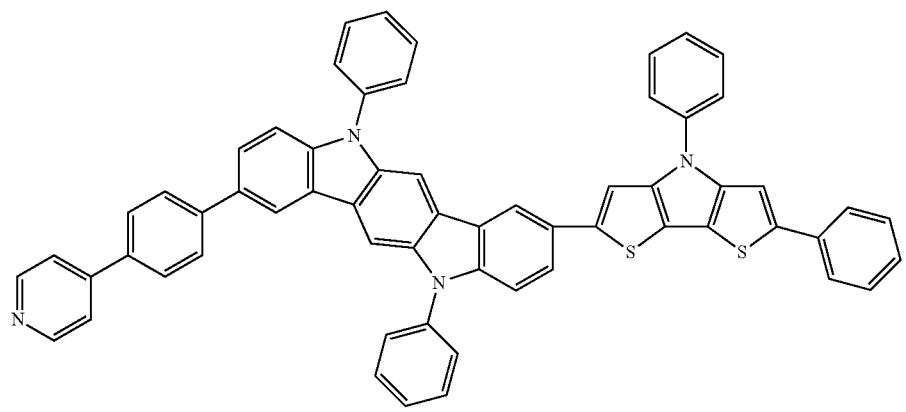
17
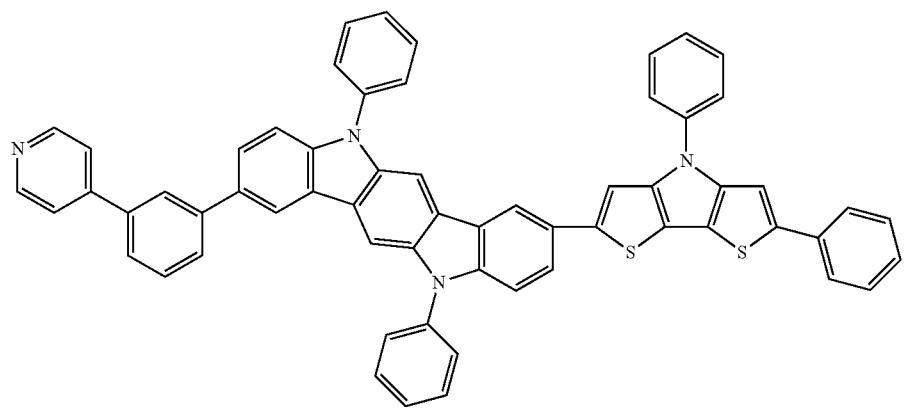
18
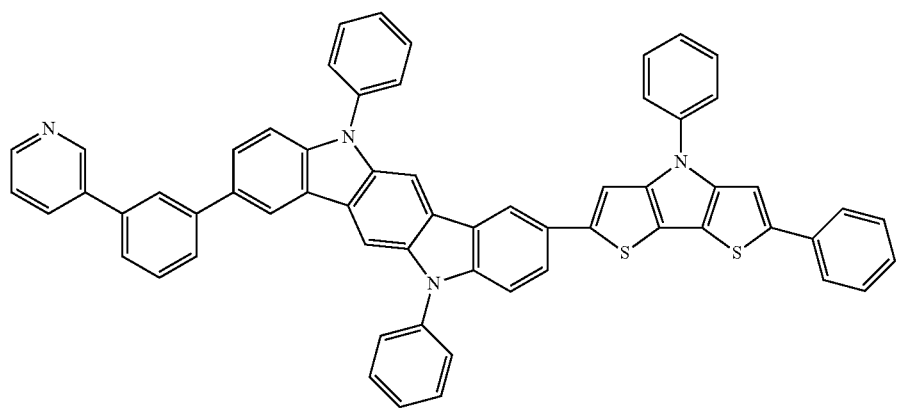

-continued
19
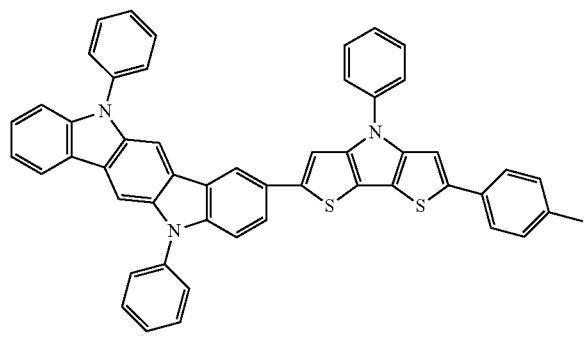
20
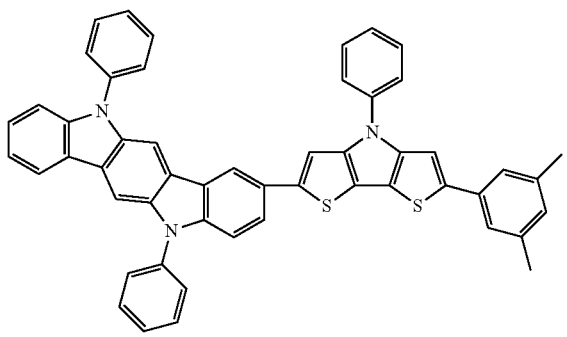
21
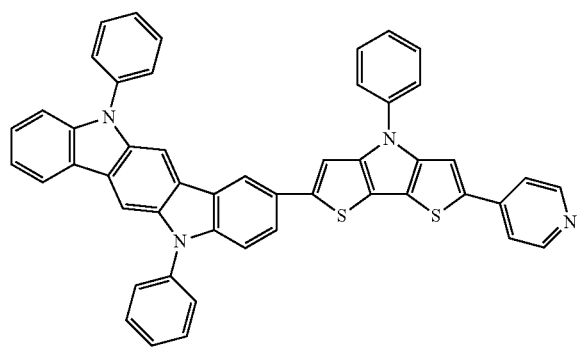
22
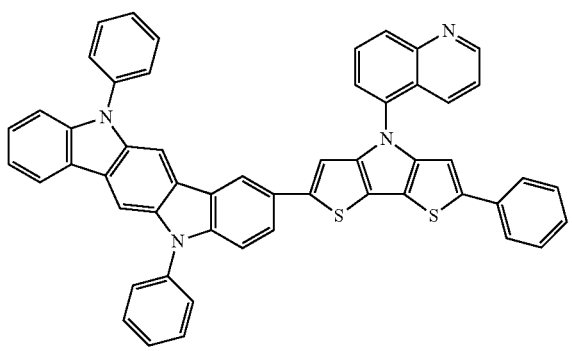
23
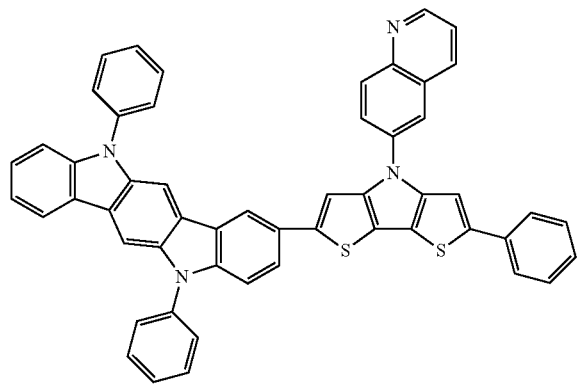
24
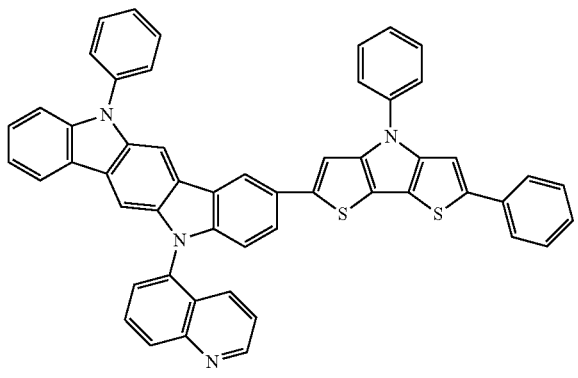
25
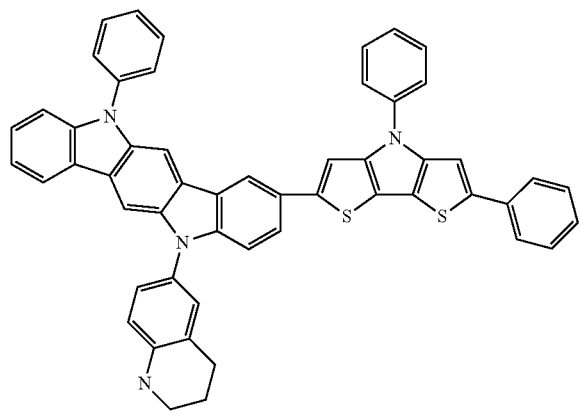
26
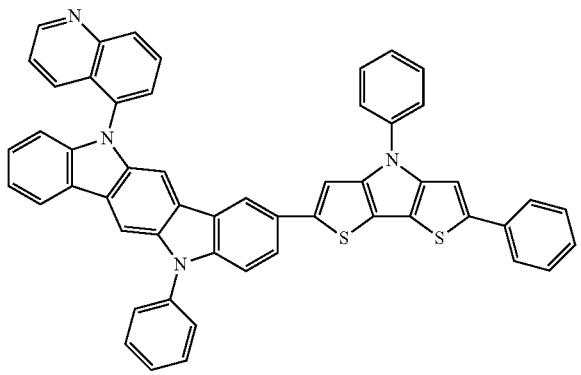

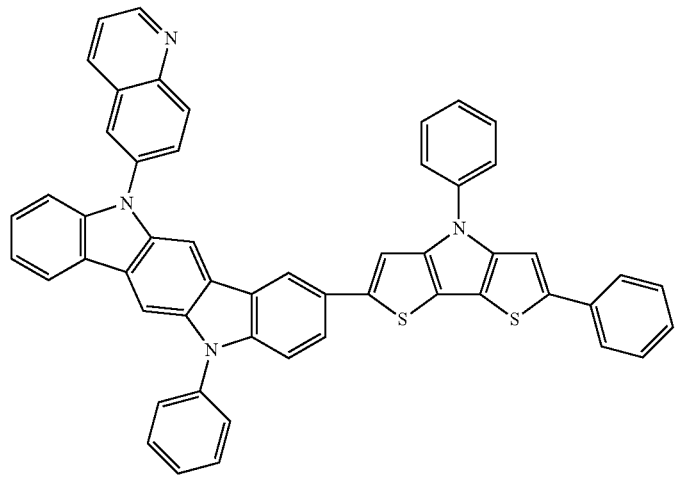
27
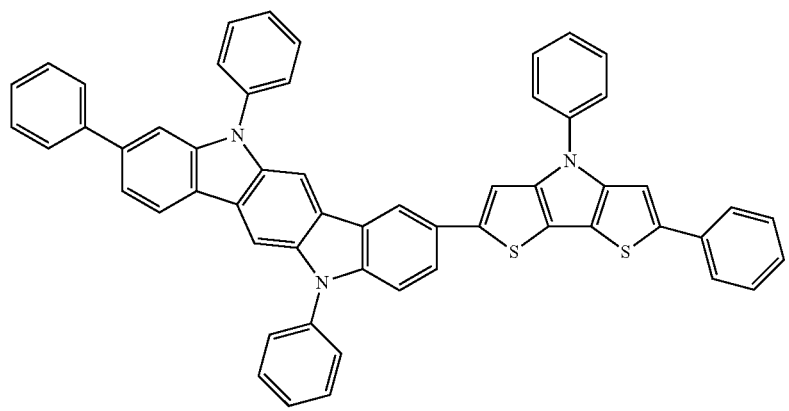
28
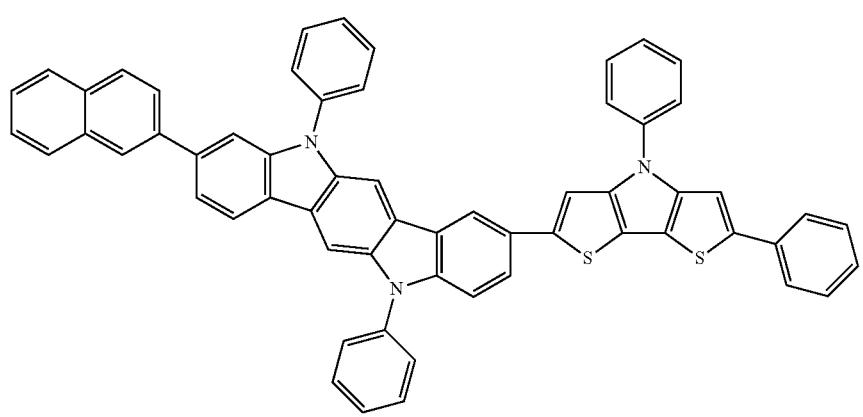
29

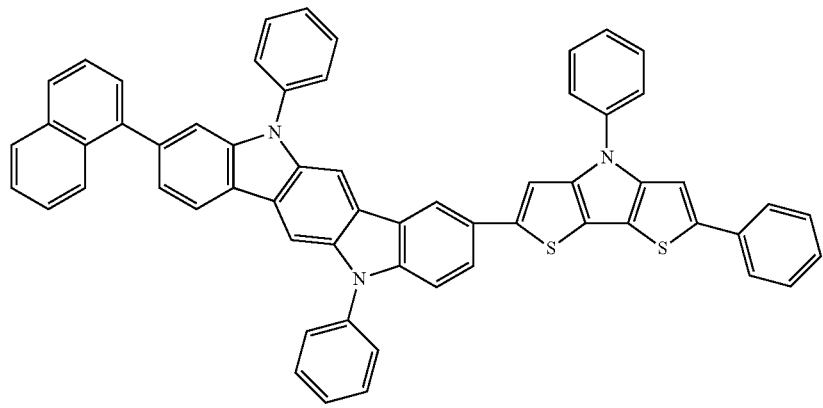
30
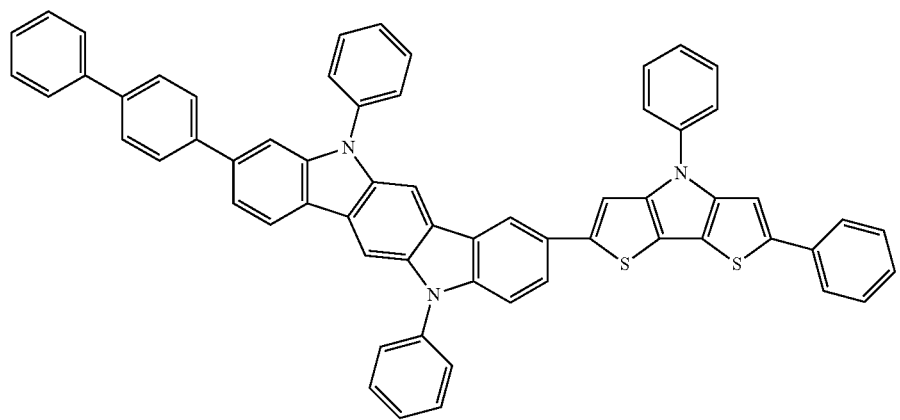
31
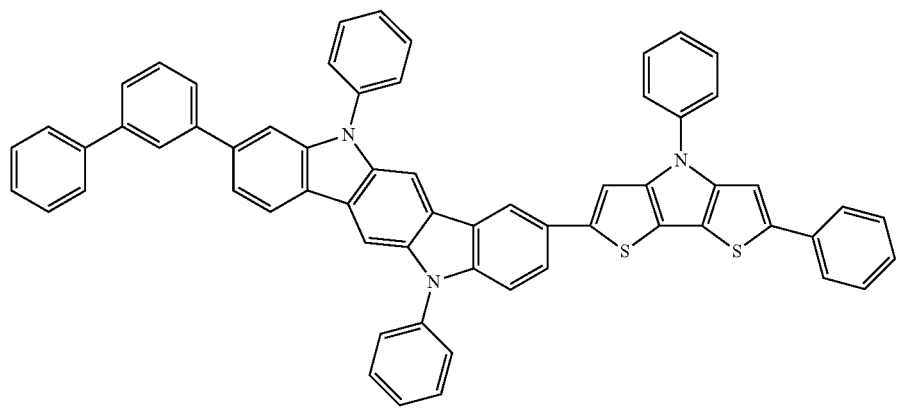
32

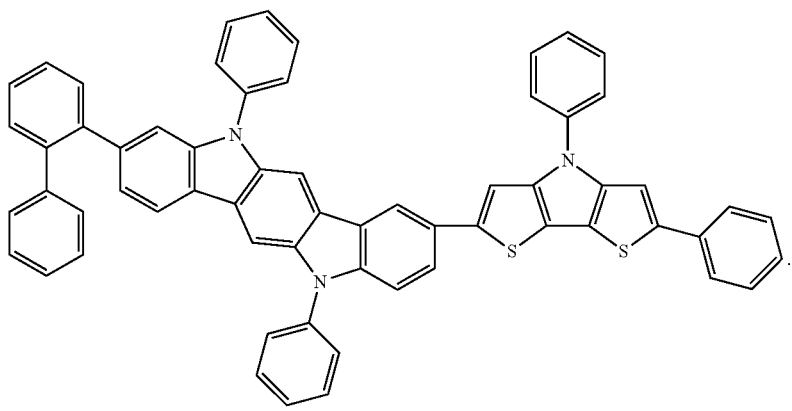

An organic light-emitting device according to an embodiment may include a first electrode, a second electrode, and an organic layer interposed between the first electrode and the second electrode. The organic layer may include the heterocyclic compound represented by Formula 1, above.

The organic layer may include at least one layer selected from a hole injection layer, a hole transport layer, a functional layer having a hole injection function and a hole transport function (hereinafter referred to as "H-functional layer"), a buffer layer, an electron blocking layer, an emission layer, a hole blocking layer, an electron transport layer, an electron injection layer, or a functional layer having an electron transport function and an electron injection function (hereinafter referred to as "E-functional layer").

For example, the organic layer may be an emission layer, an electron transport layer, or a hole transport layer. In an implementation, the organic layer may be a green emission layer or a red emission layer.

In an implementation, the organic layer may further include an electron injection layer, an electron transport layer, a functional layer having an electron injection capability and an electron transportation capability, an emission layer, a hole injection layer, a hole transport layer, or a functional layer having a hole injection capability and a hole transportation capability. The emission layer may further include an anthracene-based compound, an arylamine-based compound, or a styryl-based compound.

In an implementation, the organic layer may include an electron injection layer, an electron transport layer, an emission layer, a hole injection layer, a hole transport layer, or a functional layer having a hole injection capability and a hole transportation capability. The emission layer may include a red layer, a green layer, a blue layer, and a white layer, and any one of these layers may include a phosphorescent compound, and the hole injection layer, the hole transport layer, or the functional layer having a hole injection capability and a hole transportation capability may include a charge-generation material. Also, the charge-generation material may be a p-dopant, and the p-dopant may be a quinone derivative, a metal oxide, or a cyano group-containing compound.

In an implementation, the organic layer may include an electron transport layer that includes an electron-transportable organic compound and a metal complex. The metal complex may be a Li complex.

The term "organic layer" used herein may refer to a single layer and/or a multi-layer interposed between the first electrode and the second electrode of an organic light-emitting device.

The organic layer may include an emission layer, and the emission layer may include the compound represented by Formula 1. The organic layer may include at least one layer selected from a hole injection layer, a hole transport layer, or a H-functional layer, and the at least one layer selected from a hole injection layer, hole transport layer, and H-functional layer may include the compound.

FIG. 1 illustrates a schematic cross-sectional view of an organic light-emitting device according to an embodiment. Hereinafter, with reference to FIG. 1, the structure of an organic light-emitting device according to an embodiment, and a method of manufacturing the organic light-emitting device, according to an embodiment of the present invention, will be described in detail.

A substrate (not shown) may be any one of various substrates that are suitably used in an organic light-emitting device. For example, the substrate may include a glass substrate or a transparent plastic substrate with excellent mechanical strength, thermal stability, transparency, surface smoothness, ease of handling, and water repellency.

A first electrode may be formed by depositing or sputtering a material for a first electrode on the substrate. When the first electrode is an anode, the material for the first electrode may be selected from materials with a high work function to facilitate injection of holes. The first electrode may be a reflective electrode or a transmissive electrode. The material for the first electrode may include a transparent material with high conductivity, and examples of such a material may include indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be used as a reflective electrode.

The first electrode may be a single- or multi-layered structure. For example, the first electrode may have a three-layered structure of ITO/Ag/ITO.

An organic layer may be disposed on the first electrode. The organic layer may include a hole injection layer, a hole transport layer, a buffer layer (not shown), an emission layer, an electron transport layer, and/or an electron injection layer.

A hole injection layer (HIL) may be formed on the first electrode by using various methods, such as vacuum deposition, spin coating, casting, LB deposition, or the like.

When a HIL is formed by vacuum deposition, the deposition conditions may vary according to a material that is used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, a coating speed may be from about 2,000 rpm to about 5,000 rpm, and a temperature at which a heat treatment is performed to remove a solvent after coating may be from about 80° C. to about 200° C.

The hole injection material may include, e.g., N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenyl-phenylamino)triphenylamine (m-MTDATA), N,N'-di(1-naphthyl)-N,N'-diphenylbenzidine (NPB), TDATA, 2-TNATA, a polyaniline/dodecylbenzenesulfonic acid (pani/DBSA), poly(3,4-ethylenedioxythiophene)/poly(4-styrene-sulfonate) (PEDOT/PSS), polyaniline/camphor sulfonicacid (pani/CSA), or (polyaniline)/poly(4-styrenesulfonate) (PANI/PSS).

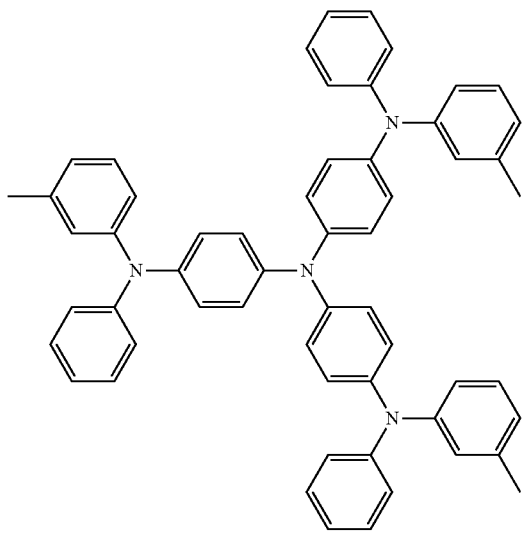

m-MTDATA

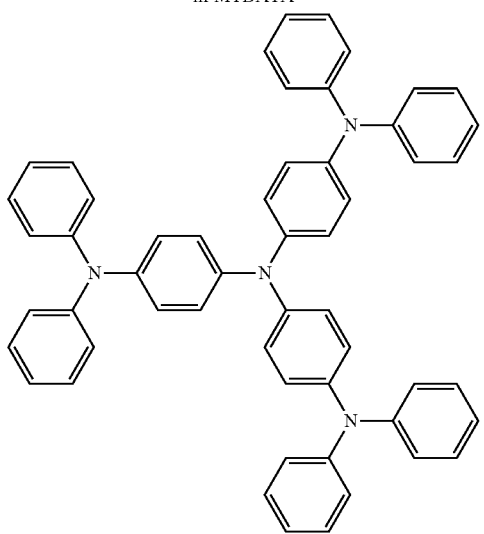

TDATA

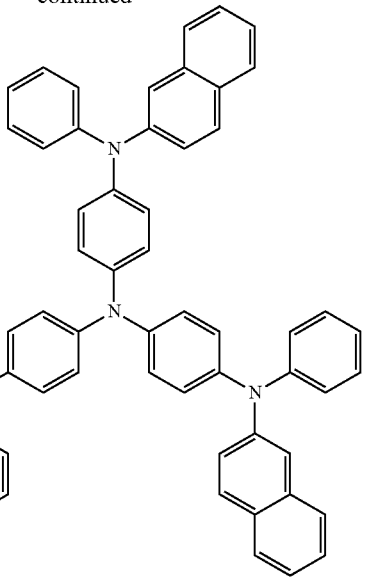

2-TNATA

A thickness of the HIL may be in a range of about 100 Å to about 10,000 Å, e.g., about 100 Å to about 1,000 Å. When the thickness of the HIL is within the range described above, the HIL may have satisfactory hole injection characteristics without a substantial increase in a driving voltage.

Then, a hole transport layer (HTL) may be formed on the HIL by using, e.g., vacuum deposition, spin coating, casting, Langmuir-Blodgett (LB) deposition, or the like. When the HTL is formed using vacuum deposition or spin coating, the deposition and coating conditions may be similar to those for the formation of the HIL, though the conditions for deposition and coating may vary according to the material that is used to form the HTL.

The hole-transportation material may include, e.g., a carbazole derivative, such as N-phenylcarbazole or polyvinylcarbazol, N,N-bis(3-methylphenyl)-N,N-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB).

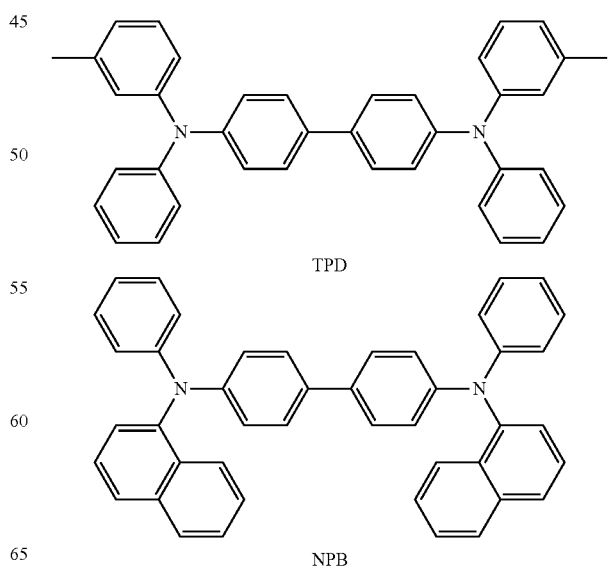

TPD

NPB

A thickness of the HTL may be in a range of about 50 Å to about 2,000 Å, e.g., about 100 Å to about 1,500 Å. When the thickness of the HTL is within the ranges described above, the HTL may have satisfactory hole transportation properties without a substantial increase in a driving voltage.

A H-functional layer (a functional layer having a hole injection ability and a hole transport ability) may include one or more materials selected from the materials for the HIL and the materials for the HTL. A thickness of the H-functional layer may be in a range of about 500 Å to about 10,000 Å, e.g., about 100 Å to about 1,000 Å. When the thickness of the H-functional layer is within the range described above, satisfactory hole injection and transportation properties may be obtained without a substantial increase in driving voltage.

In addition, at least one layer of the HIL, the HTL, and the H-functional layer may include at least one of a compound represented by Formula 300, below, or a compound represented by Formula 350, below:

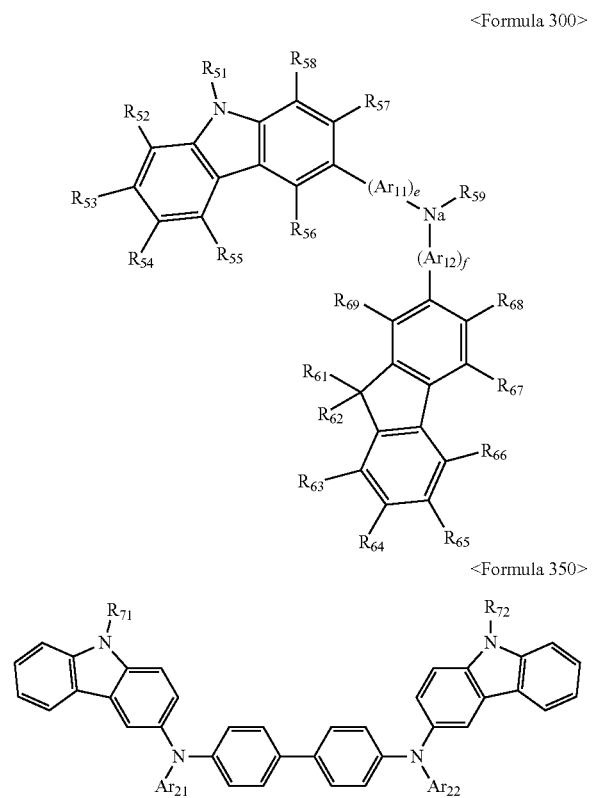

<Formula 300>

<Formula 350>

In Formulae 300 and 350, $Ar_{11}$, $Ar_{12}$, $Ar_{21}$, and $Ar_{22}$ may each independently be a substituted or unsubstituted $C_5$-$C_{60}$ arylene group.

e and f in Formula 300 may each independently be an integer of 0 to 5, or 0, 1 or 2. For example, e may be 1 and f may be 0.

$R_{51}$ to $R_{58}$, $R_{61}$ to $R_{69}$, and $R_{71}$ and $R_{72}$ in Formulae 300 and 350 may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryoxyl group, or a substituted or unsubstituted $C_5$-$C_{60}$ arylthio group. For example, $R_{51}$ to $R_{58}$, $R_{61}$ to $R_{69}$, $R_{71}$ and $R_{72}$ may each independently be selected from a hydrogen atom; a deuterium atom; a halogen atom; a hydroxyl group; a cyano group; a nitro group; an amino group; an amidino group; a hydrazine group; a hydrazone group; a carboxyl group or a salt thereof; a sulfonic acid or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof and a phosphoric acid or a salt thereof; a phenyl group; a naphthyl group; an anthryl group; a fluorenyl group; a pyrenyl group; or a phenyl group, a naphthyl group, an anthryl group, a fluorenyl group, and a pyrenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group.

$R_{59}$ in Formula 300 may be selected from a phenyl group; a naphthyl group; an anthryl group; a biphenyl group; and a pyridyl group; or a phenyl group, a naphthyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

In an implementation, the compound represented by Formula 300 may be represented by Formula 300 A.

<Formula 300A>

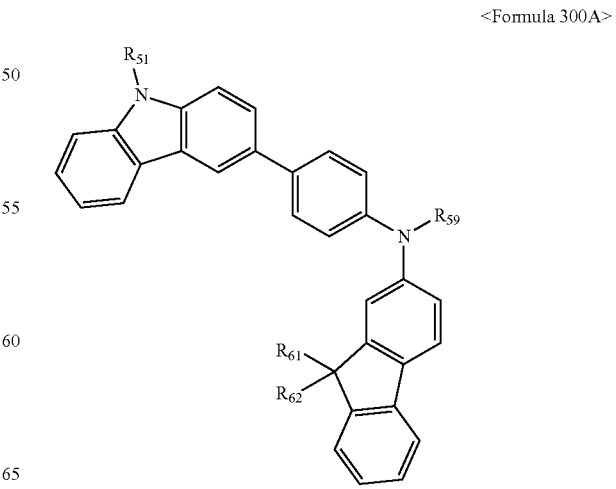

$R_{51}$, $R_{61}$, $R_{62}$, and $R_{59}$ in Formula 300A may be the same as those described above.
In an implementation, at least one layer of the HIL, the HTL, and the H-functional layer may include at least one of Compounds 301 to 320 below.
301
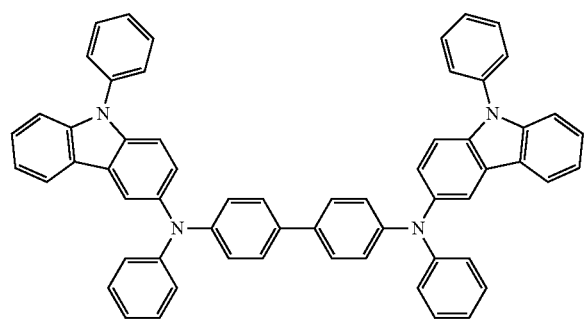
302
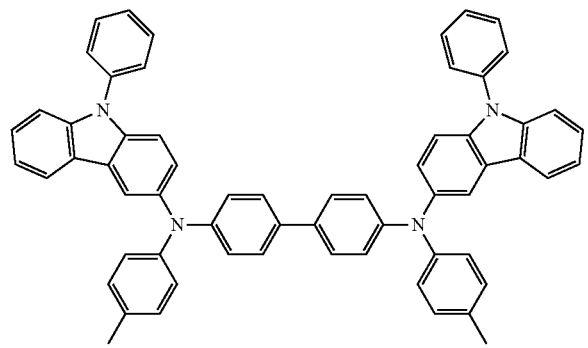
303
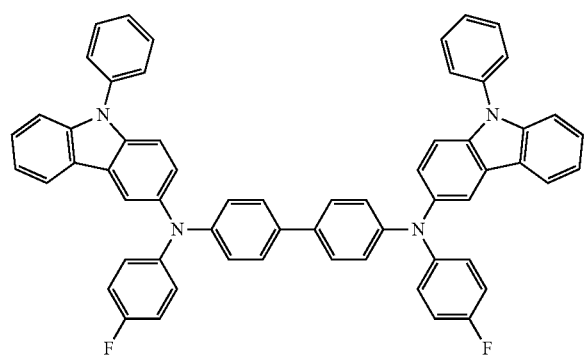
304
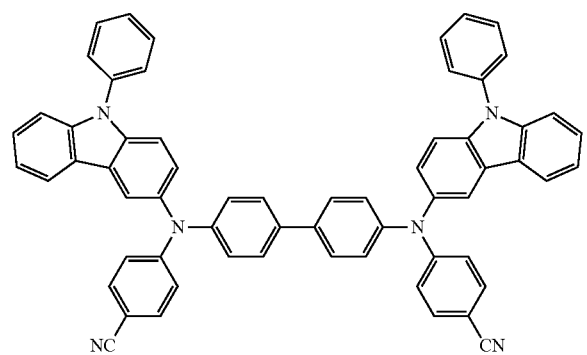
-continued
305
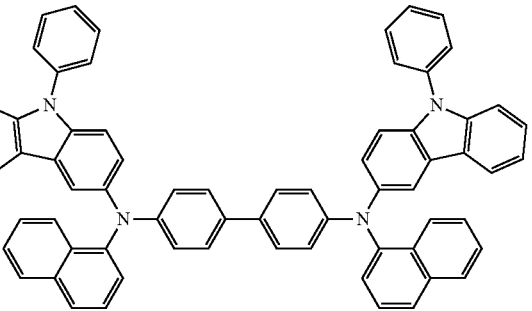
306
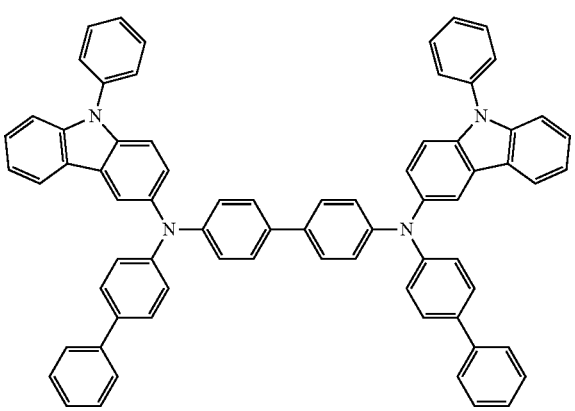
307
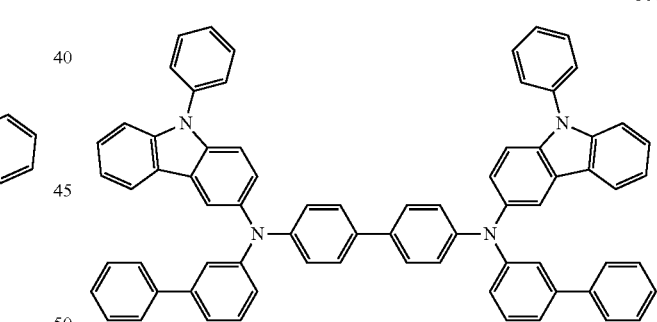
308
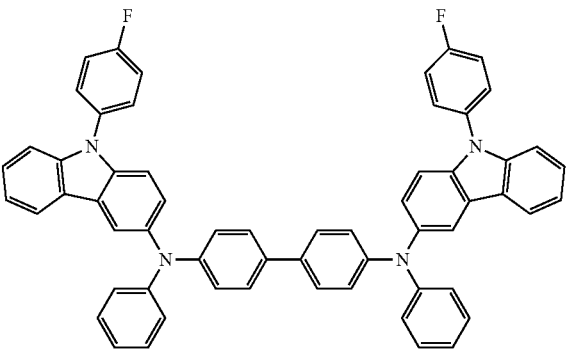

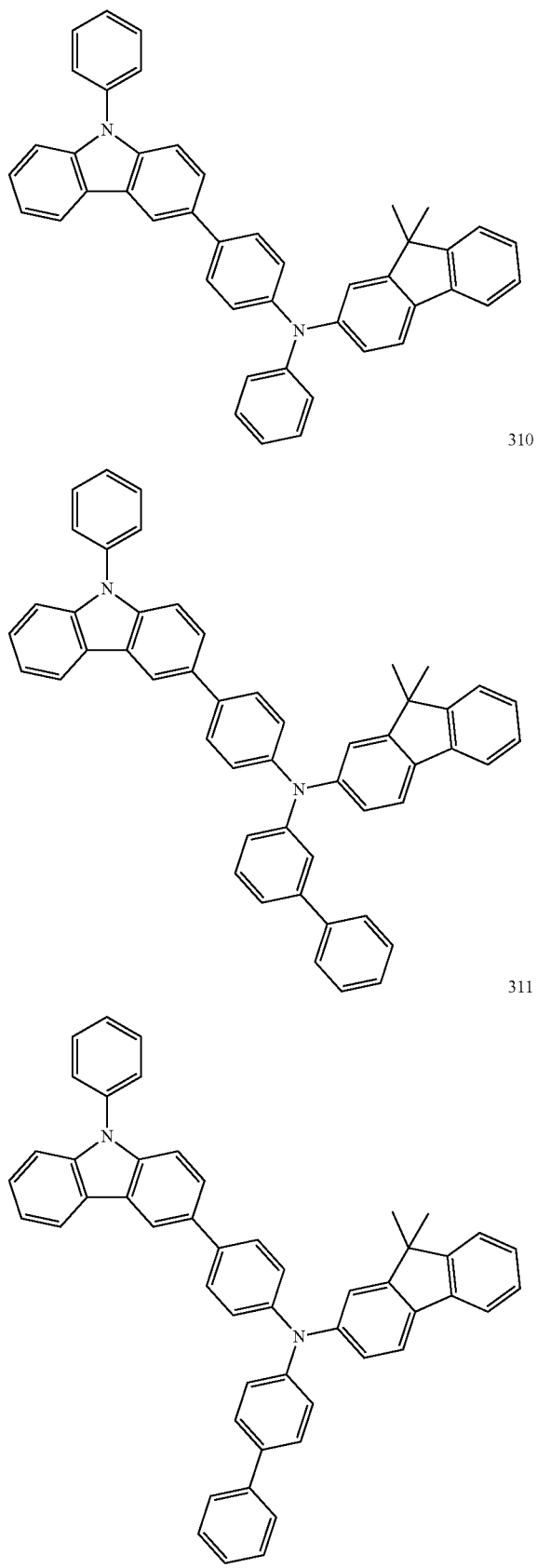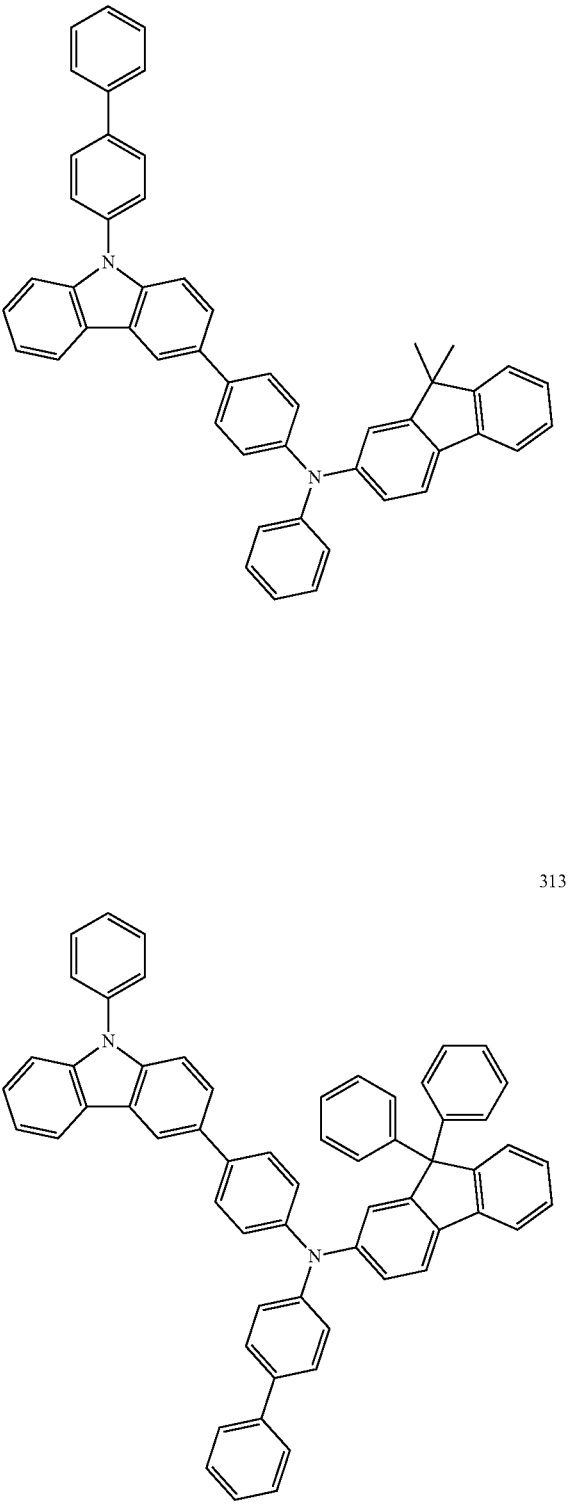

314
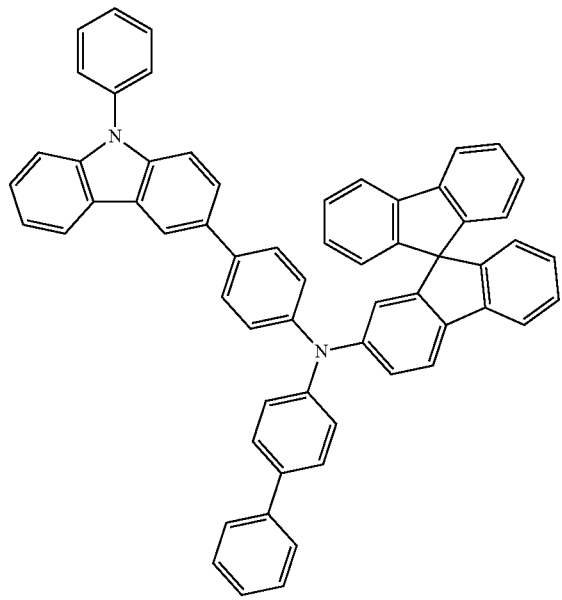
315
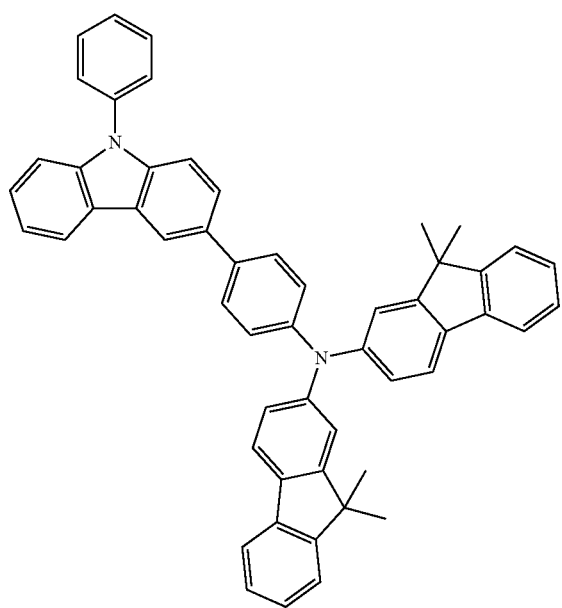
316
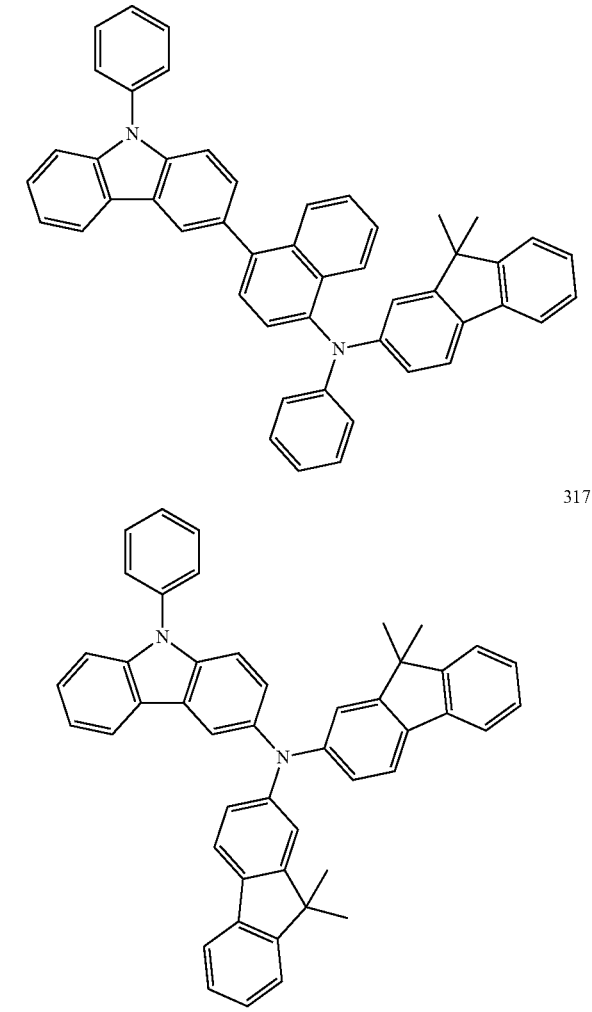
317
318
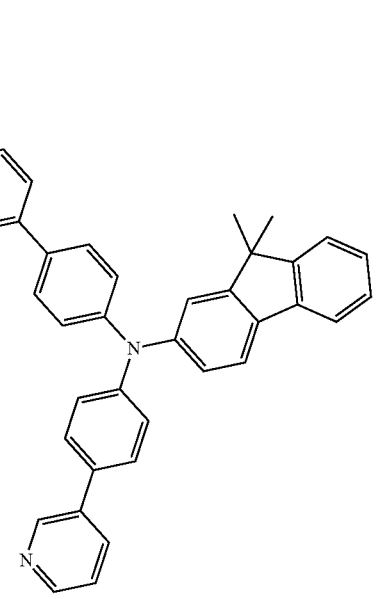

-continued

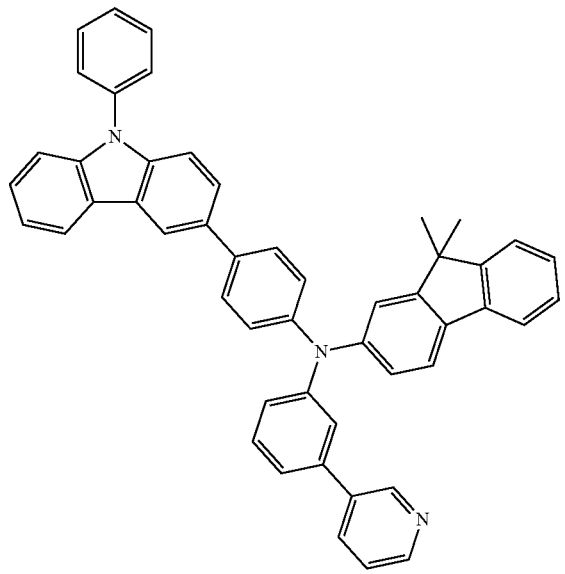

319

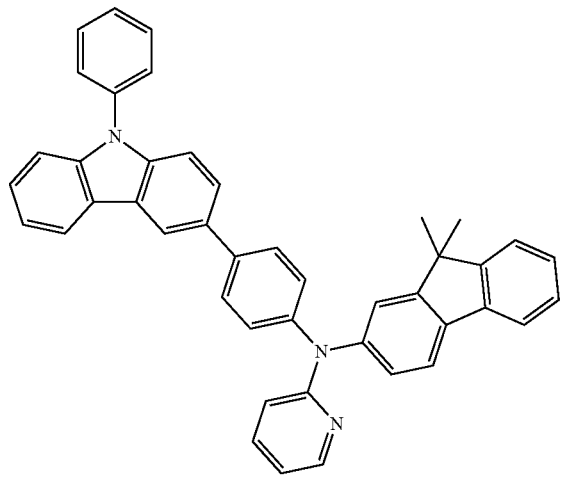

320

At least one of the HIL, the HTL, and the H-functional layer may further include a charge-generation material to increase conductivity of a layer, in addition to other hole injecting materials, hole transport materials, and/or materials having both hole injection and hole transport capabilities.

The charge-generation material may be, e.g., a p-dopant. The p-dopant may be one of a quinone derivative, a metal oxide, or a cyano group-containing compound. Examples of the p-dopant may include a quinone derivative, such as tetracyanoquinonedimethein (TCNQ) and 2,3,5,6-tetrafluoro-tetracyano-1,4-benzoquinonedimethein (F4-TCNQ), or the like; a metal oxide, such as a tungsten oxide and a molybdenum oxide; and a cyano group-containing compound, such as Compound 200 below.

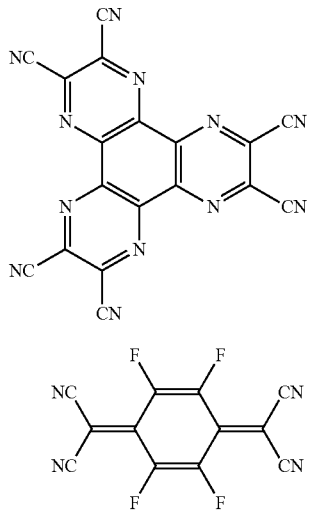

<Compound 200>

<F4-TCNQ>

When the HIL, the HTL, or the H-functional layer further includes a charge-generation material, the charge-generation material may be homogeneously dispersed or non-homogeneously distributed in the HIL, the HTL, and/or the H-functional layer.

A buffer layer may be disposed between at least one of the HIL, the HTL, and the H-functional layer, and an emission layer. The buffer layer may help compensate for an optical resonance distance of light according to a wavelength of the light emitted from the emission layer, and thus may increase efficiency. The buffer layer may include a suitable hole injecting material or hole transporting material. In an implementation, the buffer layer may include the same material as one of the materials included in the HIL, the HTL, and the H-functional layer that are disposed under the buffer layer.

Subsequently, an emission layer (EML) may be formed on the HTL, the H-functional layer, or the buffer layer by, e.g., spin coating, casting, or a LB method. When the EML is formed by vacuum deposition or spin coating, the deposition and coating conditions may be similar to those for the formation of the HIL, though the conditions for deposition and coating may vary according to the material that is used to form the EML.

The EML may be formed by using the compound according to an embodiment or hosts and dopants. A dopant for use in the EML may be a suitable fluorescent dopant or a suitable phosphorescent dopant.

Examples of the host may include $Alg_3$, 4,4'-N,N'-dicarbazole-biphenyl (CBP), poly(n-vinylcarbazole)(PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (see the following chemical structure), Compounds 501 to 509 illustrated below, or the like.

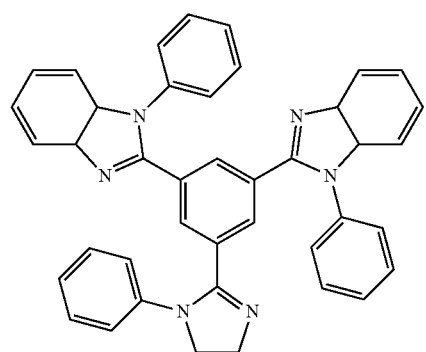
TPBI
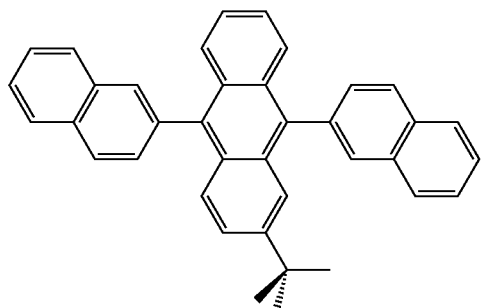
TBADN
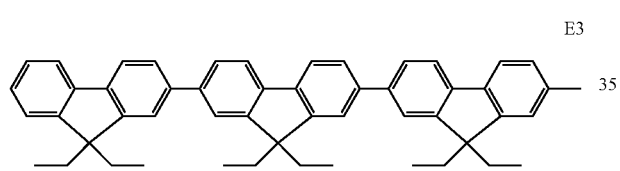
E3
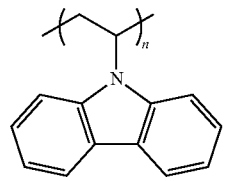
PVK
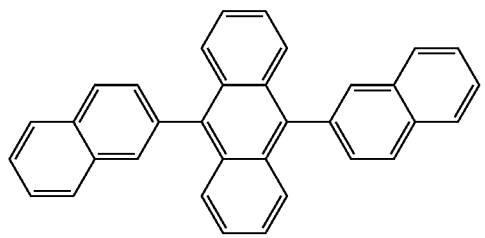
ADN
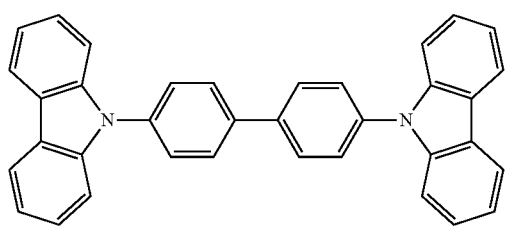
CBP
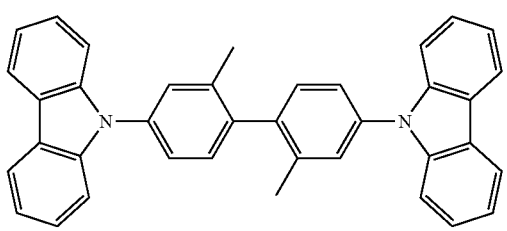
dmCBP
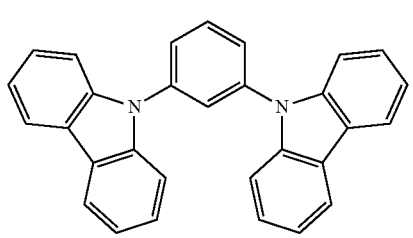
501
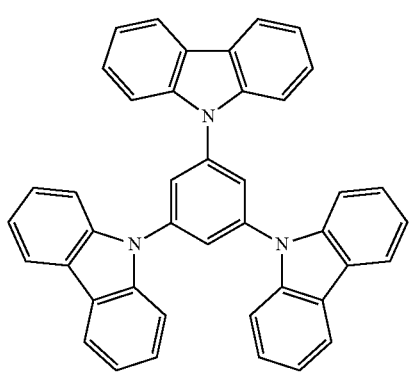
502
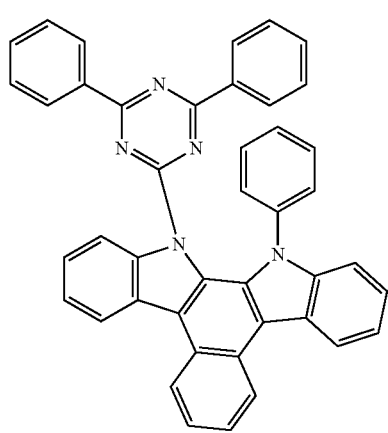
503

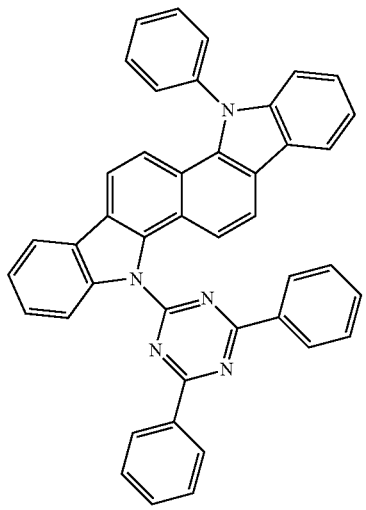
504
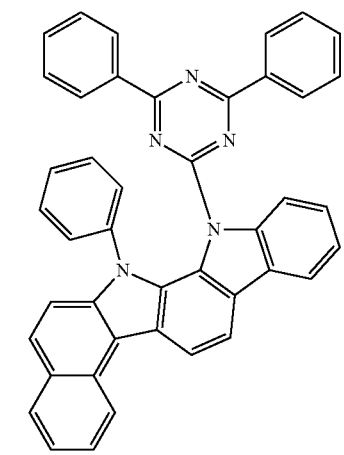
505
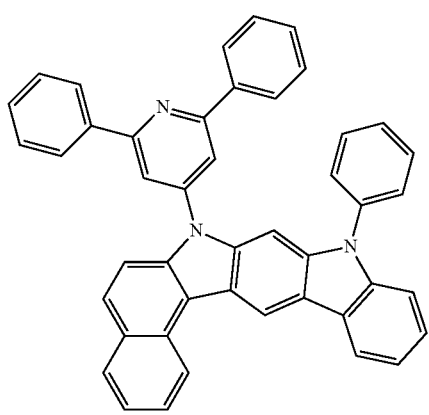
506
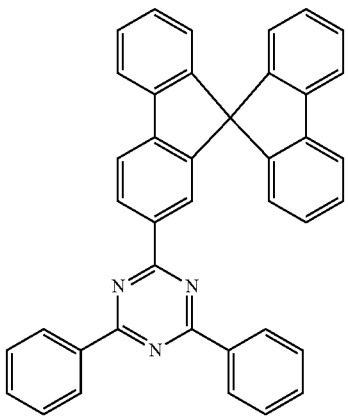
507
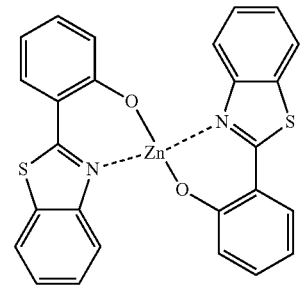
508
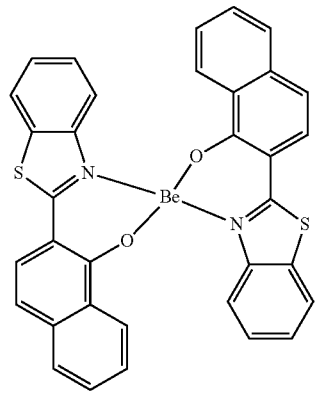
509
In an implementation, the host may be an anthracene-based compound represented by Formula 400, below.
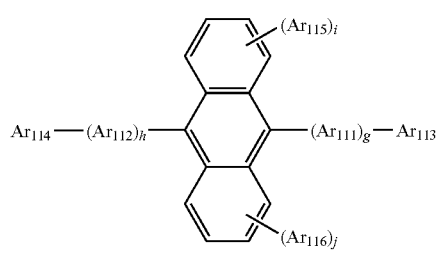
<Formula 400>
In Formula 400, $Ar_{111}$ and $Ar_{112}$ may each independently be a substituted or unsubstituted $C_5$-$C_{60}$ arylene group; $Ar_{113}$ to $Ar_{116}$ may each independently be a substituted or unsubstituted $C_1$-$C_{10}$ alkyl group, or a substituted or unsubstituted $C_5$-$C_{60}$ aryl group; and g, h, I, and j may each independently be an integer of 0 to 4.

For example, $Ar_{111}$ and $Ar_{112}$ in Formula 400 may each independently be a phenylene group, a naphthylene group, a phenanthrenyl group, or a pyrenylene group; or a phenylene group, a naphthylene group, a phenanthrenyl group, a fluorenyl group, or a pyrenylene group, each substituted with at least one of a phenyl group, a naphthyl group, and an anthryl group.

g, h, i, and j in Formula 400 may each independently be 0, 1, or 2.

$Ar_{113}$ to $Ar_{116}$ in Formula 400 may each independently be a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; or a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine group, a hydrazone group, a carboxyl group or salt thereof, a sulfonic group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, pyrenyl group, a phenanthrenyl group, a fluorenyl group; or

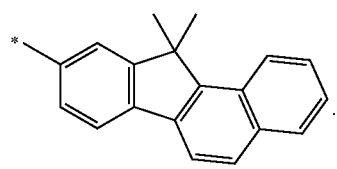 [SMILES: Cc1ccc2c(c1)C(C)(C)c1c-2ccc2ccccc12]

For example, the anthracene-based compound represented by Formula 400 may be one of the following compounds.

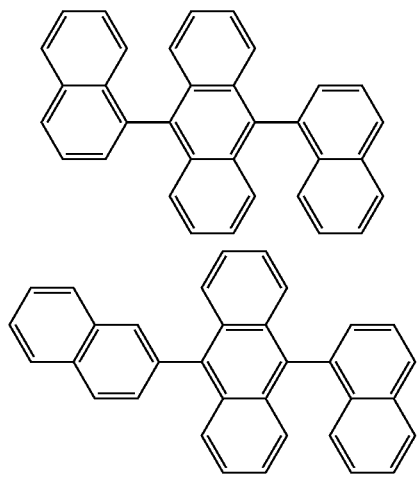

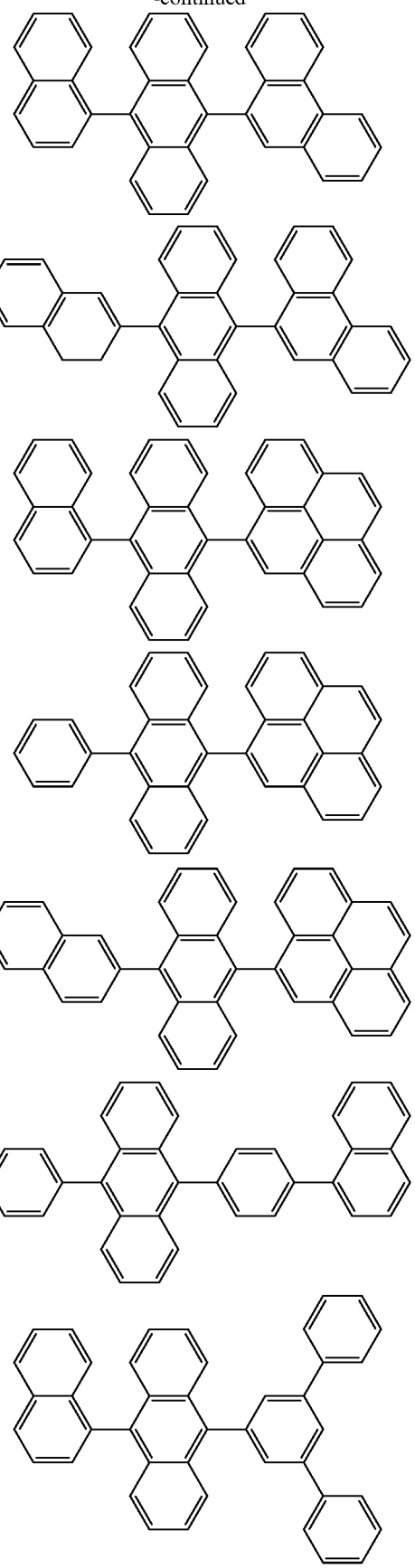

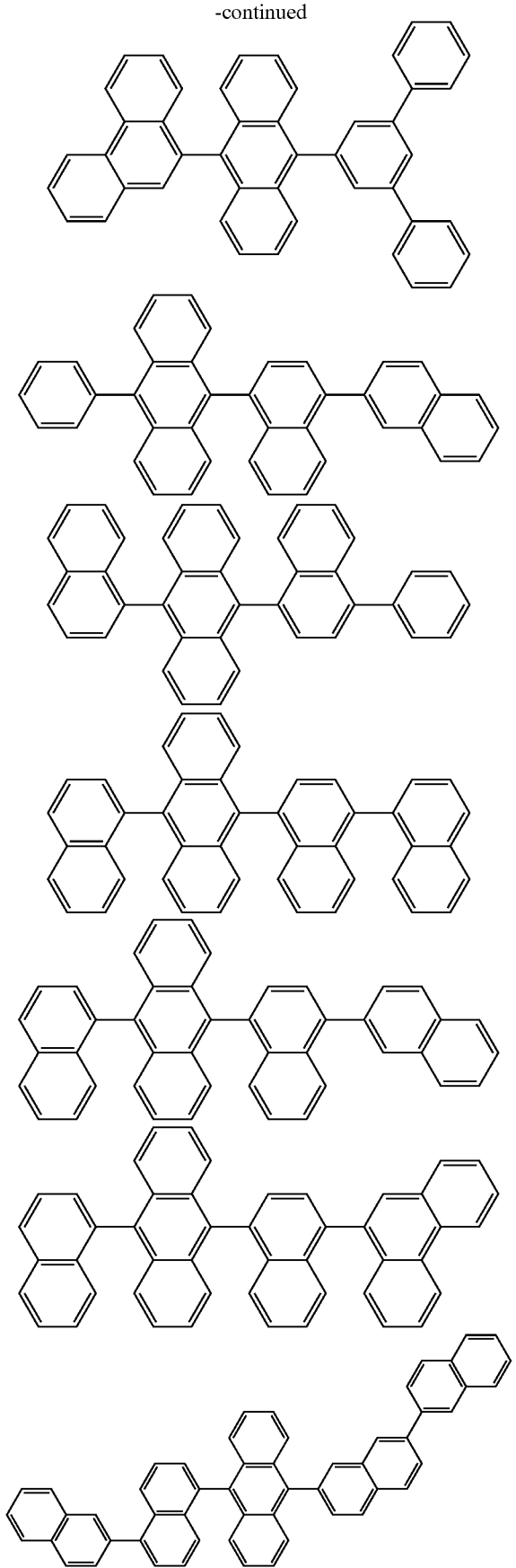
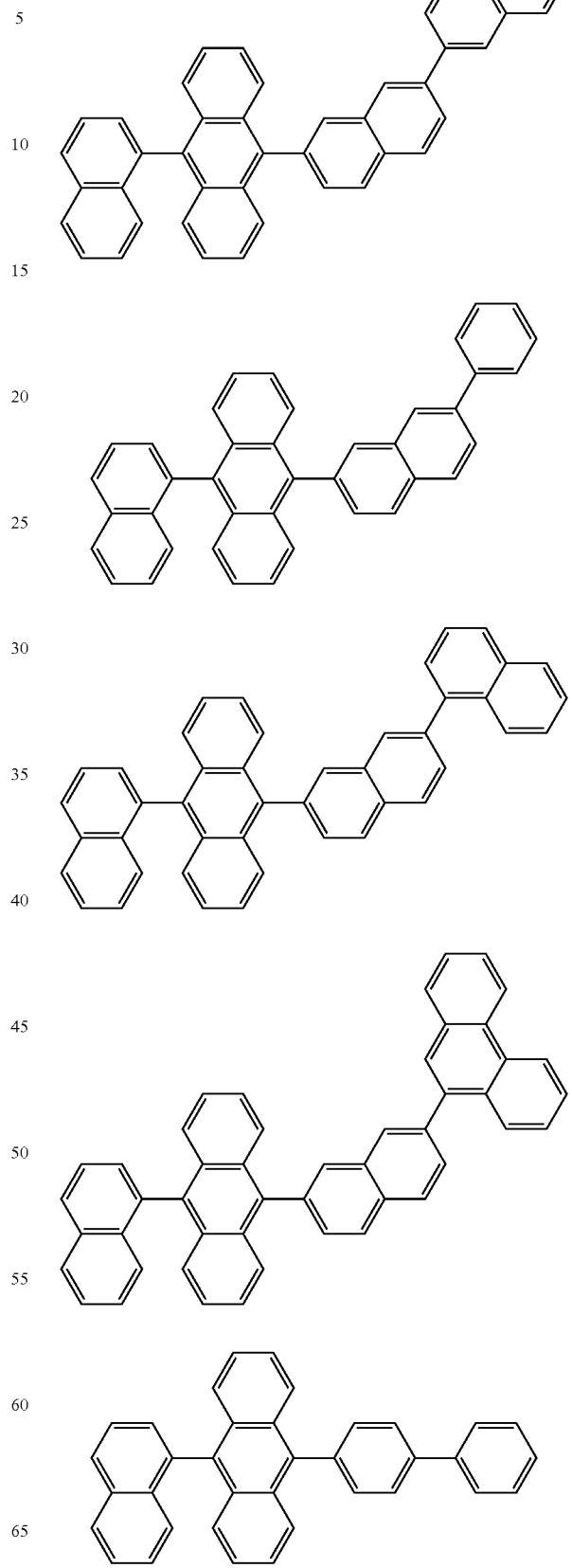

-continued
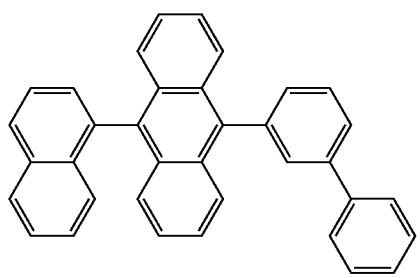
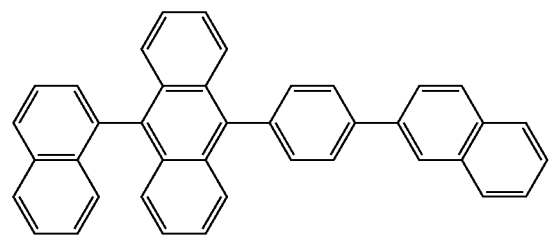
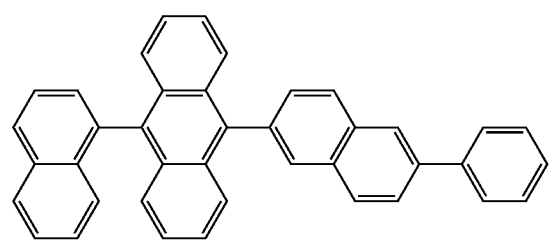
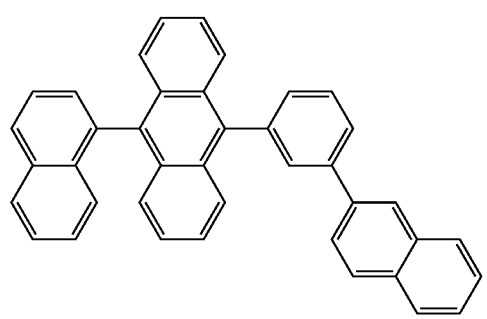
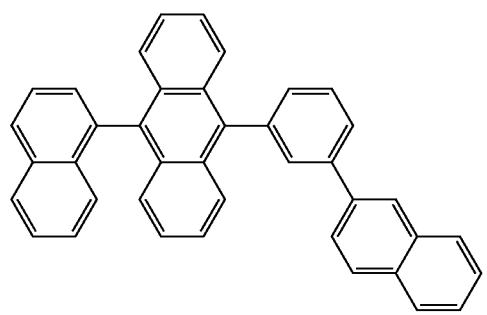
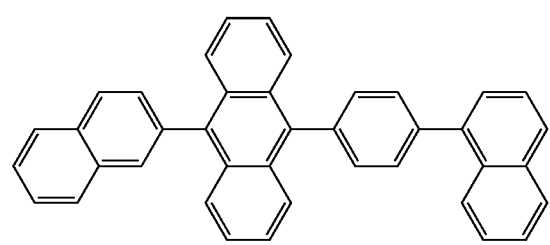
-continued
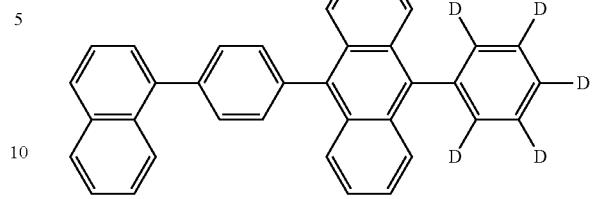
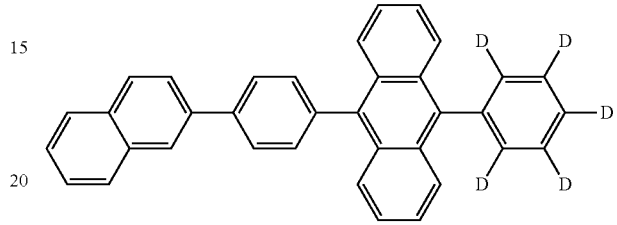
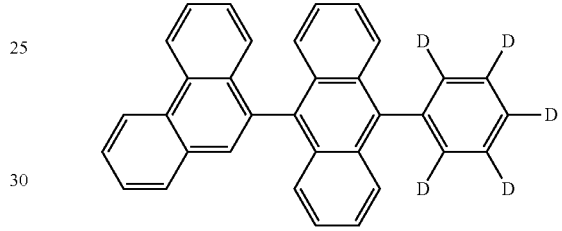
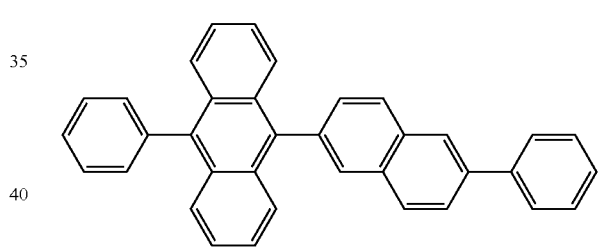
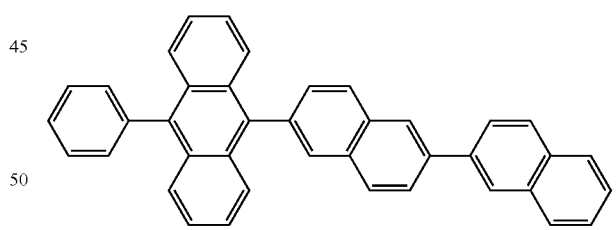
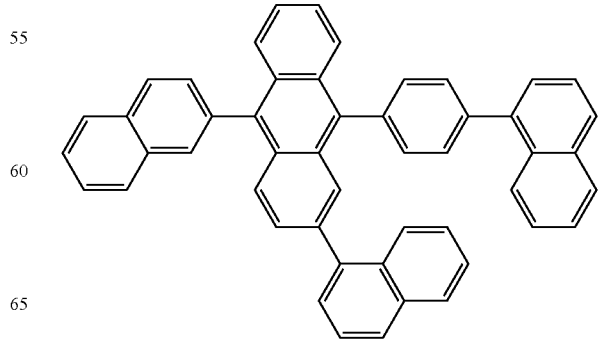

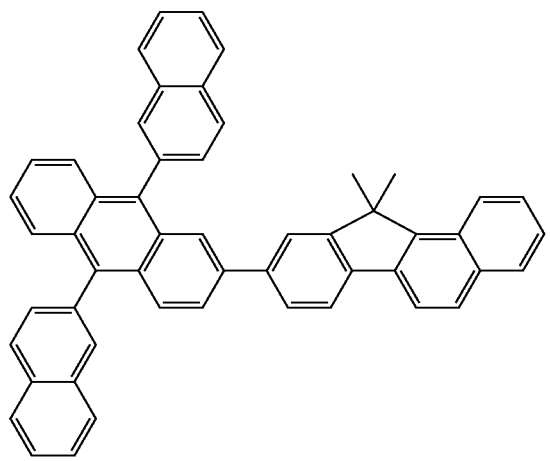

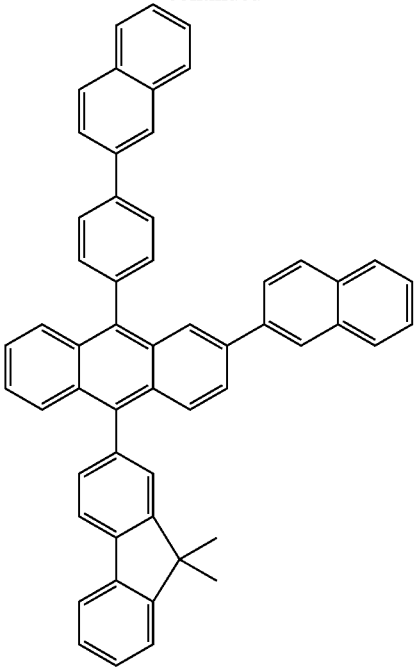

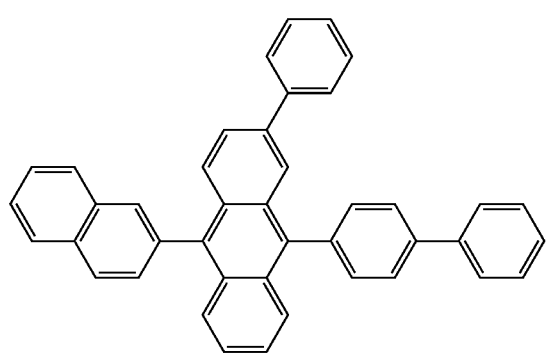

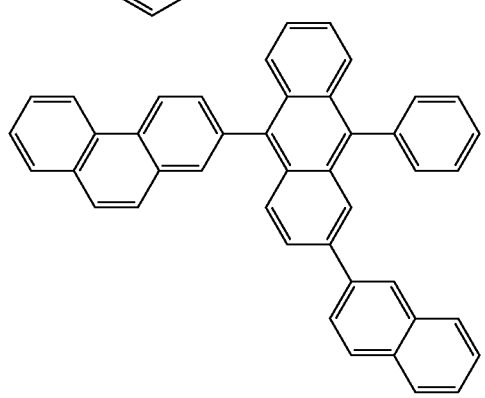

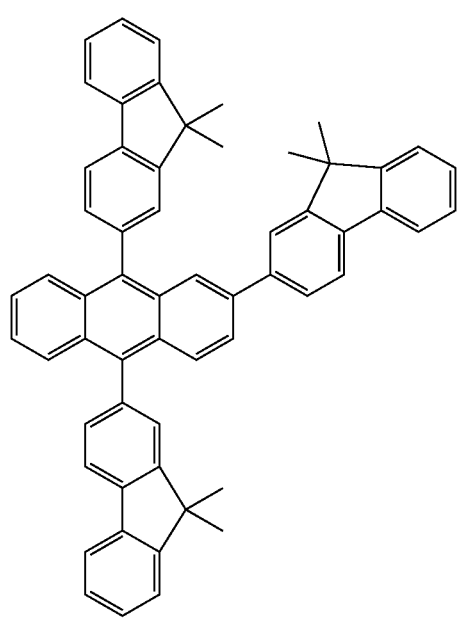

In an implementation, the host may be an anthracene-based compound represented by Formula 401, below.

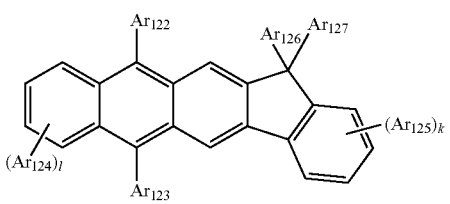

<Formula 401>

$Ar_{122}$ to $Ar_{125}$ in Formula 401 may be the same as those described in detail in connection with $Ar_{113}$ in Formula 400.

$Ar_{126}$ and $Ar_{127}$ in Formula 401 may each independently be a $C_1$-$C_{10}$ alkyl group (e.g., a methyl group, an ethyl group, or a propyl group).

k and l in Formula 401 may each independently be an integer of 0 to 4. For example, k and l may be 0, 1, or 2.

In an implementation, the anthracene-based compound represented by Formula 401 may be one of the following compounds.

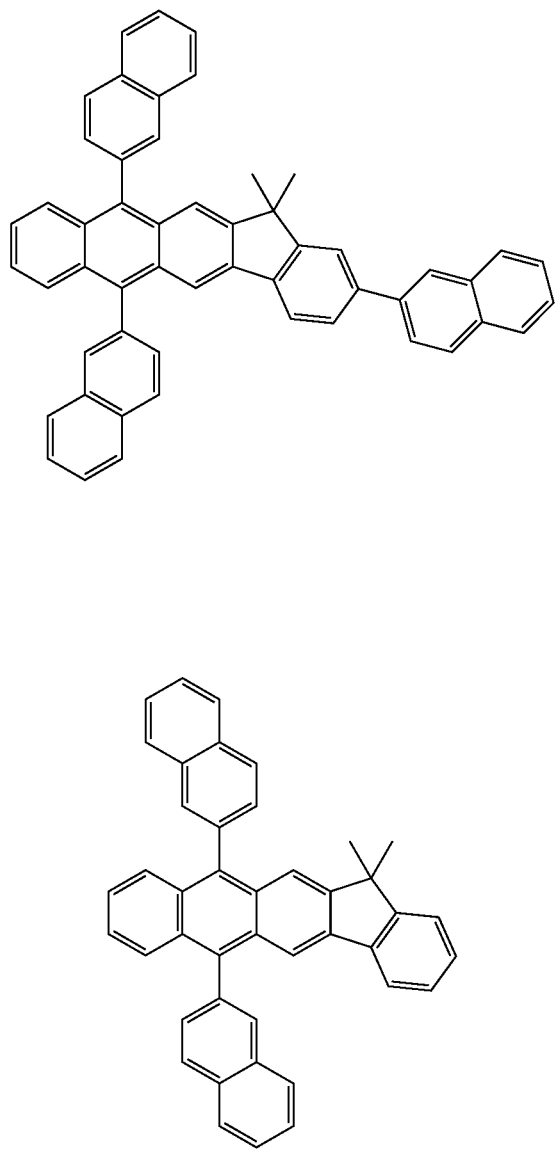
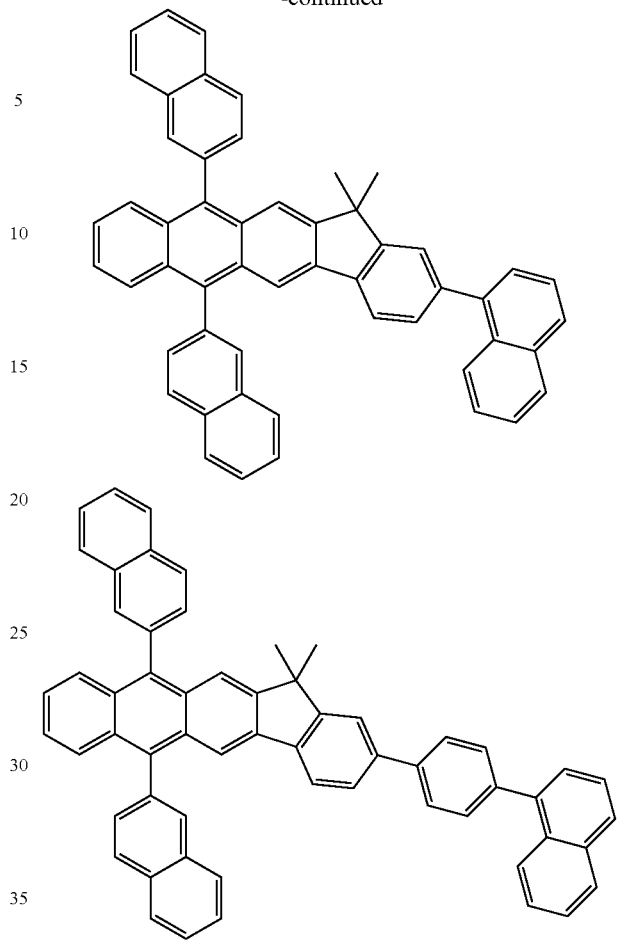
When the organic light-emitting device is a full color organic light-emitting device, the EML may be patterned into a red EML, a green EML, and a blue EML.
In an implementation, at least one of the red EML, the green EML, and the blue EML may include the following dopants (ppy=phenylpyridine)
For example, compounds illustrated below may be used as a blue dopant.
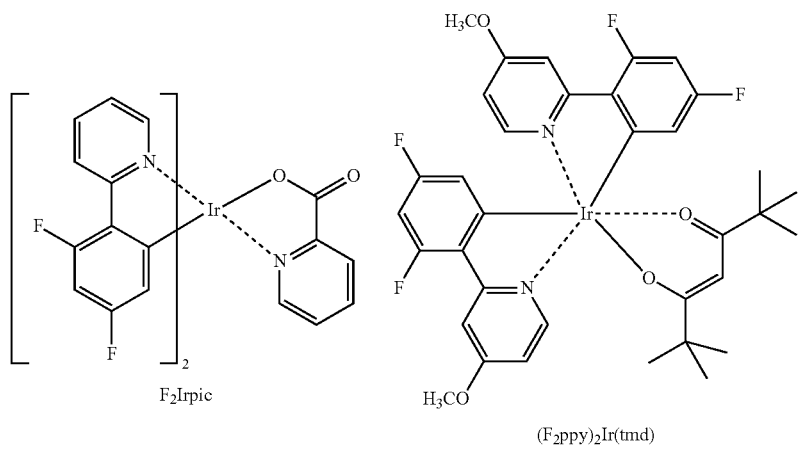

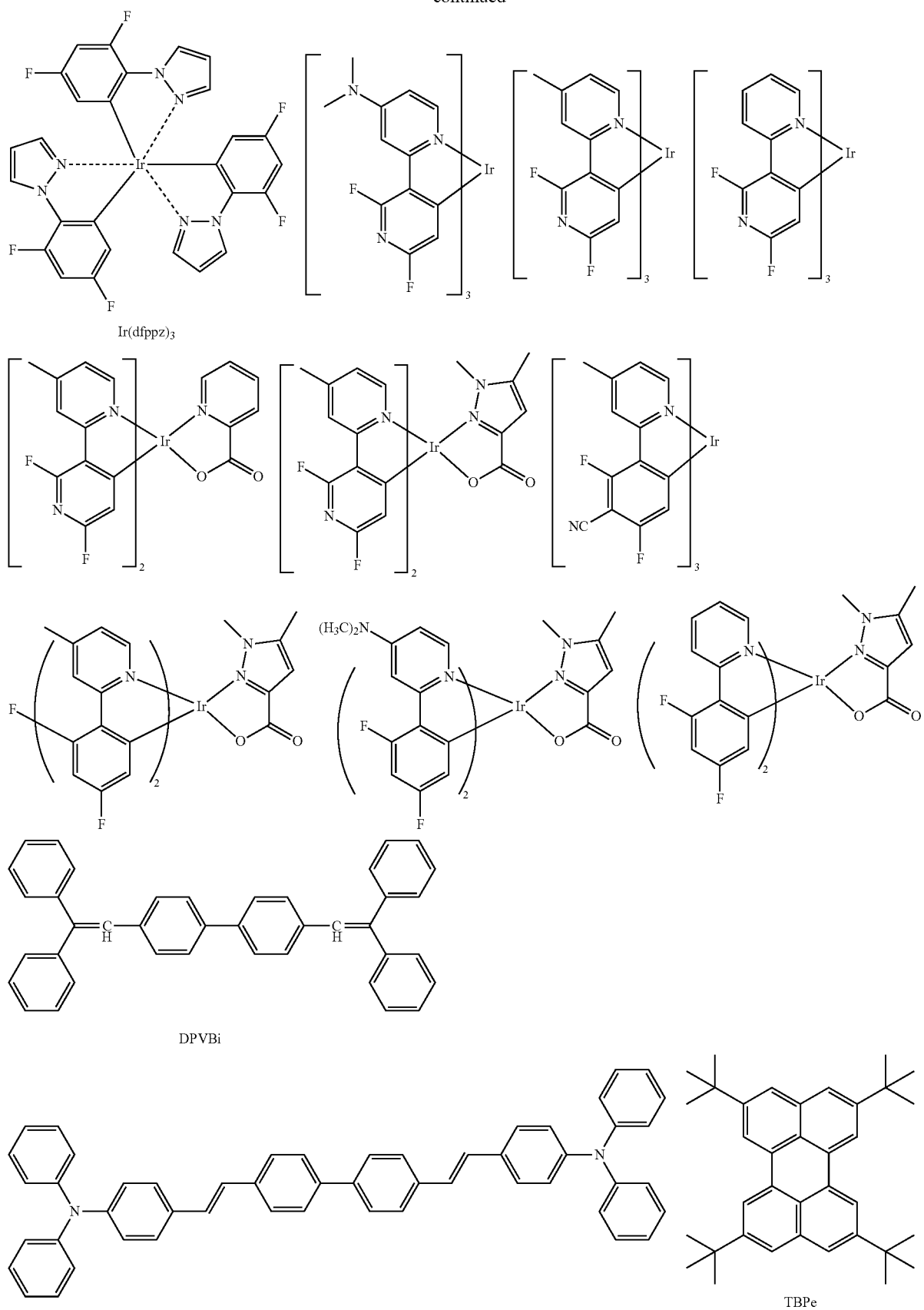

For example, compounds illustrated below may be used as a red dopant.
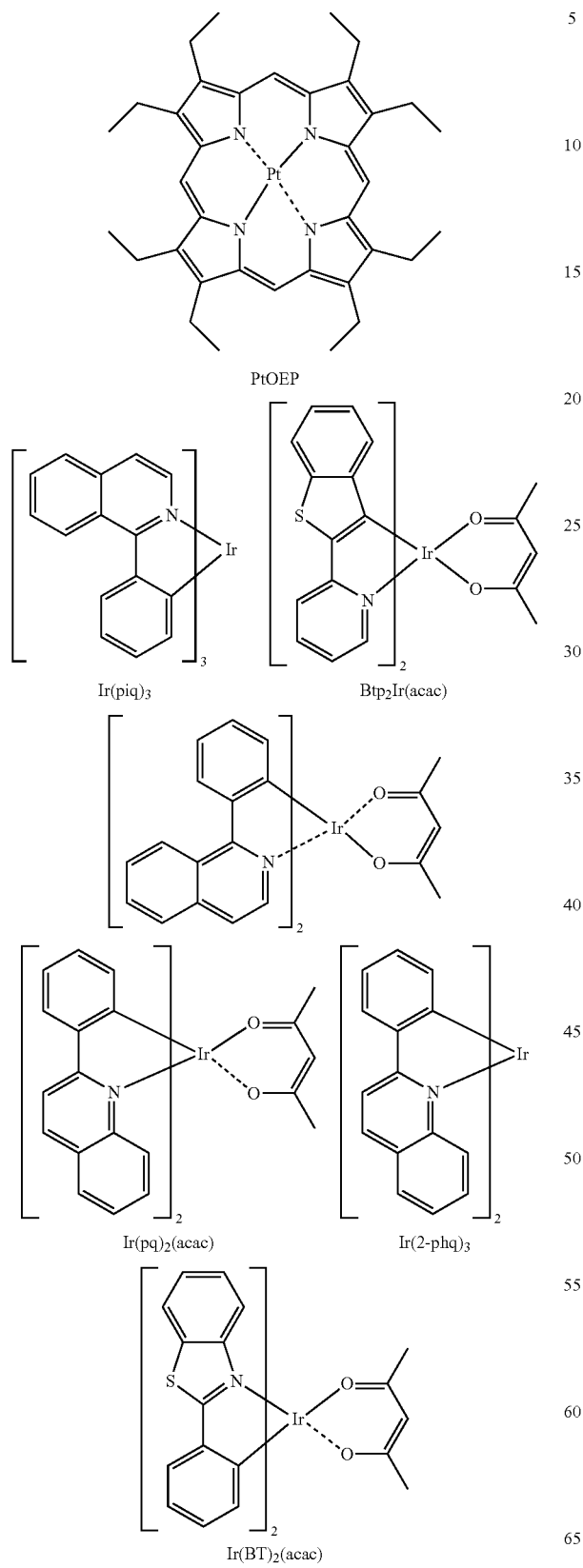
-continued
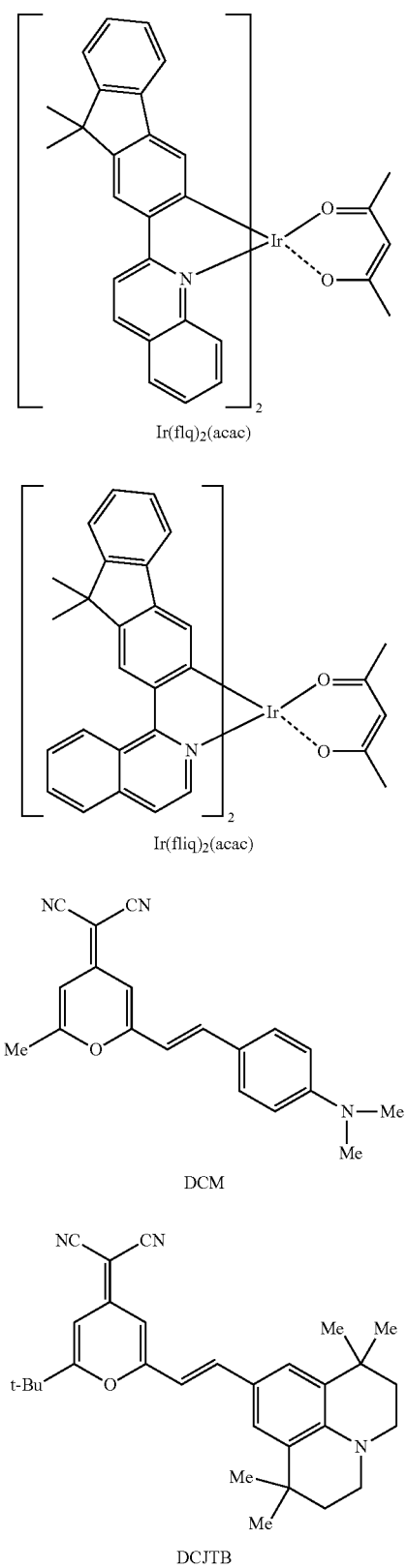
For example, compounds illustrated below may be used as a green dopant.

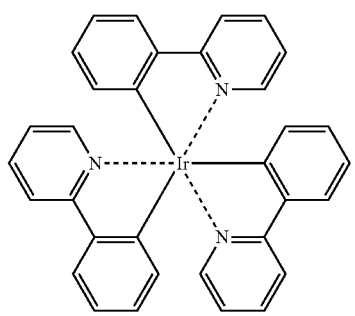
Ir(ppy)₃
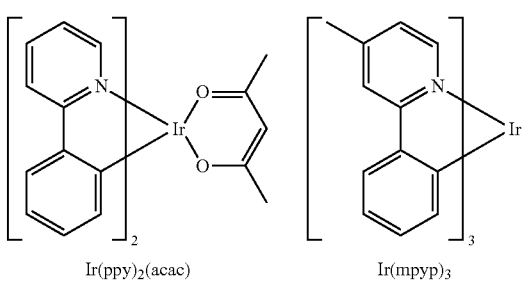
Ir(ppy)₂(acac)  Ir(mpyp)₃
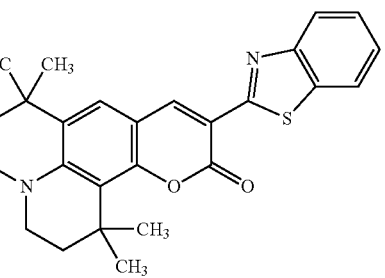
C545T
Another example of the dopant included in the EML may include a Pd-complex or a Pt-complex, (e.g., D1-D50) below.
D1
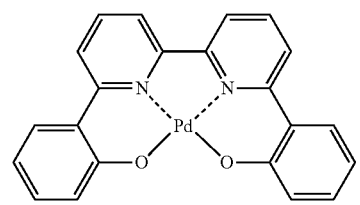
D2
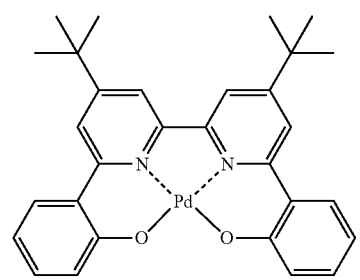
-continued
D3
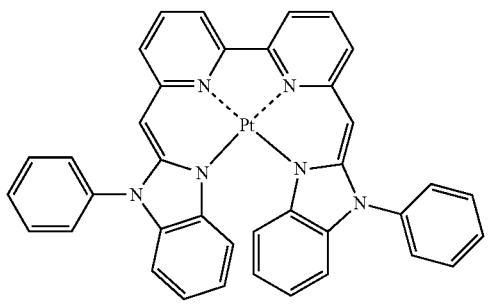
D4
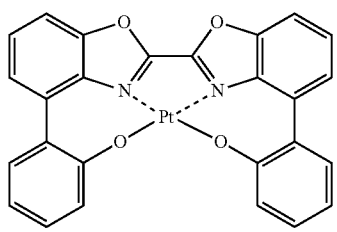
D5
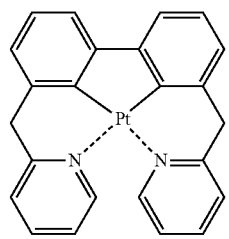
D6
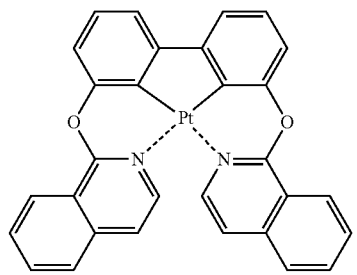
D7
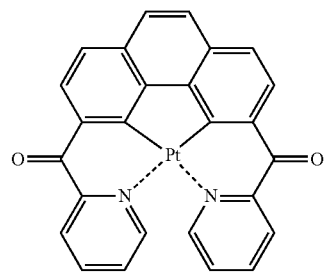
D8
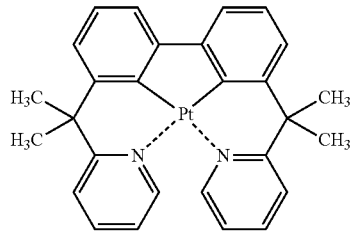

D9 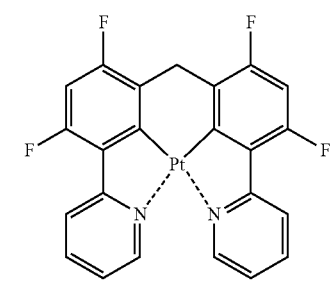
D10 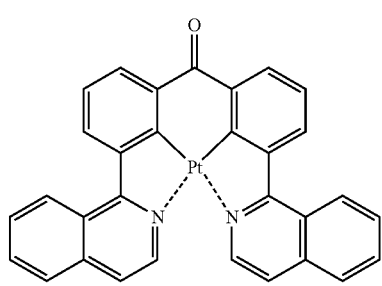
D11 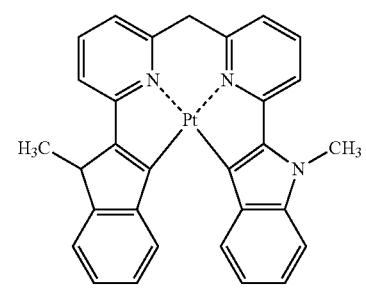
D12 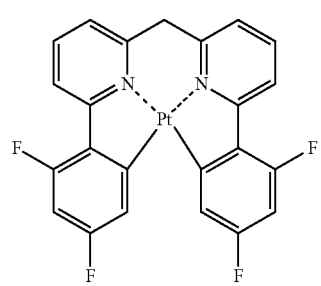
D13 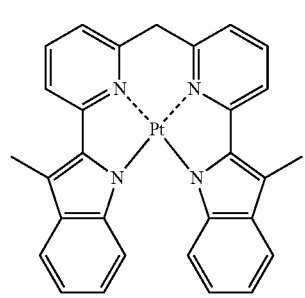
D14 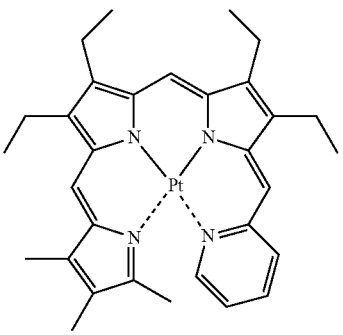
D15 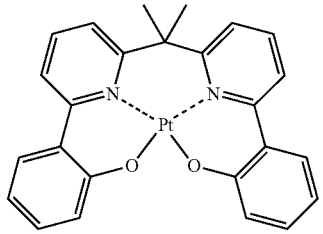
D16 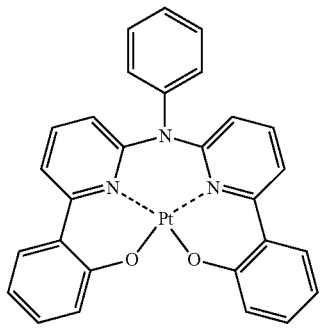
D17 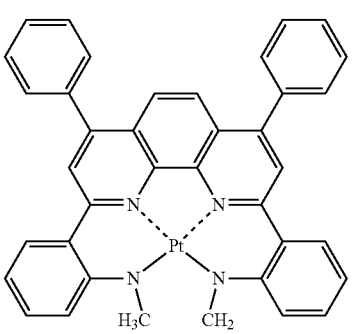
D18 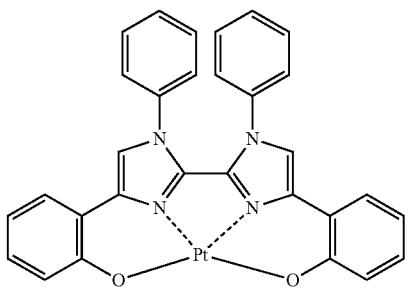

-continued
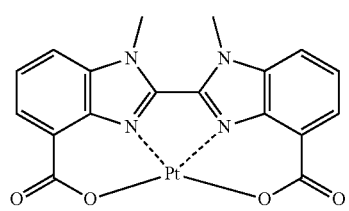
D19
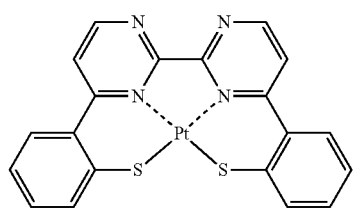
D20
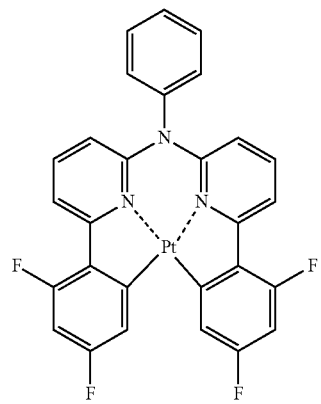
D21
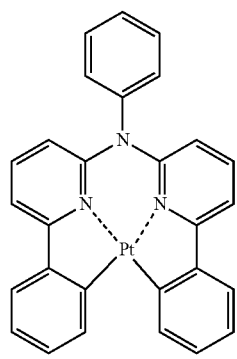
D22
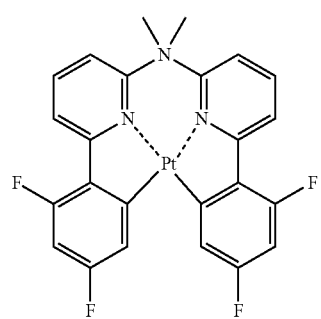
D23
-continued
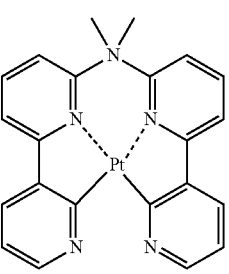
D24
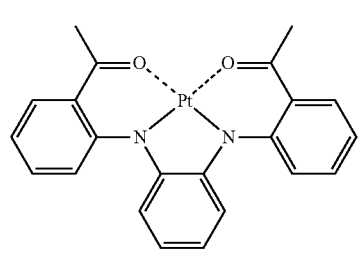
D25
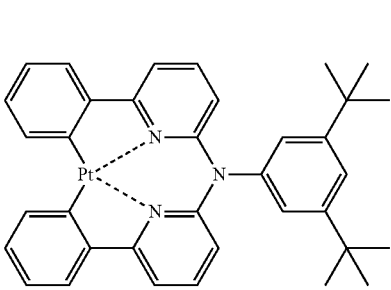
D26
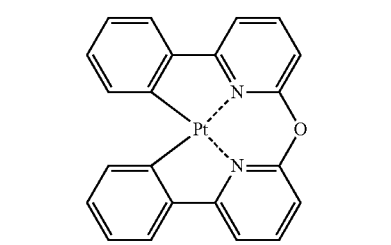
D27
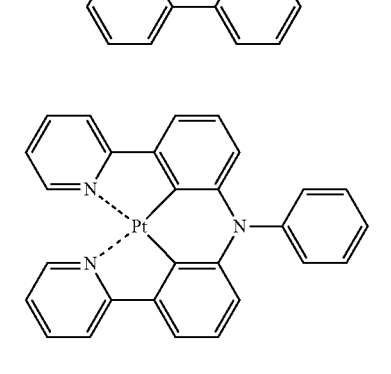
D28
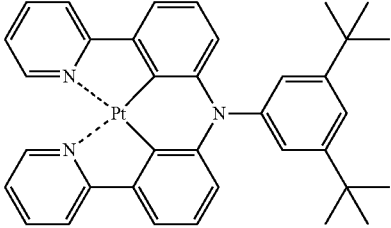
D29

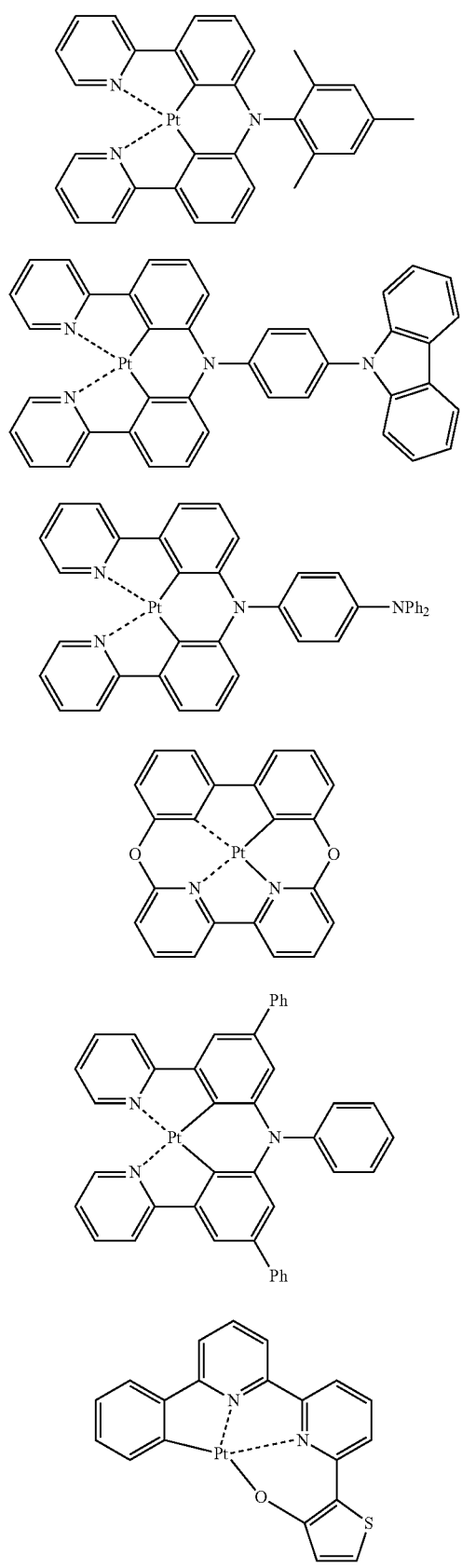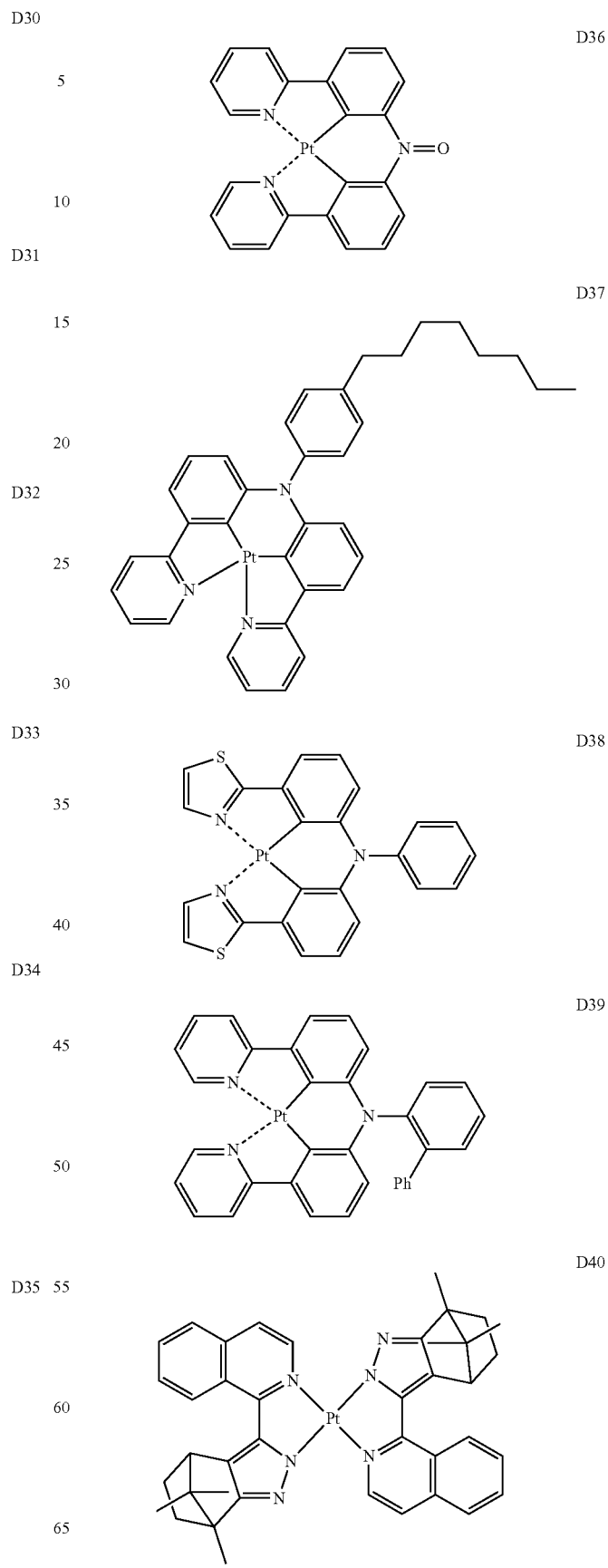

D41
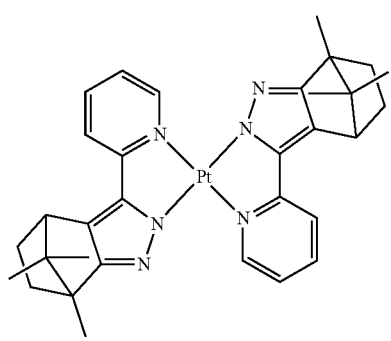
D42
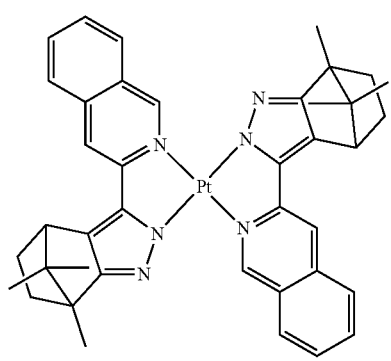
D43
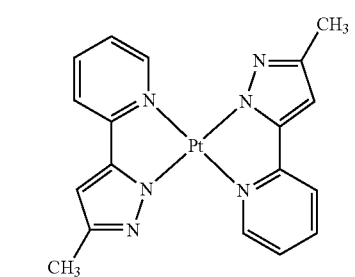
D44
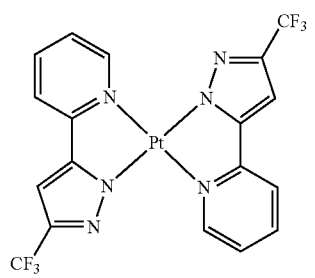
D45
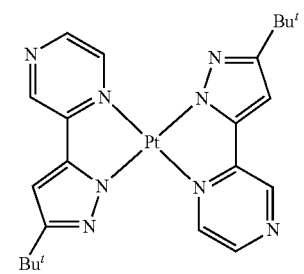
D46
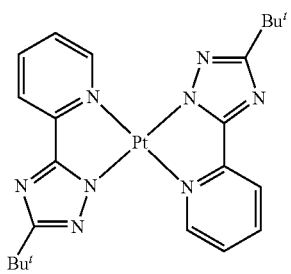
D47
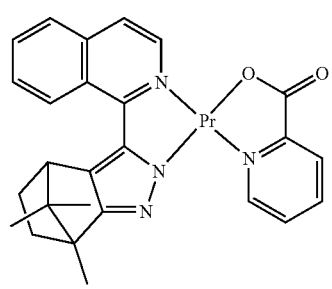
D48
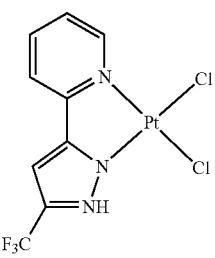
D49
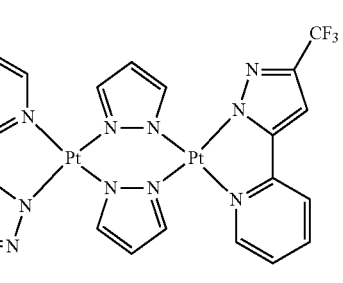
D50
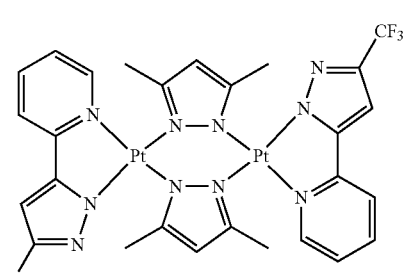
Another example of the dopant included in the EML may include a Os-complex, below.

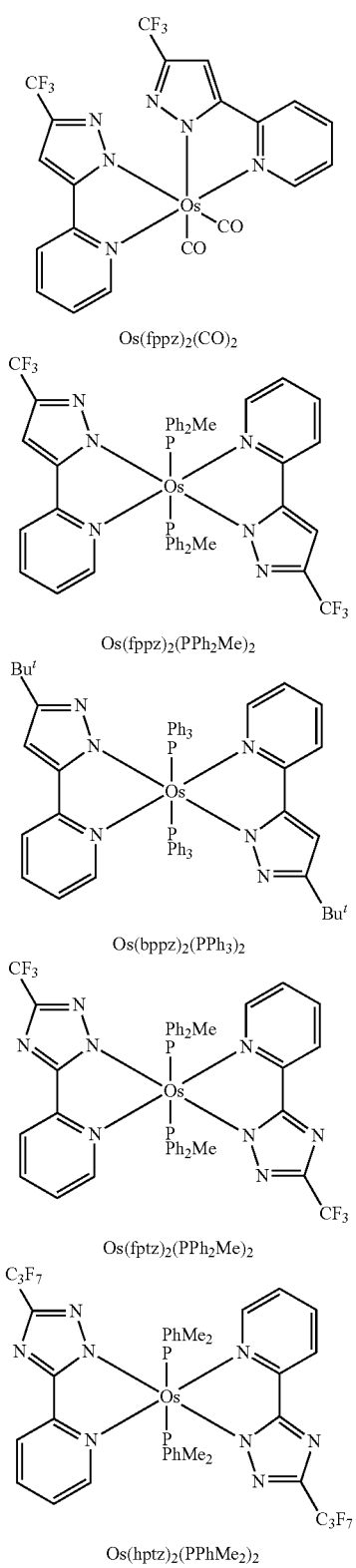

Os(fppz)₂(CO)₂

Os(fppz)₂(PPh₂Me)₂

Os(bppz)₂(PPh₃)₂

Os(fptz)₂(PPh₂Me)₂

Os(hptz)₂(PPhMe₂)₂ luminescent characteristics may be obtained without a substantial increase in driving voltage.

Next, an electron transport layer (ETL) is formed on the EML by using various methods, e.g., by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL.

A material for forming the ETL may stably transport electrons injected from an electron injection electrode (cathode), and may include a suitable electron transportation material.

Examples of a suitable electron transportation material may include a quinoline derivative, such as tris(8-quinolinolate)aluminium (Alq3), TAZ, Balq, beryllium bis(benzoquinolin-10-olate) (Bebq₂), ADN, Compound 201, and Compound 202.

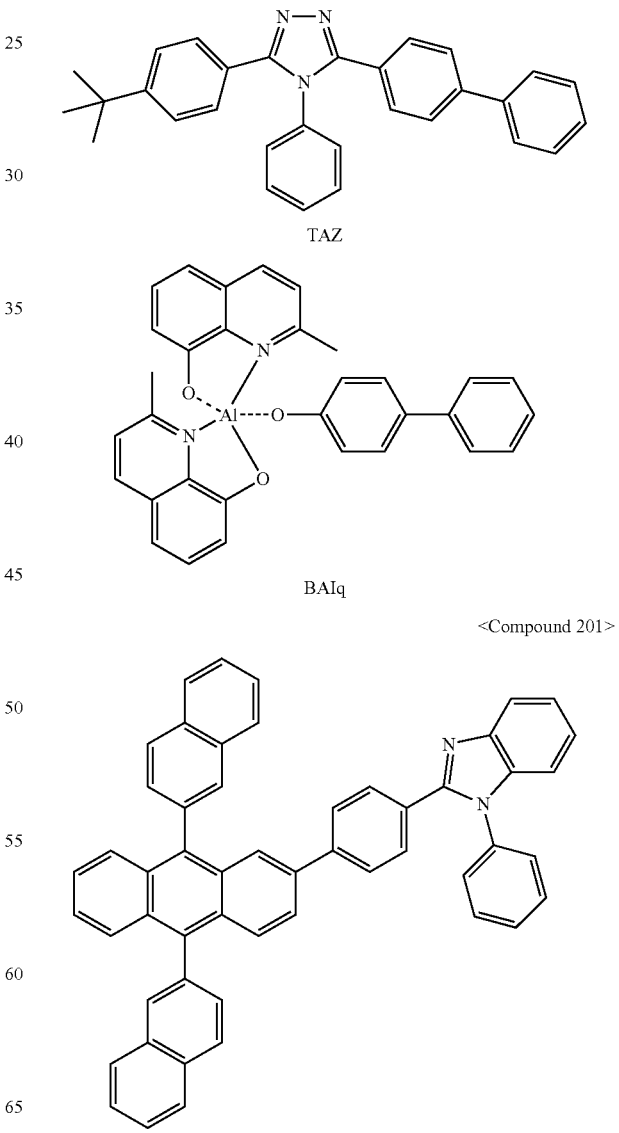

TAZ

BAlq

<Compound 201>

When the EML includes a host and a dopant, an amount of the dopant may be from about 0.01 to about 15 parts by weight, based on 100 parts by weight of the host.

A thickness of the EML may be in a range of about 100 Å to about 10,000 Å, e.g., about 200 Å to about 600 Å. If the thickness of the EML is within these ranges, excellent <Compound 202>

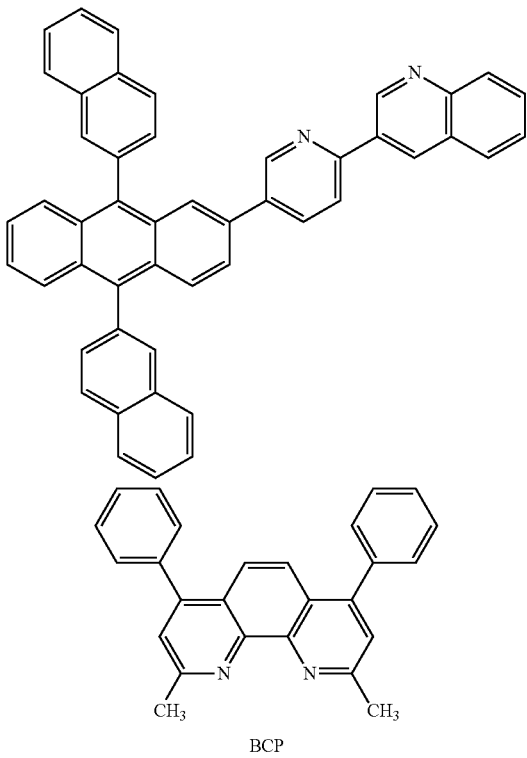

A thickness of the ETL may be in a range of about 100 Å to about 1,000 Å, e.g., about 150 Å to about 500 Å. When the thickness of the ETL is within the range described above, the ETL may have satisfactory electron transportation characteristics without a substantial increase in driving voltage.

In an implementation, the ETL may include, in addition to an electron transport organic compound, a metal-containing material.

The metal-containing material may include a lithium (Li) complex. Examples of the Li complex may include lithium quinolate (LiQ) and Compound 203 below:

<Compound 203>

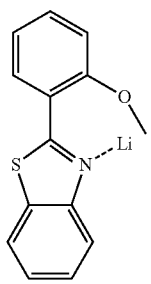

Then, an electron injection layer (EIL), which facilitates injection of electrons from the cathode, may be formed on the ETL. A suitable electron-injecting material may be used to form the EIL.

Examples of materials for forming the EIL may include LiF, NaCl, CsF, $Li_2O$, and BaO. The deposition conditions of the EIL may be similar to those used to form the HIL, although the deposition conditions may vary according to the material that is used to form the EIL.

A thickness of the EIL may be in a range of about 1 Å to about 100 Å, e.g., about 3 Å to about 90 Å. When the thickness of the EIL is within the ranges described above, the EIL may have satisfactory electron transportation characteristics without a substantial increase in a driving voltage.

A second electrode may be disposed on the organic layer. The second electrode may be a cathode, which is an electron injection electrode. In this regard, a material for forming the second electrode may include metal, alloy, an electrically conductive compound, or a mixture thereof, each which has a low work function. For example, lithium (Li), magnesium (Mg), aluminum (Al), aluminum-lithium (Al—Li), calcium (Ca), magnesium-indium (Mg—In), magnesium-silver (Mg—Ag), etc. may be formed as a thin film for use as a transmissive electrode. In an implementation, to manufacture a top-emission light-emitting device, indium tin oxide (ITO) or indium zinc oxide (IZO) may be used to form a transmissive electrode.

Hereinbefore, the organic light-emitting device has been described with reference to FIG. 1.

In an implementation, when the EML includes a phosphorescent dopant, a hole blocking layer (HBL) may be formed between the ETL and the EML or between the E-functional layer and the EML by vacuum deposition, spin coating, casting, LB deposition, or the like, so as to help reduce and/or prevent diffusion of triplet excitons or holes into the ETL. When the HBL is formed by vacuum deposition or spin coating, the deposition or coating conditions may be similar to those applied to form the HIL, although the deposition or coating conditions may vary according to the material that is used to form the HBL. The hole blocking material may include, e.g., an oxadiazole derivative, a triazole derivative, a phenanthroline derivative, or the like. For example, bathocuproine (BCP) illustrated below may be used as a hole-blocking material.

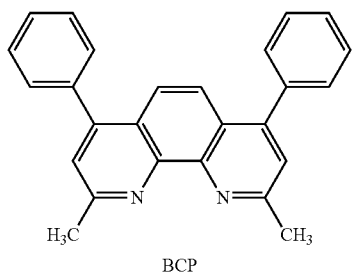

BCP

A thickness of the HBL may be in a range of about 20 Å to about 1,000 Å, e.g., about 30 Å to about 300 Å. If a thickness of the HBL is within the ranges described above, excellent hole blocking properties may be obtained without a substantial increase in driving voltage.

An organic light-emitting device according to an embodiment may be used in various flat panel display apparatuses, such as a passive matrix organic light-emitting display apparatus or an active matrix organic light-emitting display apparatus. For example, when the organic light-emitting device is included in an active matrix organic light-emitting display apparatus, the first electrode disposed on a substrate functions as a pixel and may be electrically connected to a source electrode or a drain electrode of a thin film transistor. In addition, the organic light-emitting device may be included in a flat panel display apparatus that emits light in opposite directions.

The organic layer of an organic light-emitting device according to an embodiment may be formed by depositing a compound according to an embodiment, or by coating a compound according to an embodiment prepared as a solution. The latter method is a wet method.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example

Synthesis Example 1

Synthesis of Compound 1

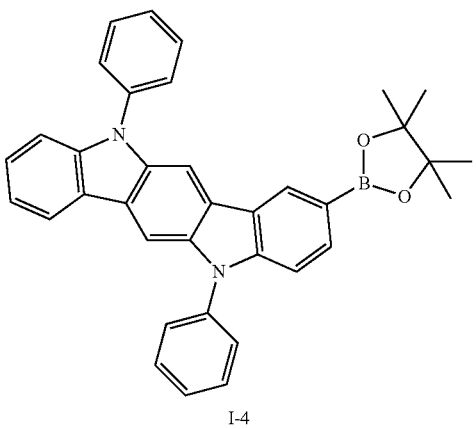

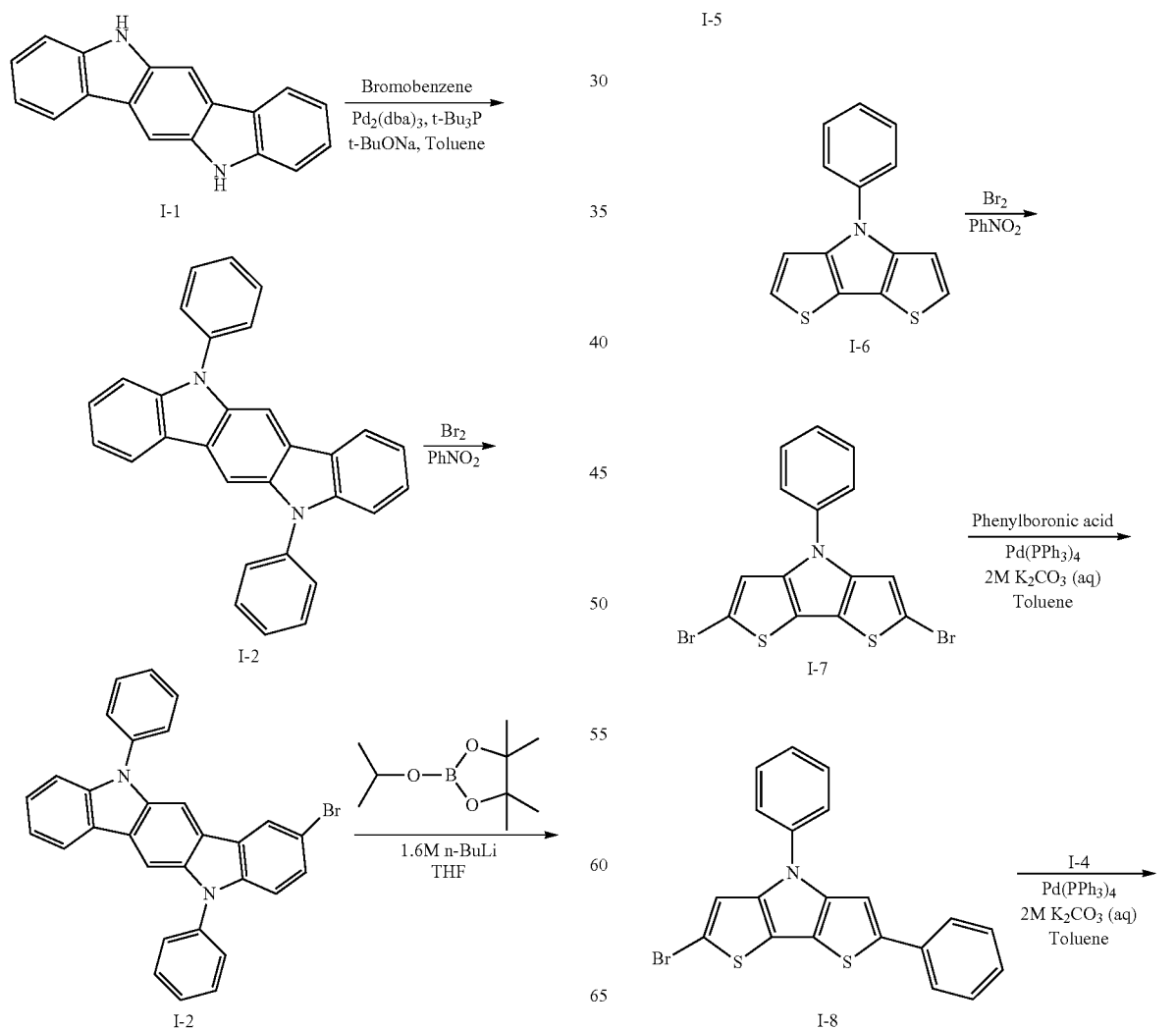

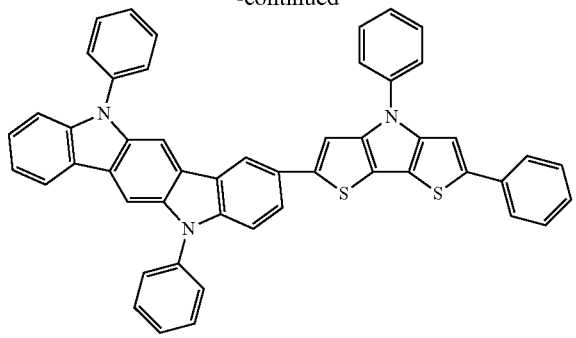

1

Synthesis of Intermediate 1-2

357.3 mg (0.39 mmol) of Pd$_2$(dba)$_3$ and 157.9 mg (0.78 mmol) of t-Bu$_3$P were dissolved in 50 ml of o-xylene, and then, the mixture was stirred for 10 minutes at room temperature. 5 g (19.51 mmol) of 5,11-dihydroindolo[3,2-b]carbazole, 7.35 g (46.82 mmol) of bromobenzene, and 2.25 g (23.41 mmol) of t-BuONa were added thereto, and the result was stirred while refluxing at a temperature of 160° C. for 48 hours. When the reaction was completed, 20 ml of cold distilled water was added thereto, and the reaction solution was extracted by using ethyl acetate. The extraction product was dried by using magnesium sulfate and filtered and then, a solvent was removed therefrom by evaporation. Thereafter, 6.79 g (Yield: 85%) of Intermediate 1-2 (5,11-diphenyl-5,11-dihydroindolo[3,2-b]carbazole) was obtained by column chromatography. EI-MS, m/e, 408.16 (calcd), 408.19 (found).

Synthesis of Intermediate 1-3

10 g (24.48 mmol) of Intermediate 1-2 was dissolved in 80 ml of nitrobenzene and then, the mixture was stirred at a temperature of 80° C. 1.25 ml (24.18 mmol) of bromine was diluted with 20 ml of nitrobenzene, and the diluent was slowly added thereto, and the result was stirred while refluxing at a temperature of 100° C. for 3 hours. After a saturated NaHSO$_3$ aqueous solution was added thereto, a generated solid was collected by filtering, and the filtrate was washed with distilled water and then n-hexane, and vacuum-dried to obtain 11.1 g (Yield: 93%) of Intermediate 1-3 (2-bromo-5,11-diphenyl-5,11-dihydroindolo[3,2-b]carbazole). EI-MS, m/e, 486.07 (calcd), 486.11 (found).

Synthesis of Intermediate 1-4

10 g (20.52 mmol) of Intermediate 1-3 was dissolved in 170 ml of THF, and then the mixture was stirred at a temperature of −78° C. 13.46 ml (21.54 mmol) of 1.6 M n-BuLi was slowly added thereto, and then, the result was stirred at a temperature of −78° C. for 30 minutes. 5.02 ml (24.62 mmol) of isopropoxy-4,4,5,5-tetramethyl[1,3,2]dioxaborolane was slowly added thereto, and then, the result was stirred at a temperature of −78° C. for 6 hours. When the reaction was completed, 100 ml of distilled water was added thereto, and the reaction solution was extracted by using ethyl acetate. The extraction product was dried by using magnesium sulfate and filtered and then, a solvent was removed therefrom by evaporation. Thereafter, 8.42 g (Yield: 77%) of Intermediate 1-4 (5,11-diphenyl-2-(4,4,5,5-tetramethyl-1,3,2-dioxaborolan-2-yl)-5,11-dihydroindolo[3,2-b]carbazole) was obtained by column chromatography. EI-MS, m/e, 534.25 (calcd), 534.23 (found).

Synthesis of Intermediate 1-6

510.8 mg (0.56 mmol) of Pd$_2$(dba)$_3$ and 225.7 mg (1.12 mmol) of t-Bu$_3$P were dissolved in 100 ml of o-xylene, and then, the mixture was stirred for 10 minutes at room temperature. 10 g (55.78 mmol) of 4H-dithieno[3,2-b:2',3'-d]pyrrole, 10.51 g (66.94 mmol) of bromobenzene, and 3.22 g (33.47 mmol) of t-BuONa were added thereto, and the result was stirred while refluxing at a temperature of 160° C. for 48 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 12.5 g (Yield: 88%) of Intermediate I-6 (4-phenyl-4H-dithieno[3,2-b:2',3'-d]pyrrole) was obtained by column chromatography. EI-MS, m/e, 255.02 (calcd), 255.04 (found).

Synthesis of Intermediate 1-7

10 g (39.16 mmol) of Intermediate 1-6 was dissolved in 80 ml of nitrobenzene and then, the mixture was stirred at a temperature of 80° C. 4.01 ml (78.32 mmol) of bromine was diluted with 20 ml of nitrobenzene, and the diluent was slowly added thereto, and the result was stirred while refluxing at a temperature of 100° C. for 3 hours. After a saturated NaHSO$_3$ aqueous solution was added thereto, a generated solid was collected by filtering, and the filtrate was washed with distilled water and then n-hexane, and vacuum-dried to obtain 15.1 g (Yield: 93%) of Intermediate 1-7 (2,6-dibromo-4-phenyl-4H-dithieno[3,2-b:2',3'-d]pyrrole). EI-MS, m/e, 410.84 (calcd), 410.85 (found).

Synthesis of Intermediate 1-8

5 g (12.10 mmol) of Intermediate 1-7, 1.77 g (14.52 mmol) of phenylboronic acid, and 699 mg (0.61 mmol) of tetrakis(triphenylphosphine)palladium(0) were dissolved in 30 ml of 2 M K$_2$CO$_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 3.43 g (Yield: 69%) of Intermediate 1-8 (2-bromo-4,6-diphenyl-4,4-dithieno[3,2-b:2',3'-d]pyrrole) was obtained by column chromatography. EI-MS, m/e, 408.96 (calcd), 408.98 (found).

Synthesis of Compound 1

5 g (9.36 mmol) of Intermediate 1-4, 4.61 g (11.23 mmol) of Intermediate 1-8, and 540 mg (0.47 mmol) of tetrakis(triphenylphosphine)palladium(0) were dissolved in 23 ml of 2 M K$_2$CO$_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 4.68 g (Yield: 68%) of Compound 1 (2-(5,11-diphenyl-5,11-dihydroindolo[3,2-b]carbazol-2-yl)-4,6-diphenyl-4H-dithieno[3,2-b:2',3'-d]pyrrole) was obtained by column chromatography. $^1$H NMR (300 MHz, CDCl$_3$), d (ppm): 8.84-8.76 (1H, s), 8.53-8.47 (1H, m), 8.02-7.96 (1H, s), 7.89-7.73 (7H, m), 7.67-7.58 (7H, m), 7.54-7.37 (9H, m), 7.29-7.21 (4H, m), 7.20-7.12 (1H, m). EI-MS, m/e, 737.20 (calcd), 737.24 (found).

Synthesis Example 2

Synthesis of Compound 4

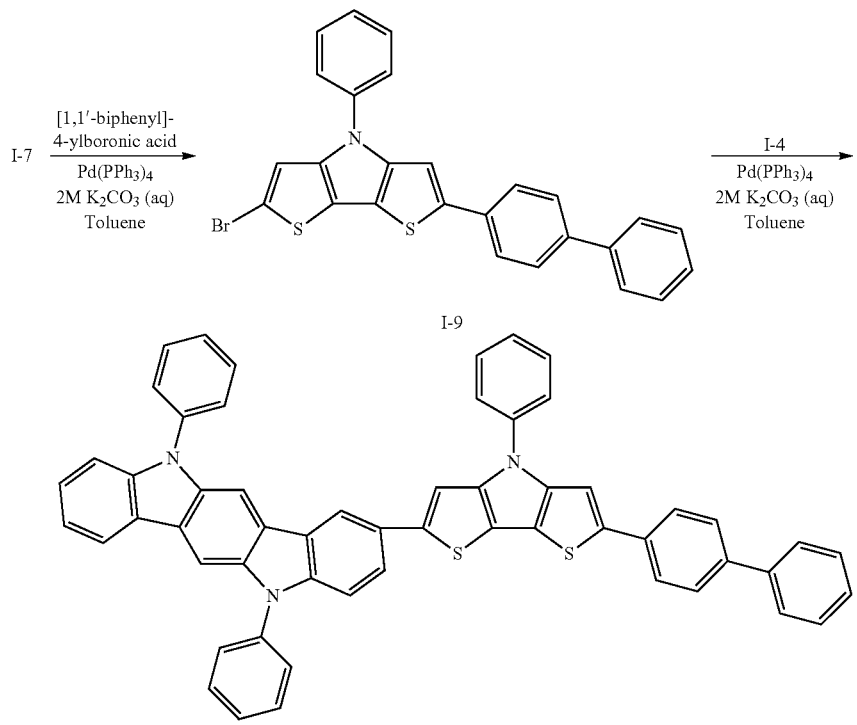

Synthesis of Intermediate 1-9

5 g (12.10 mmol) of Intermediate 1-7, 2.88 g (14.52 mmol) of [1,1'-biphenyl]-4-ylboronic acid, and 699 mg (0.61 mmol) of tetrakis(triphenylphosphine)palladium(0) were dissolved in 30 ml of 2 M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 3.94 g (Yield: 67%) of Intermediate 1-9 (2-([1,1'-biphenyl]-4-yl)-6-bromo-4-phenyl-4H-dithieno[3,2-b:2',3'-d]pyrrole) was obtained by column chromatography. ELMS, m/e, 484.99 (calcd), 484.97 (found).

Synthesis of Compound 4

5 g (9.36 mmol) of Intermediate 1-4, 5.46 g (11.23 mmol) of Intermediate 1-9, and 540 mg (0.47 mmol) of tetrakis(triphenylphosphine)palladium(0) were dissolved in 23 ml of 2 M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 5.06 g (Yield: 66%) of Compound 4 (2-([1,1'-biphenyl]-4-yl)-6-(5,11-diphenyl-5,11-dihydroindolo[3,2-b]carbazol-2-yl)-4-phenyl-4H-dithieno[3,2-b:2',3'-d]pyrrole) was obtained by column chromatography. $^1$H NMR (300 MHz, $CDCl_3$), d (ppm): 8.56-8.50 (1H, s), 8.49-8.43 (1H, s), 8.40-8.35 (1H, m), 8.06-8.01 (1H, s), 7.93-7.85 (4H, m), 7.85-7.79 (3H, m), 7.74-7.59 (10H, m), 7.52-7.43 (8H, m), 7.42-7.35 (1H, m), 7.34-7.24 (4H, m), 7.22-7.14 (1H, m). EI-MS, m/e, 813.23 (calcd), 813.26 (found).

Synthesis Example 3

Synthesis of Compound 15

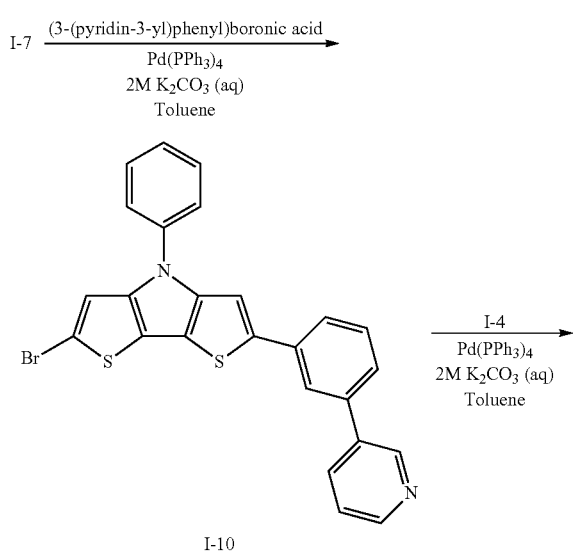

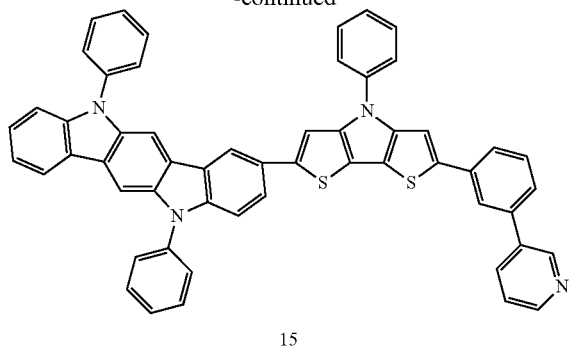

15

Synthesis of Intermediate I-10

5 g (12.10 mmol) of Intermediate 1-7, 2.89 g (14.52 mmol) of (3-(pyridin-3-yl)phenyl)boronic acid, and 699 mg (0.61 mmol) of tetrakis(triphenylphosphine) palladium(0) were dissolved in 30 ml of 2M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 4.02 g (Yield: 68%) of Intermediate I-10 (2-bromo-4-phenyl-6-(3-(pyridin-3-yl)phenyl)-4H-dithieno[3,2-b:2',3'-d]pyrrole) was obtained by column chromatography. EI-MS, m/e, 485.99 (calcd), 485.96 (found).

Synthesis of Compound 15

5 g (9.36 mmol) of Intermediate 1-4, 5.46 g (11.22 mmol) of Intermediate I-10, and 540 mg (0.468 mmol) of tetrakis(triphenylphosphine)palladium(0) were dissolved in 23 ml of 2 M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 5.28 g (Yield: 69%) of Compound 15 (2-(5,11-diphenyl-5,11-dihydroindolo[3,2-b]carbazol-2-yl)-4-phenyl-6-(3-(pyridin-3-yl)phenyl)-4H-dithieno[3,2-b:2',3'-d]pyrrole) was obtained by column chromatography. $^1$H NMR (300 MHz, CDCl$_3$), d (ppm): 9.14-9.07 (1H, m), 8.98-8.91 (1H, s), 8.69-8.63 (1H, m), 8.53-8.46 (1H, m), 8.33-8.25 (1H, s), 8.19-8.12 (1H, m), 8.01-7.95 (1H, s), 7.90-7.82 (4H, m), 7.81-7.73 (3H, m), 7.69-7.57 (8H, m), 7.55-7.41 (7H, m), 7.31-7.21 (4H, m), 7.20-7.12 (1H, m). ELMS, m/e, 814.22 (calcd), 814.23 (found).

Synthesis Example 4

Synthesis of Compound 16

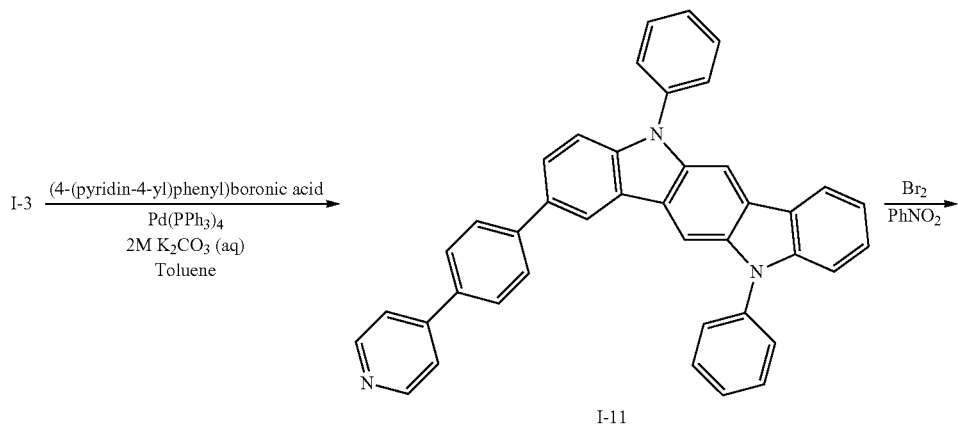

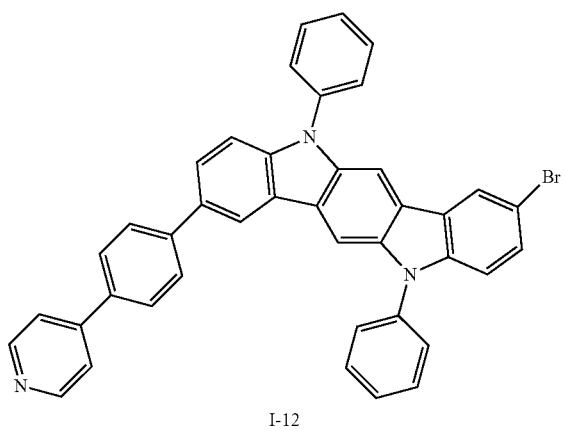

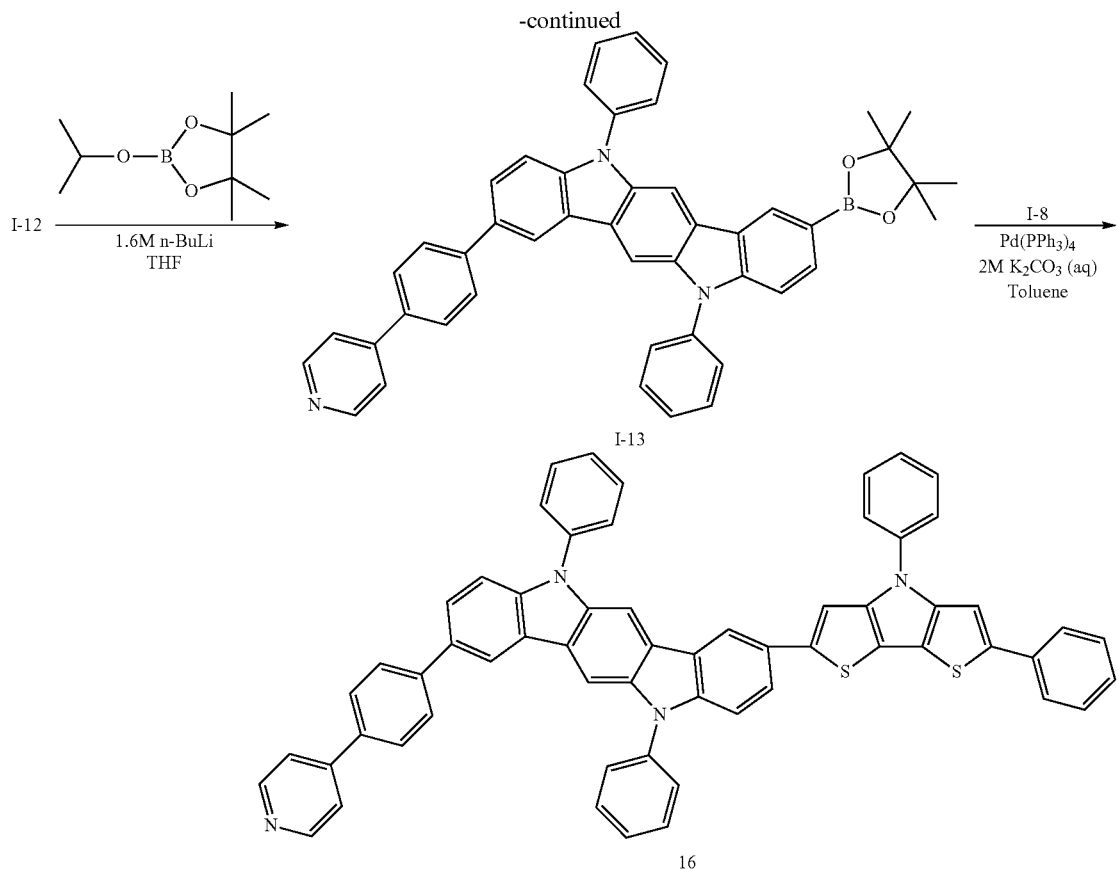

Synthesis of Intermediate I-11

5 g (10.26 mmol) of Intermediate 1-3, 2.45 g (12.31 mmol) of (4-(pyridin-4-yl)phenyl)boronic acid, and 593 mg (0.51 mmol) of tetrakis(triphenylphosphine) palladium(0) were dissolved in 26 ml of 2 M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 4.05 g (Yield: 70%) of Intermediate I-11 (5,11-diphenyl-2-(4-(pyridin-4-yl)phenyl)-5,11-dihydroindolo[3,2-b]carbazole) was obtained by column chromatography. EI-MS, m/e, 561.22 (calcd), 561.27 (found).

Synthesis of Intermediate 1-12

10 g (17.80 mmol) of Intermediate I-11 was dissolved in 80 ml of nitrobenzene and then, the mixture was stirred at a temperature of 80° C. 0.91 ml (17.80 mmol) of bromine was diluted with 20 ml of nitrobenzene, and the diluent was slowly added thereto, and the result was stirred while refluxing at a temperature of 100° C. for 3 hours. After saturated $NaHSO_3$ aqueous solution was added thereto, a generated solid was collected by filtering, and the filtrate was washed with distilled water and then n-hexane, and vacuum-dried to obtain 10.67 g (Yield: 94%) of Intermediate 1-12 (2-bromo-5,11-diphenyl-8-(4-(pyridin-4-yl)phenyl)-5,11-dihydroindolo[3,2-b]carbazole). m/e, 639.13 (calcd), 639.15 (found).

Synthesis of Intermediate I-13

10 g (15.61 mmol) of Intermediate 1-12 was dissolved in 170 ml of THF, and then the mixture was stirred at a temperature of −78° C. 10.2 ml (16.39 mmol) of 1.6 M n-BuLi was slowly added thereto, and then, the result was stirred at a temperature of −78° C. for 30 minutes. 3.8 ml (18.73 mmol) of isopropoxy-4,4,5,5-tetramethyl[1,3,2]dioxabororane was slowly added thereto, and then, the result was stirred at a temperature of −78° C. for 6 hours. When the reaction was completed, 100 ml of distilled water was added thereto, and the reaction solution was extracted by using ethyl acetate. The extraction product was dried by using magnesium sulfate and filtered and then, a solvent was removed therefrom by evaporation. Thereafter, 8.64 g (Yield: 80%) of Intermediate I-13 (5,11-diphenyl-2-(4-(pyridin-4-yl)phenyl)-8-(4,4,5,5-tetramethyl-1,3,2-dioxaborolan-2-yl)-5,11-dihydroindolo[3,2-b]carbazole) was obtained by column chromatography. EI-MS, m/e, 687.31 (calcd), 687.35 (found).

Synthesis of Compound 16

5 g (7.27 mmol) of Intermediate 1-13, 3.58 g (8.73 mmol) of Intermediate 1-8, and 420 mg (0.36 mmol) of tetrakis (triphenylphosphine)palladium(0) were dissolved in 18 ml of 2 M $K_2CO_3$(aq) and 50 ml of toluene, and then the mixture was stirred while refluxing at a temperature of 110° C. for 8 hours. When the reaction was completed, 40 ml of cold distilled water was added thereto, and the reaction solution was extracted by using ethyl acetate. The extraction product was dried by using magnesium sulfate and filtered and then, a solvent was removed therefrom by evaporation. Thereafter, 4.25 g (Yield: 66%) of Compound 16 (2-(5,11-diphenyl-8-(4-(pyridin-4-yl)phenyl)-5,11-dihydroindolo[3,2-b]carbazol-2-yl)-4,6-diphenyl-4H-dithieno[3,2-b:2',3'-d]pyrrole) was obtained by column chromatography. $^1$H NMR (300 MHz, $CDCl_3$), d (ppm): 8.79-8.72 (2H, m), 8.58-8.52 (1H, m), 8.45-8.39 (1H, m), 8.37-8.32 (1H, m), 8.31-8.26

(1H, m), 8.05-8.00 (1H, m), 7.93-7.80 (7H, m), 7.76-7.70 (3H, m), 7.69-7.58 (9H, m), 7.51-7.43 (8H, m), 7.41-7.35 (1H, m), 7.33-7.25 (3H, m). EI-MS, m/e, 890.25 (calcd), 890.23 (found).

Example 1

An anode was manufactured as follows: Corning 15 $\Omega/cm^2$ (1,200 Å) ITO glass substrate was cut to a size of 50 mm×50 mm×0.7 mm and sonicated with isopropyl alcohol and pure water each for 5 minutes, followed by irradiation to ultraviolet rays for 30 minutes and ozone, and the resultant glass substrate was placed in a vacuum deposition apparatus. On the substrate, 2-TNATA, a known hole injection material, was vacuum deposited to form a HIL having a thickness of 600 Å, and then, 4,4'-bis[N-(1-naphthyl)-N-phenylamino]biphenyl (NPB), a hole transportation compound, was vacuum deposited to form a HTL having a thickness of 300 Å. On the HTL, Compound 1 and [bis-(1-phenylisoquinolyl)iridium(III)acetylacetonate]((piq)$_2$Ir(acac)) were co-deposited at a weight ratio of 87:13 to form an EML having a thickness of 300 Å. Subsequently, tris-(8-hydroxyquinoline)aluminum (Alq3) was deposited on the EML to form an ETL having a thickness of 300 Å, and then, LiF, which is a halogenated alkali metal, was deposited on the ETL to form an EIL having a thickness of 10 Å, and Al was vacuum deposited to form a cathode having a thickness of 3,000 Å to form an LiF/Al electrode, thereby completing manufacturing of an organic light-emitting device.

The device had a driving voltage of 5.9 V and a red emission having a luminescent efficiency of 17.4 cd/A, at a brightness of 1,000 cd/m$^2$.

Example 2

An organic light-emitting device was manufactured in the same manner as in Example 1, except that in forming the EML, Compound 5 was used instead of Compound 1.

The device had a driving voltage of 6.1 V and a red emission having a luminescent efficiency of 18.1 cd/A, at a brightness of 1,000 cd/m$^2$.

Example 3

An organic light-emitting device was manufactured in the same manner as in Example 1, except that in forming the EML, Compound 12 was used instead of Compound 1.

The device had a driving voltage of 6.0 V and a red emission having a luminescent efficiency of 18.3 cd/A, at a brightness of 1,000 cd/m$^2$.

Example 4

An organic light-emitting device was manufactured in the same manner as in Example 1, except that in forming the EML, Compound 21 was used instead of Compound 1.

The device had a driving voltage of 5.8 V and a red emission having a luminescent efficiency of 17.8 cd/A, at a brightness of 1,000 cd/m$^2$.

Example 5

An organic light-emitting device was manufactured in the same manner as in Example 1, except that in forming the EML, Compound 4 was used instead of Compound 1 and tris[2-phenylpyridinato-C2,N]iridium(III)(Ir(ppy)$_3$) was used instead of (piq)$_2$Ir(acac).

The device had a driving voltage of 5.5 V and a green emission having a luminescent efficiency of 24.5 cd/A, at a brightness of 1,000 cd/m$^2$.

Example 6

An organic light-emitting device was manufactured in the same manner as in Example 5, except that in forming the EML, Compound 18 was used instead of Compound 4.

The device had a driving voltage of 5.7 V and a green emission having a luminescent efficiency of 26.2 cd/A, at a brightness of 1,000 cd/m$^2$.

Example 7

An organic light-emitting device was manufactured in the same manner as in Example 5, except that in forming the EML, Compound 27 was used instead of Compound 4.

The device had a driving voltage of 5.2 V and a green emission having a luminescent efficiency of 25.8 cd/A, at a brightness of 1,000 cd/m$^2$.

Example 8

An organic light-emitting device was manufactured in the same manner as in Example 5, except that in forming the EML, Compound 32 was used instead of Compound 4.

The device had a driving voltage of 5.6 V and a green emission having a luminescent efficiency of 24.8 cd/A, at a brightness of 1,000 cd/m$^2$.

Example 9

An organic light-emitting device was manufactured in the same manner as in Example 1, except that in forming the EML, 9,10-di-naphthalene-2-yl-anthracene (ADN) was used instead of Compound 1 and 1,4-bis-(2,2-diphenylvinyl)biphenyl(DPVBi) was used instead of (piq)$_2$Ir(acac), and ADN and DPVBi were co-deposited at a weight ratio of 98:2 and the ETL was formed by using Compound 15 instead of Alq3.

The device had, at a current density of 50 mA/cm$^2$, a driving voltage of 6.4V, a blue emission having a luminescent brightness of 2,632 Cd/m$^2$, a luminescent efficiency of 4.8 cd/A, and a half-lifetime of 283 hours at 100 mA/cm$^2$.

Example 10

An organic light-emitting device was manufactured in the same manner as in Example 9, except that in forming the ETL, Compound 24 was used instead of Compound 15.

The device had, at a current density of 50 mA/cm$^2$, a driving voltage of 6.2 V, a blue emission having a luminescent brightness of 2,452 Cd/m$^2$, a luminescent efficiency of 4.6 cd/A, and a half-lifetime of 264 hours at 100 mA/cm$^2$.

Example 11

An organic light-emitting device was manufactured in the same manner as in Example 9, except that in forming the ETL, Alq3 was used instead of Compound 15 and in forming the HTL, Compound II was used instead of NPB.

The device had, at a current density of 50 mA/cm$^2$, a driving voltage of 6.3 V, a blue emission having a luminescent brightness of 2,621 Cd/m$^2$, a luminescent efficiency of 4.7 cd/A, and a half-lifetime of 257 hours at 100 mA/cm$^2$.

Example 12

An organic light-emitting device was manufactured in the same manner as in Example 11, except that in forming the HTL, Compound 16 was used instead of Compound 11.

The device had, at a current density of 50 mA/cm$^2$, a driving voltage of 6.4V, a blue emission having a luminescent brightness of 2,555 Cd/m$^2$, a luminescent efficiency of 4.5 cd/A, and a half-lifetime of 264 hours at 100 mA/cm$^2$.

Comparative Example 1

An organic light-emitting device was manufactured in the same manner as in Example 1, except that in forming the EML, CBP was used instead of Compound 1.

The device had a driving voltage of 7.6 V and a red emission having a luminescent efficiency of 10.9 cd/A, at a brightness of 1,000 cd/m².

Comparative Example 2

An organic light-emitting device was manufactured in the same manner as in Example 5, except that in forming the EML, Compound 401 below was used instead of Compound 4.

The device had a driving voltage of 7.5 V and a green emission having a luminescent efficiency of 18.3 cd/A, at a brightness of 1,000 cd/m².

401

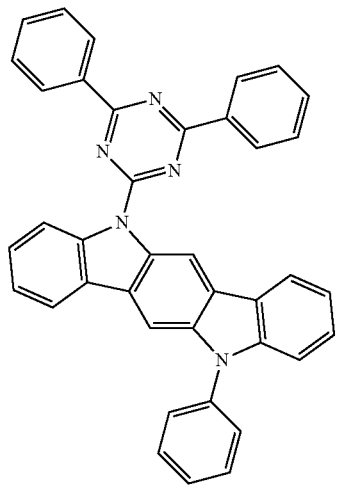

Comparative Example 3

An organic light-emitting device was manufactured in the same manner as in Example 9, except that in forming the ETL, Alq3 was used instead of Compound 15.

The device had, at a current density of 50 mA/cm², a driving voltage of 7.9 V, a blue emission having a luminescent brightness of 1,555 Cd/m², a luminescent efficiency of 3.2 cd/A, and a half-lifetime of 122 hours at 100 mA/cm².

Comparative Example 4

An organic light-emitting device was manufactured in the same manner as in Example 11, except that in forming the HTL, NPB was used instead of Compound 11.

The device had, at a current density of 50 mA/cm², a driving voltage of 7.8V, a blue emission having a luminescent brightness of 1,610 Cd/m², a luminescent efficiency of 3.2 cd/A, and a half-lifetime of 136 hours at 100 mA/cm².

Compounds represented by Formula 1 were used as a host material for green and red phosphorescent EMLs, a hole transportation material, or an electron transportation material. As a result, compared to CBP, Compound 401, Alq3, and NPB, the compounds had a high driving voltage, high efficiency, and excellent I-V-L characteristics. For example, lifespan improvement effects were high and thus, a lifespan was substantially prolonged. Representative characteristics and lifespan results are summarized and results thereof are shown in Table 1, below.

TABLE 1

| | Host for EML ETL material HTL material | Driving voltage voltage | Current density (mA/cm²) | Brightness (cd/m²) | Efficiency (cd/A) | Emission color | Lifespan LT97 (hr) |
|---|---|---|---|---|---|---|---|
| Example 1 | Compound 1 | 5.9 | 5.7 | 1000 | 17.4 | Red | 634 |
| Example 2 | Compound 5 | 6.1 | 5.5 | 1000 | 18.1 | Red | 605 |
| Example 3 | Compound 12 | 6.0 | 5.5 | 1000 | 18.3 | Red | 652 |
| Example 4 | Compound 21 | 5.8 | 5.6 | 1000 | 17.8 | Red | 591 |
| Example 5 | Compound 4 | 5.5 | 4.1 | 1000 | 24.5 | Green | 325 |
| Example 6 | Compound 18 | 5.7 | 3.8 | 1000 | 26.2 | Green | 306 |
| Example 7 | Compound 27 | 5.2 | 3.9 | 1000 | 25.8 | Green | 315 |
| Example 8 | Compound 32 | 5.6 | 4.0 | 1000 | 24.8 | Green | 292 |
| Example 9 | Compound 15 | 6.4 | 50 | 2632 | 4.8 | Blue | 283 |
| Example 10 | Compound 24 | 6.2 | 50 | 2452 | 4.6 | Blue | 264 |
| Example 11 | Compound 11 | 6.3 | 50 | 2621 | 4.7 | Blue | 257 |
| Example 12 | Compound 16 | 6.4 | 50 | 2555 | 4.5 | Blue | 264 |
| Comparative Example 1: | CBP | 7.6 | 9.2 | 1000 | 10.9 | Red | 346 |
| Comparative Example 2: | Compound 401 | 7.5 | 5.5 | 1000 | 18.3 | Green | 192 |
| Comparative Example 3: | Alq3 | 7.9 | 50 | 1592 | 3.2 | Blue | 122 |
| Comparative Example 4: | NPB | 7.8 | 50 | 1610 | 3.2 | Blue | 136 |

One or more embodiments may include a material that has excellent electric characteristics, a high charge transporting capability, a high light-emitting capability, a high glass transition temperature, and a crystallization-preventing capability, and that is suitable for use as a material for a full color, such as red, green, blue, or white, of fluorescent and phosphorescent devices, and an organic light-emitting device that has high efficiency, low voltage, high brightness, and long lifespan due to the inclusion of the material.

By way of summation and review, an emission layer of an organic light-emitting device, which may have a single- or multi-layered structure and may be between an anode and a cathode, may emit red, green, or blue light according to an organic compound included therein. For example, for use as a green or red luminescent material, a compound containing a carbazole may be used. In the case of carbazole, it may be difficult to shift the wavelength to a longer wavelength.

The embodiments may provide a material that has excellent electric stability, a high charge transporting capability, a high light-emitting capability, a high glass transition temperature, and a crystallization-preventing ability.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1, below:

<Formula 1>

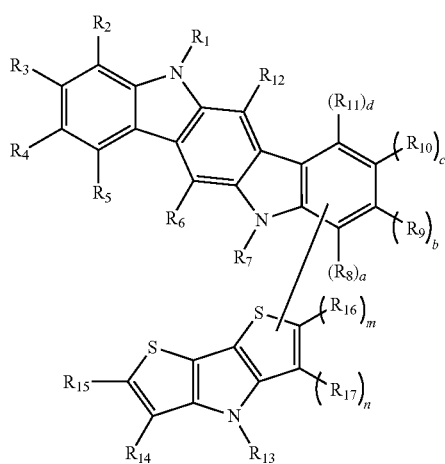

wherein, $R_1$ to $R_{17}$ are each independently a hydrogen atom, a deuterium atom, a substituted or unsubstituted $C_1$ to $C_{60}$ alkyl group, a substituted or unsubstituted $C_2$ to $C_{60}$ alkenyl group, a substituted or unsubstituted $C_2$ to $C_{60}$ alkynyl group, a substituted or unsubstituted $C_3$ to $C_{60}$ cycloalkyl group, a substituted or unsubstituted $C_1$ to $C_{60}$ alkoxy group, a substituted or unsubstituted $C_6$ to $C_{60}$ aryloxy group, a substituted or unsubstituted $C_6$ to $C_{60}$ arylthio group, a substituted or unsubstituted $C_6$ to $C_{60}$ aryl group, a substituted or unsubstituted $C_2$ to $C_{60}$ heteroaryl group, a substituted or unsubstituted $C_6$ to $C_{60}$ condensed polycyclic group, a halogen atom, a cyano group, a nitro group, a hydroxyl group, or a carboxyl group, and wherein a, b, c, d, m, and n are each independently 0 or 1, one of a, b, c, or d being 0, and one of m or n being 0.

2. The heterocyclic compound as claimed in claim 1, wherein the heterocyclic compound represented by Formula 1 is represented by Formula 2, below:

<Formula 2>

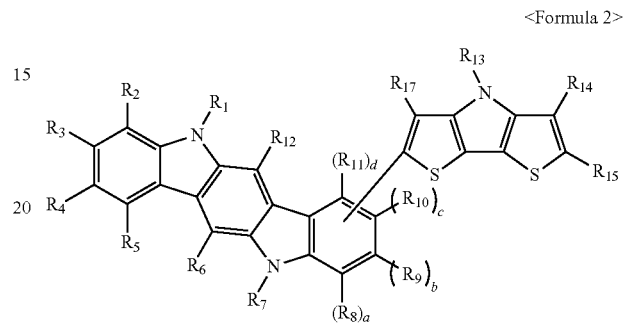

wherein $R_1$ to $R_{15}$, and $R_{17}$ in Formula 2 are the same as defined with respect to Formula 1, and wherein a, b, c, and d are each independently 0 or 1, one of a, b, c, or d being 0.

3. The heterocyclic compound as claimed in claim 1, wherein the heterocyclic compound represented by Formula 1 is represented by Formula 3, below:

<Formula 3>

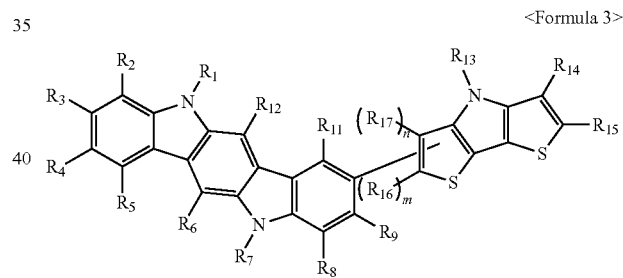

wherein $R_1$ to $R_9$, and $R_{11}$ to $R_{17}$ in Formula 3 are the same as defined with respect to Formula 1, and wherein m and n are each independently 0 or 1, one of m or n being 0.

4. The heterocyclic compound as claimed in claim 1, wherein the heterocyclic compound represented by Formula 1 is represented by Formula 4, below:

<Formula 4>

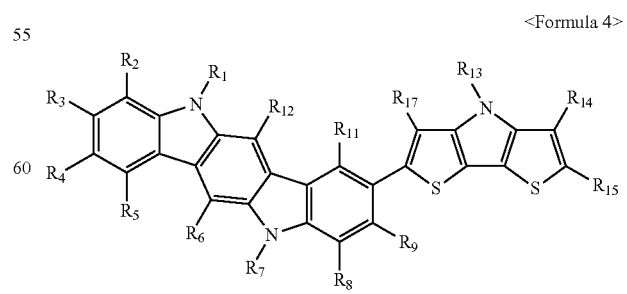

wherein $R_1$ to $R_9$, $R_{11}$ to $R_{15}$, and $R_{17}$ in Formula 4 are the same as defined with respect to Formula 1.

5. The heterocyclic compound as claimed in claim 1, wherein $R_1$, $R_3$, $R_4$, $R_7$, $R_{13}$, and $R_{15}$ in Formula 1 are each independently a substituted or unsubstituted $C_6$ to $C_{60}$ aryl group, a substituted or unsubstituted $C_2$ to $C_{60}$ heteroaryl group, or a substituted or unsubstituted $C_6$ to $C_{60}$ condensed polycyclic group.

6. The heterocyclic compound as claimed in claim 1, wherein $R_1$, $R_3$, $R_4$, $R_7$, $R_{13}$, and $R_{15}$ in Formula 1 are any one of Formulae 2a to 2d, below:

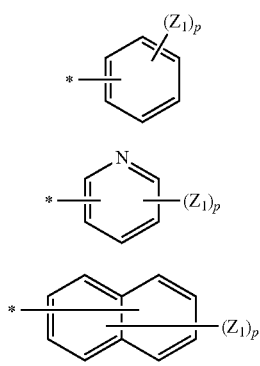

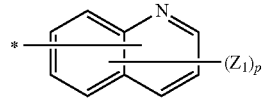

wherein, in Formulae 2a to 2d:

$Z_1$ and $Z_2$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, a halogen group, a cyano group, a nitro group, a hydroxyl group, or a carboxyl group;

p is an integer of 1 to 7; and

* indicates a binding site.

7. The heterocyclic compound as claimed in claim 1, wherein $R_2$, $R_5$, $R_6$, $R_8$ to $R_{12}$, $R_{14}$, $R_{16}$, and $R_{17}$ are each independently a hydrogen atom or a deuterium atom.

8. The heterocyclic compound as claimed in claim 1, wherein the compound represented by Formula 1 is any one of compounds 1-33, below:

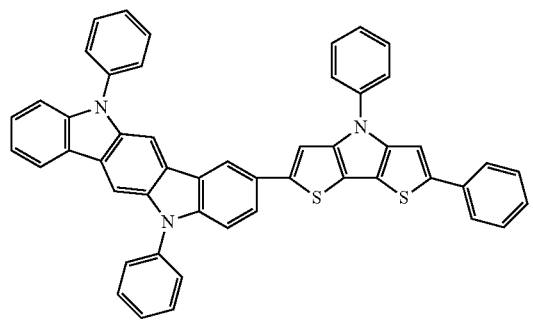

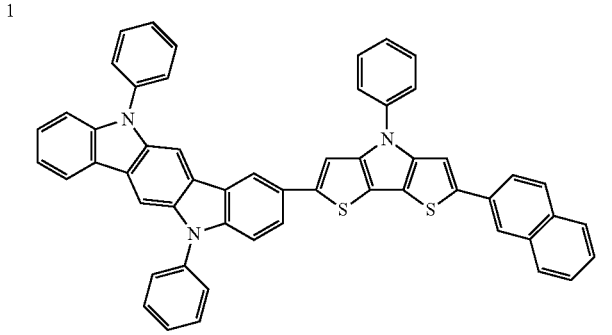

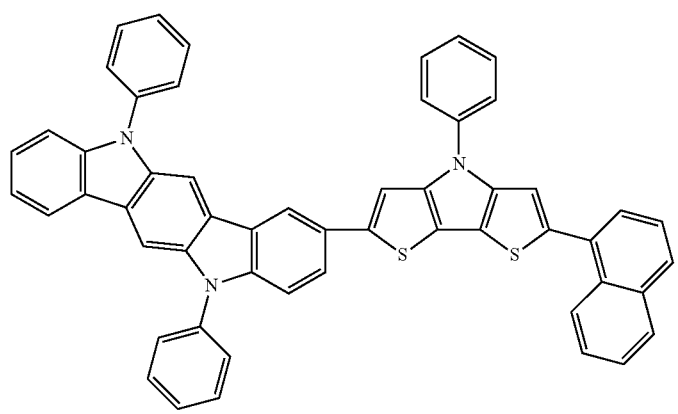

4
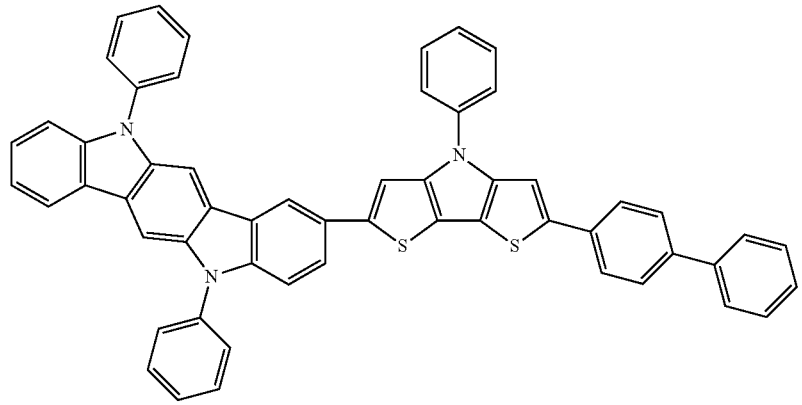
5
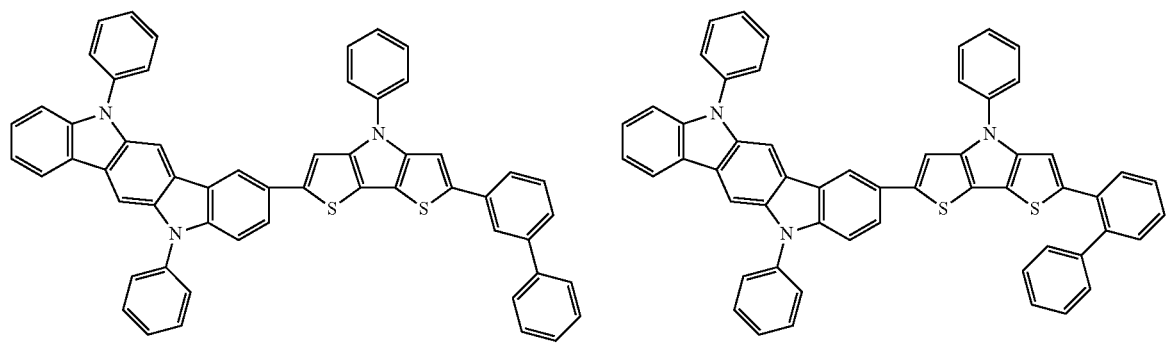
6
7
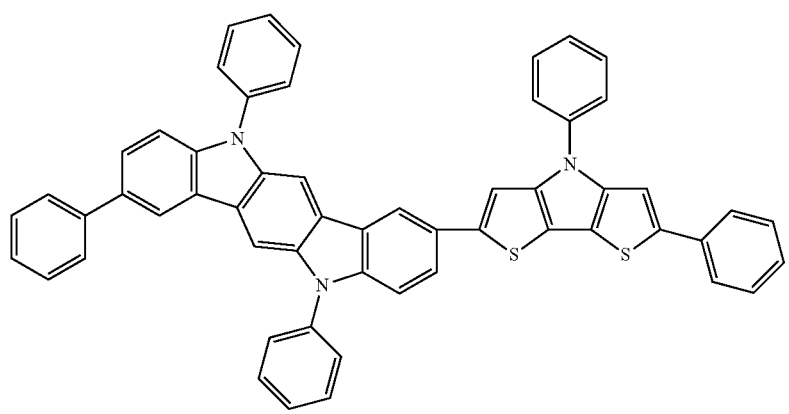
8
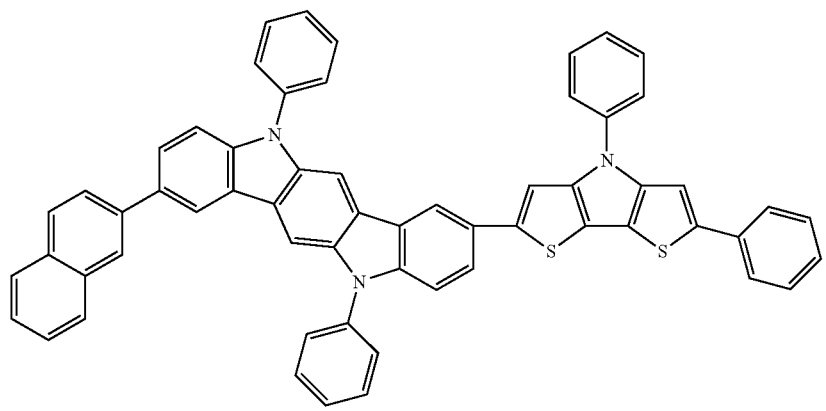

-continued
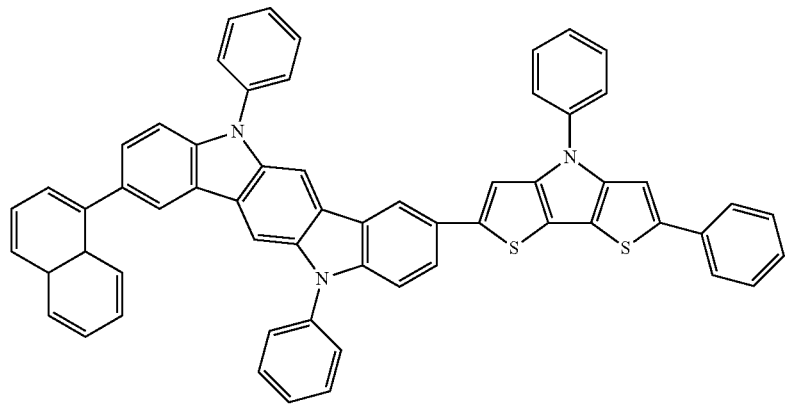
9
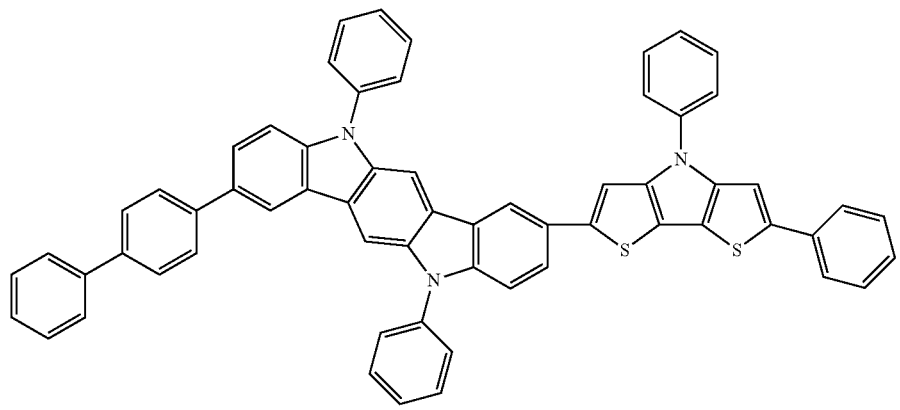
10
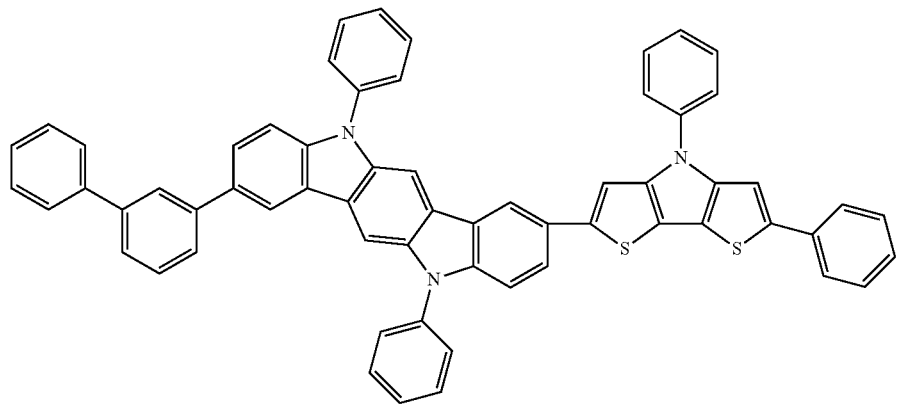
11
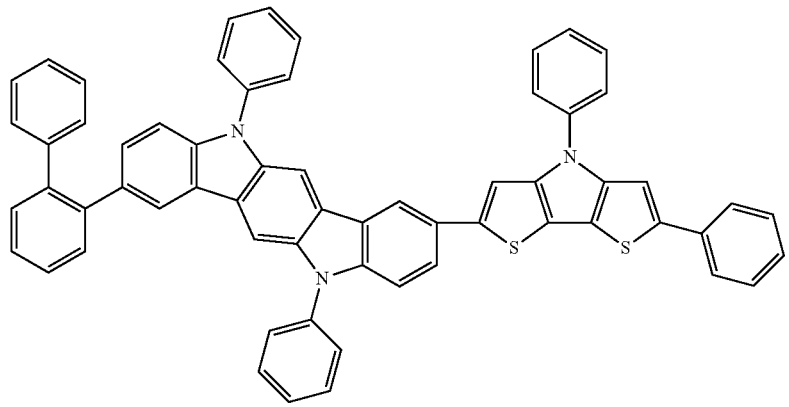
12

-continued
13
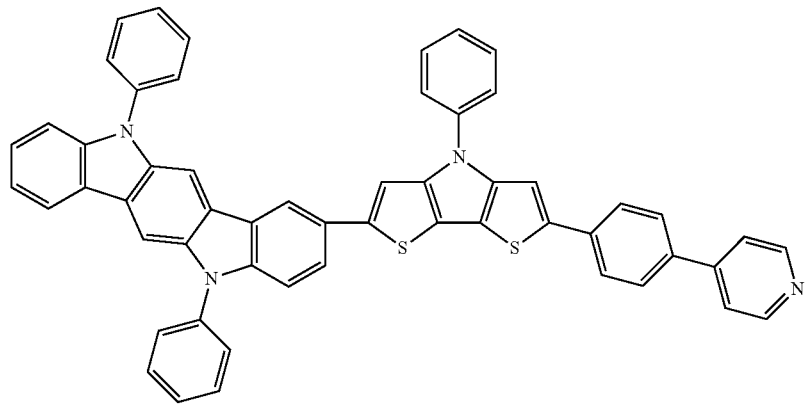
14
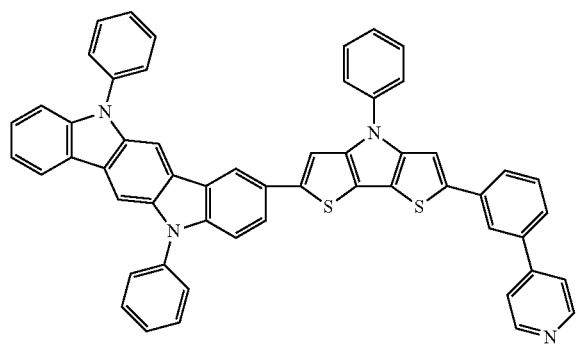
15
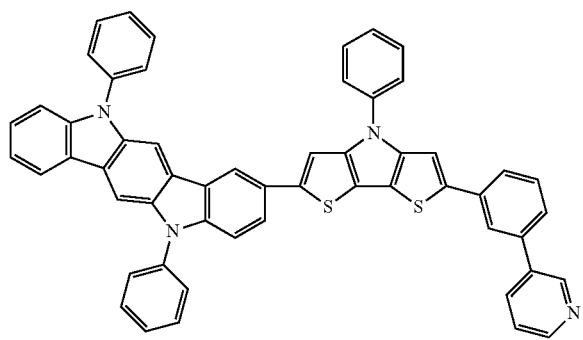
16
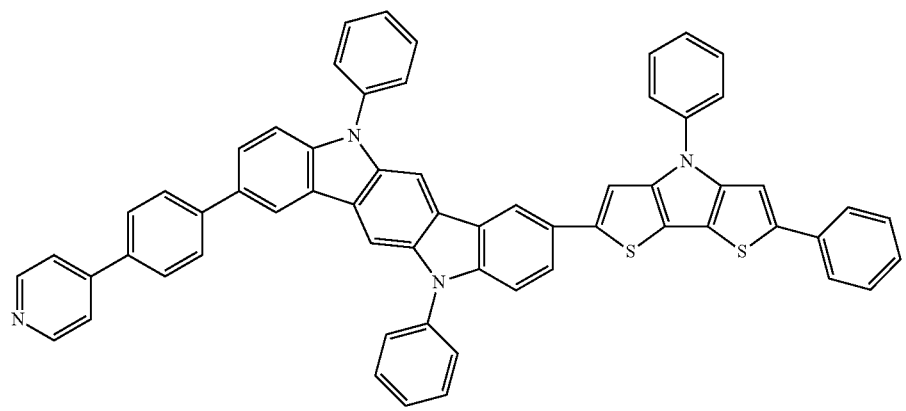
17
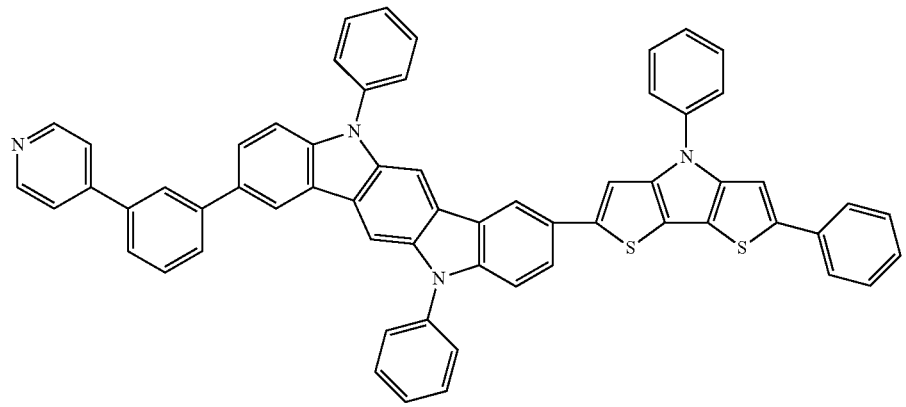

-continued
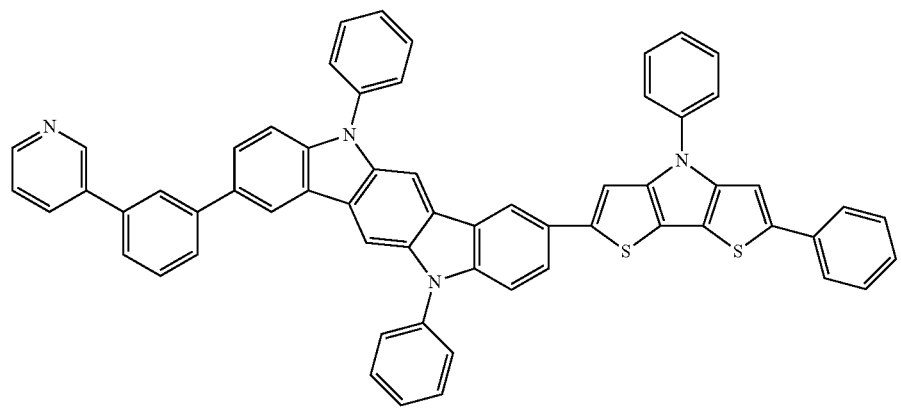
18
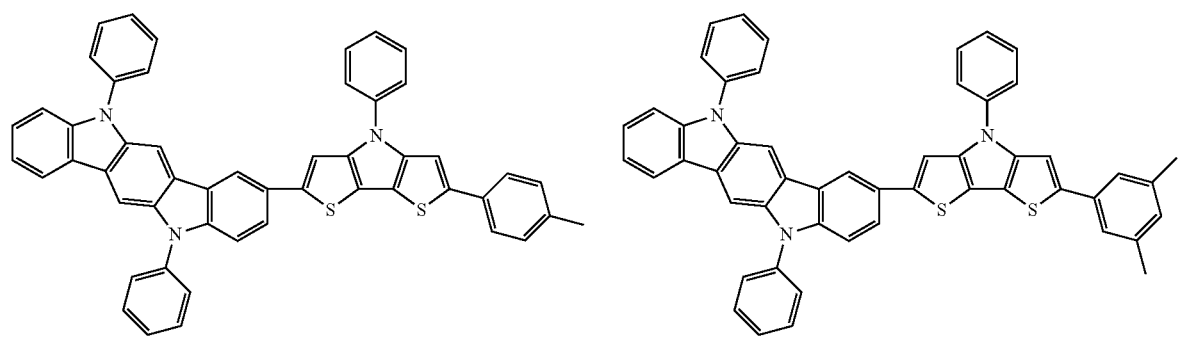
19  20
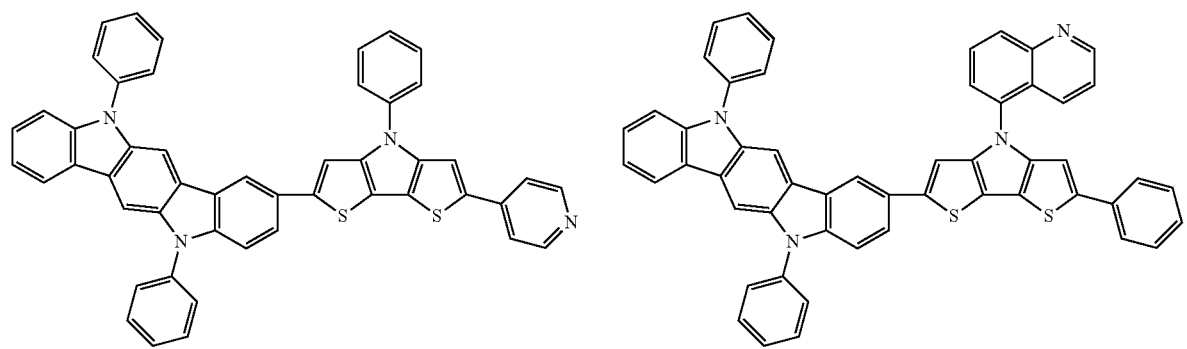
21  22
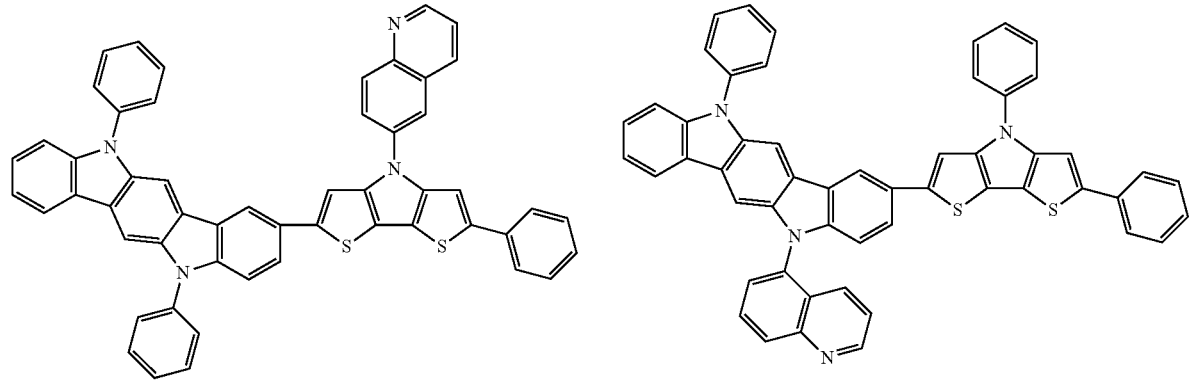
23  24

25
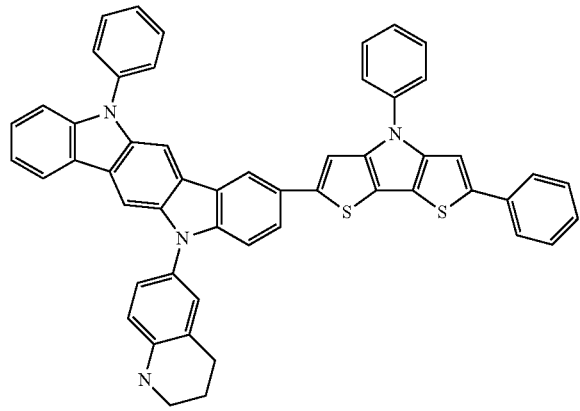
26
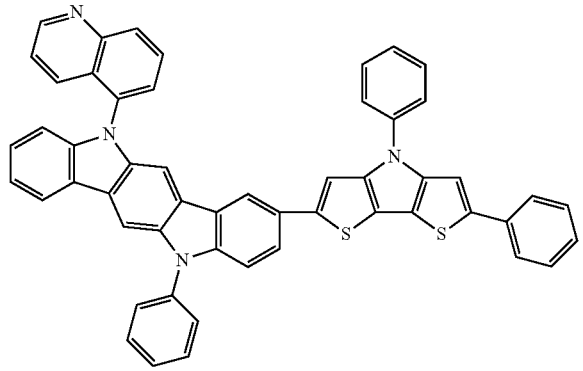
27
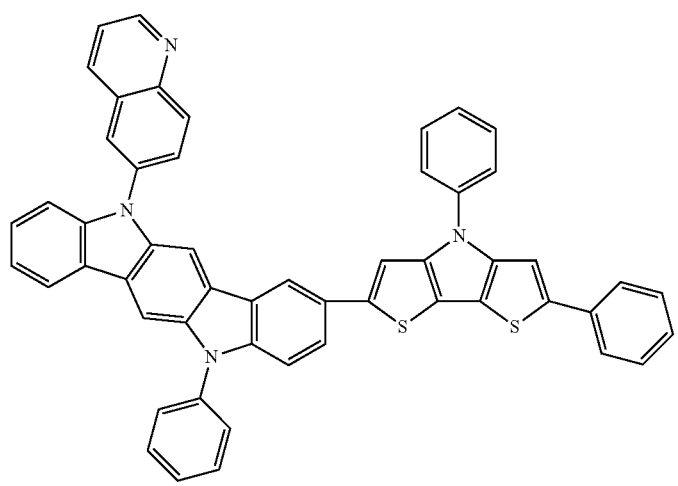
28
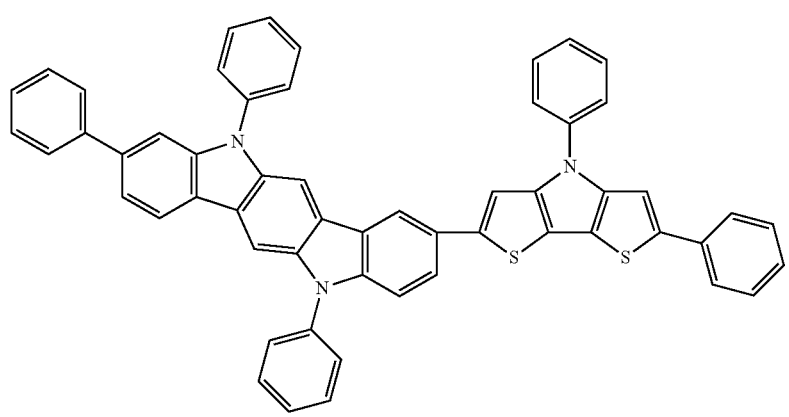

29
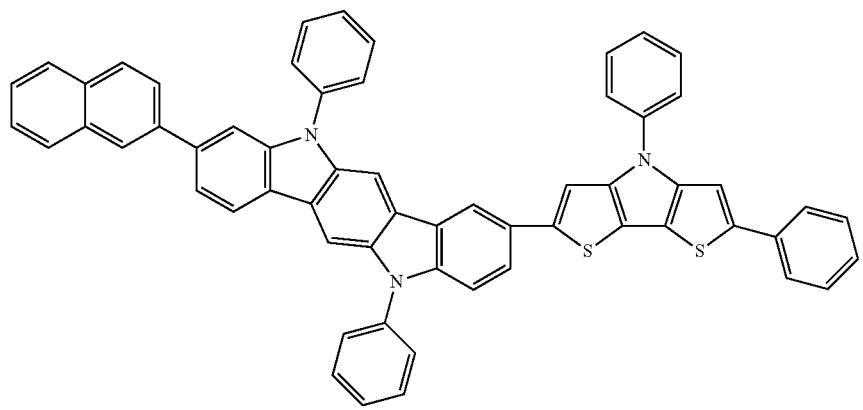
30
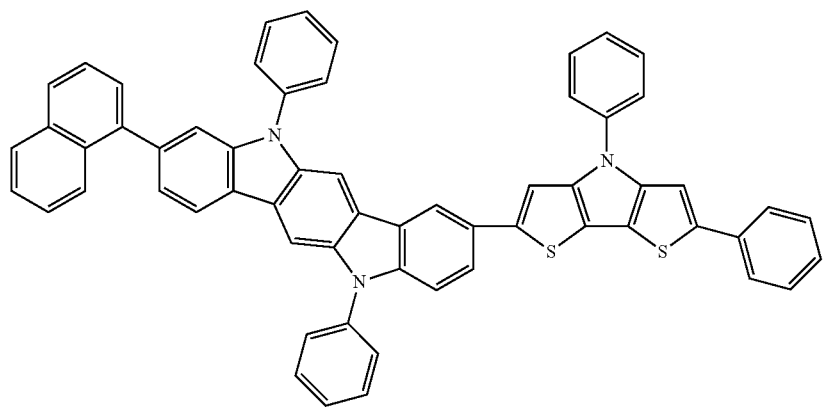
31
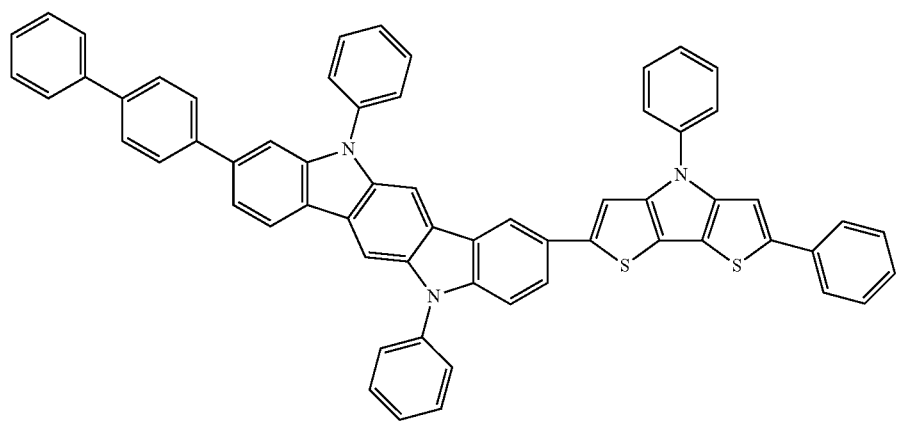
32
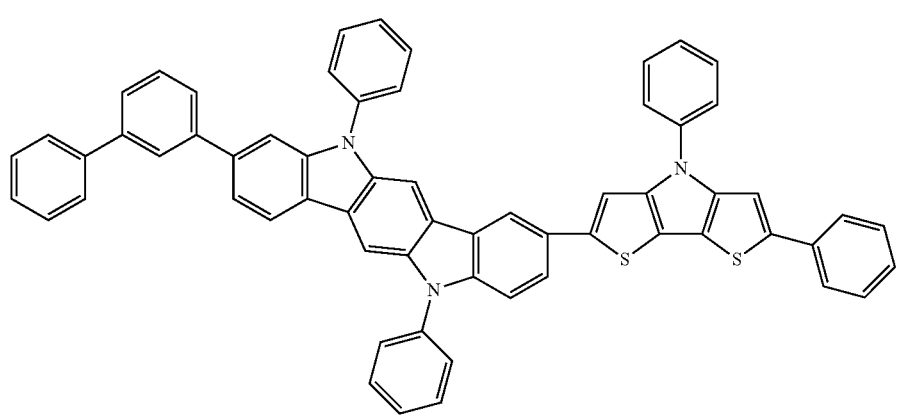

-continued

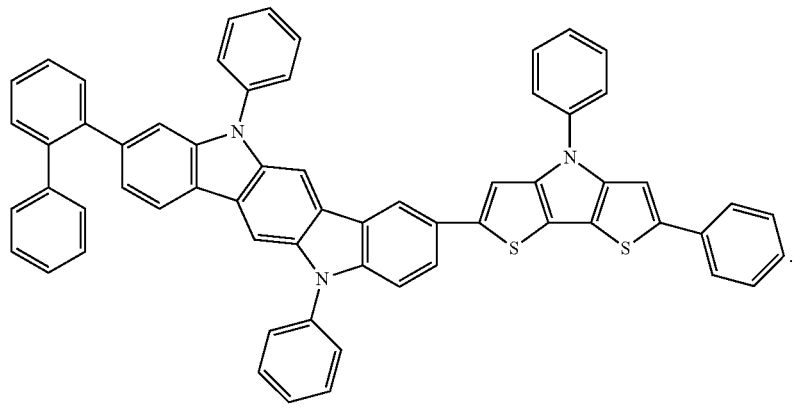

9. An organic light-emitting diode, comprising:
a first electrode;
a second electrode; and
an organic layer between the first electrode and the second electrode, wherein the organic layer includes the heterocyclic compound as claimed in claim 1.

10. The organic light-emitting device as claimed in claim 9, wherein the organic layer includes a hole injection layer, a hole transport layer, a functional layer having a hole injection capability and a hole transportation capability, an emission layer, an electron injection layer, an electron transport layer, or a functional layer having an electron injection capability and an electron transportation capability.

11. The organic light-emitting device as claimed in claim 9, wherein the organic layer is an emission layer, an electron transport layer, or a hole transport layer.

12. The organic light-emitting device as claimed in claim 9, wherein:
the organic layer includes an emission layer, and a hole injection layer, a hole transport layer, or a functional layer having a hole injection capability and a hole transportation capability, and
the emission layer includes a red layer, a green layer, a blue layer, and a white layer, one of which includes a phosphorescent compound.

13. The organic light-emitting device as claimed in claim 12, wherein the hole injection layer, the hole transport layer, or the functional layer having a hole injection capability and a hole transportation capability includes a charge-generation material.

14. The organic light-emitting device as claimed in claim 13, wherein the charge-generation material is a p-dopant.

15. The organic light-emitting device as claimed in claim 14, wherein the p-dopant is a quinone derivative, metal oxide, or a cyano group-containing compound.

16. The organic light-emitting device as claimed in claim 9, wherein the organic layer includes an electron transport layer, the electron transport layer including a metal-containing material.

17. The organic light-emitting device as claimed in claim 16, wherein the metal-containing material is a Li complex.

18. The organic light-emitting device as claimed in claim 16, wherein the metal-containing material includes one of lithium quinolate (LiQ) or Compound 203 below:

<203>

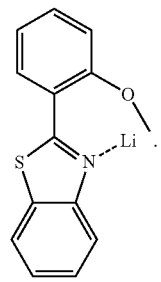

19. The organic light-emitting device as claimed in claim 9, wherein the organic layer is formed by using a wet process performed by using the heterocyclic compound.

20. A flat panel display apparatus, comprising the organic light-emitting device as claimed in claim 9, wherein the first electrode of the organic light-emitting device is electrically connected to a source electrode or a drain electrode of a thin film transistor.

* * * * *